(12) United States Patent
Khatwani et al.

(10) Patent No.: US 11,725,192 B2
(45) Date of Patent: Aug. 15, 2023

(54) SEPARATION AND QUANTIFICATION OF EMPTY AND FULL VIRAL CAPSID PARTICLES

(71) Applicant: Sangamo Therapeutics, Inc., Brisbane, CA (US)

(72) Inventors: Santoshkumar Khatwani, Raleigh, NC (US); Zhu Pirot, Redwood City, CA (US)

(73) Assignee: SANGAMO THERAPEUTICS, INC., Brisbane, CA (US)

( * ) Notice: Subject to any disclaimer, the term of this patent is extended or adjusted under 35 U.S.C. 154(b) by 423 days.

(21) Appl. No.: 16/926,732

(22) Filed: Jul. 12, 2020

(65) Prior Publication Data

US 2021/0009964 A1 Jan. 14, 2021

Related U.S. Application Data

(60) Provisional application No. 62/873,619, filed on Jul. 12, 2019.

(51) Int. Cl.
| | |
|---|---|
| *C12N 7/00* | (2006.01) |
| *B01D 15/00* | (2006.01) |
| *B01D 15/16* | (2006.01) |
| *B01D 15/36* | (2006.01) |
| *B01D 15/42* | (2006.01) |

(52) U.S. Cl.
CPC ............. *C12N 7/00* (2013.01); *B01D 15/166* (2013.01); *B01D 15/363* (2013.01); *B01D 15/424* (2013.01); *C12N 2750/14151* (2013.01)

(58) Field of Classification Search
CPC ............ C12N 7/00; C12N 2750/14151; B01D 15/166; B01D 15/363; B01D 15/424
See application file for complete search history.

(56) References Cited

U.S. PATENT DOCUMENTS

| | | | |
|---|---|---|---|
| 7,198,951 | B2 | 4/2007 | Gao et al. |
| 9,585,971 | B2 | 3/2017 | Deverman et al. |

FOREIGN PATENT DOCUMENTS

| | | | | |
|---|---|---|---|---|
| WO | 2017/160360 A2 | 9/2017 | | |
| WO | WO-2019178495 A1 | * | 9/2019 | ........... B01D 15/166 |

OTHER PUBLICATIONS

Agilent Technologies (the LC Handbook: Guide to LC Columns and Method Development, published in USA, Feb. 2, 2016). (https://www.agilent.com/cs/library/primers/Public/LC-Handbook-Complete-2.pdf).*
Santos et al. Fractionation of the major whey proteins and isolation of β-Lactoglobulin variants by anion exchange chromatography, Separation and Purification Technology. Separation and Purification Technology 90 (2012) 133-139.*
Zhang et al. Strategic Combination of Isocratic and Gradient Elution for Simultaneous Separation of Polar Compounds in Traditional Chinese Medicines by HPLC. J Anal Methods Chem. Mar. 19, 2018;2018:7569283.*
Balaji et al., "Pseudotyped Adeno-Associated Viral Vectors for Gene Transfer in Dermal Fibroblasts: Implications for Wound Healing Applications," J Surg Res. (2013) 184(1):691-98.
Clément, et al., "Manufacturing of Recombinant Adeno-associated Viral Vectors for Clinical Trials," Mol Ther Methods Clin Dev. (2016) 3:16002.
Hauck et al., "Generation and Characterization of Chimeric Recombinant AAV Vectors," Mol Ther. (2003) 7 (3):419-25.
Leuchs, et al., "A Novel Scalable, Robust Downstream Process for Oncolytic Rat Parvovirus: Isoelectric Point-based Elimination of Empty Particles", Appl Microbiol Biotechnol (2017) 101(8):3143-152.
Lock et al., "Characterization of a Recombinant Adeno-Associated Virus Type 2 Reference Standard Material," Hum. Gene Ther. (2010) 21:1273-285.
Urabe et al: "Removal of Empty Particles from Type 1 Adena-Associated Virus Vector Stocks by Ion Exchange Chromatography Potentiates Transgene Expression," Molecular Therapy (2006) 13:S427.

* cited by examiner

*Primary Examiner* — Janet L Andres
*Assistant Examiner* — Ruixue Wang
(74) *Attorney, Agent, or Firm* — Steptoe & Johnson LLP; Z. Ying Li; Debashree Chatterjee

(57) ABSTRACT

The present disclosure provides methods for the separation and quantification of empty and full viral capsids (e.g., AAV capsids) within a viral preparation, such as a viral pharmaceutical composition or drug product.

24 Claims, 37 Drawing Sheets

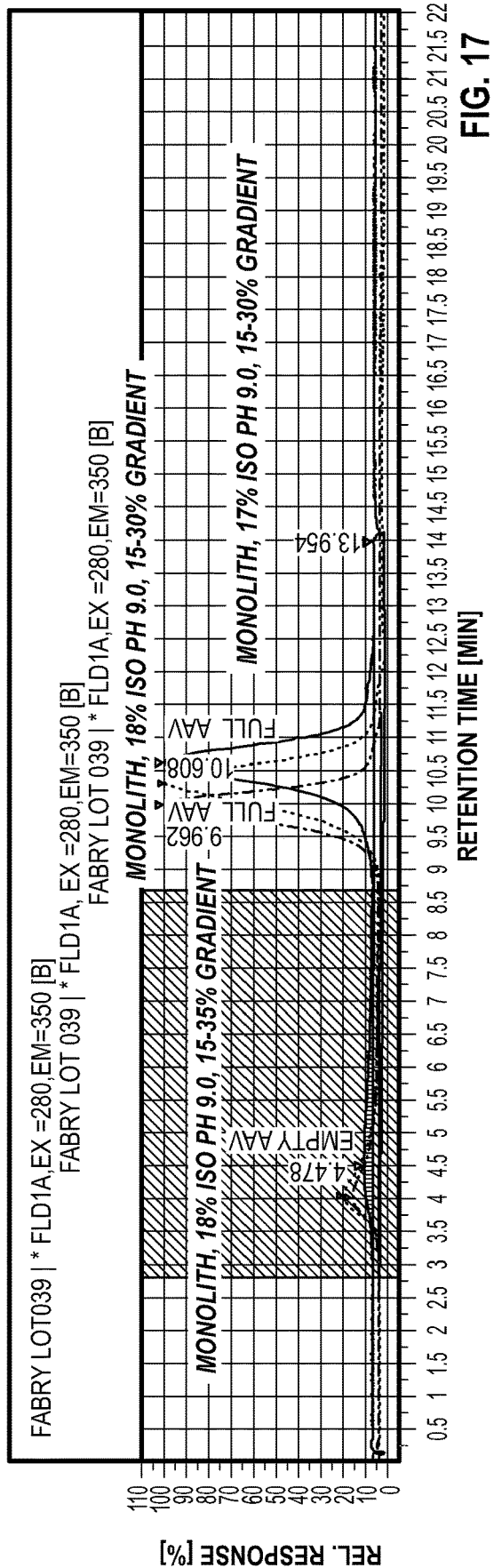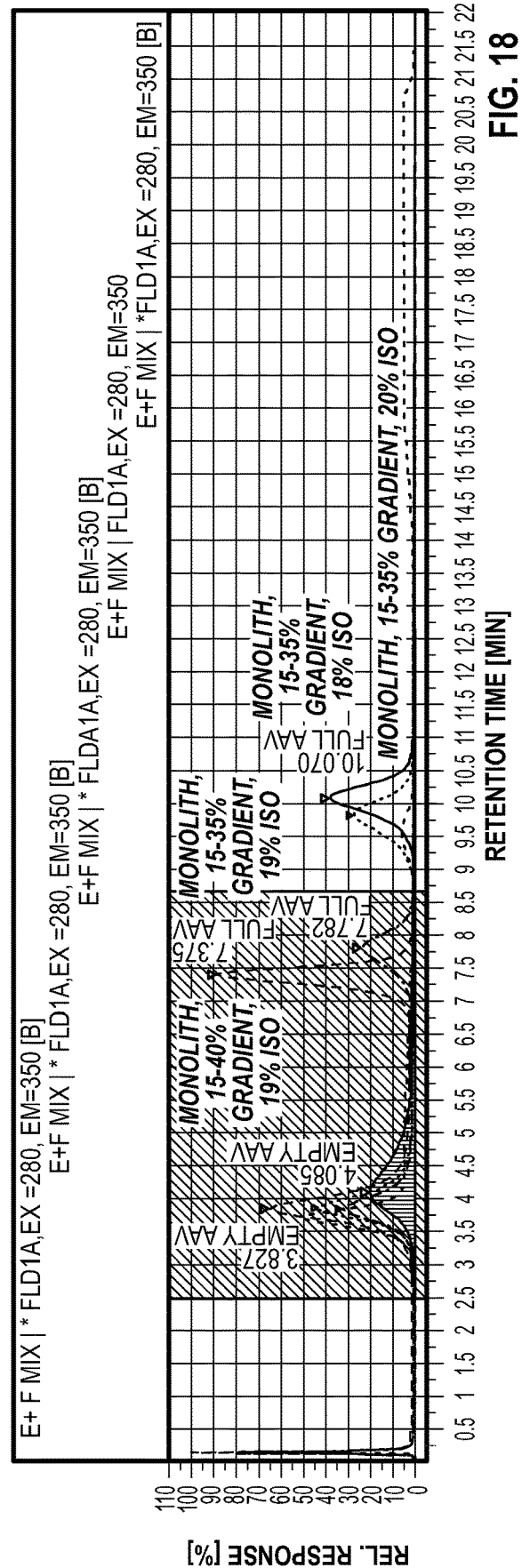

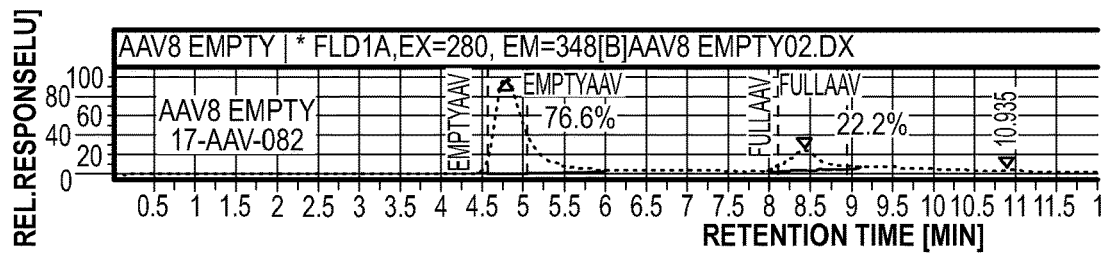
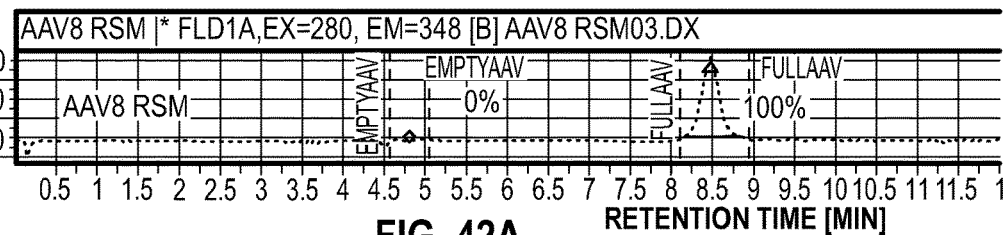
FIG. 42A
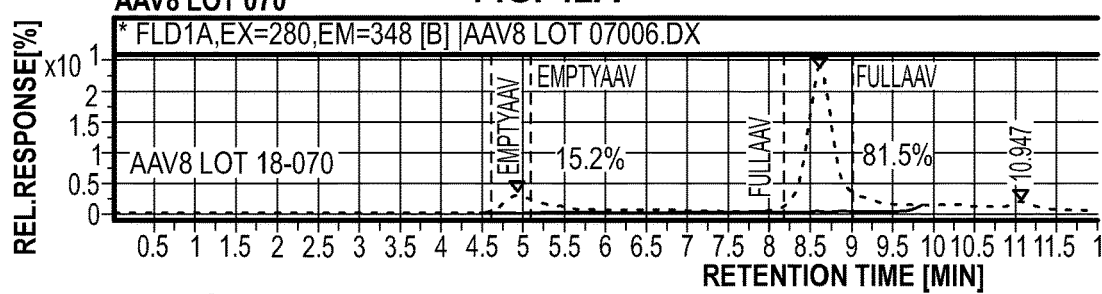
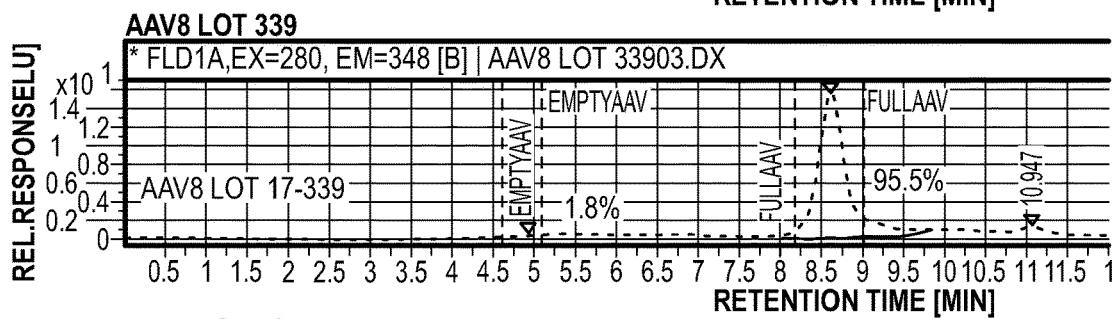
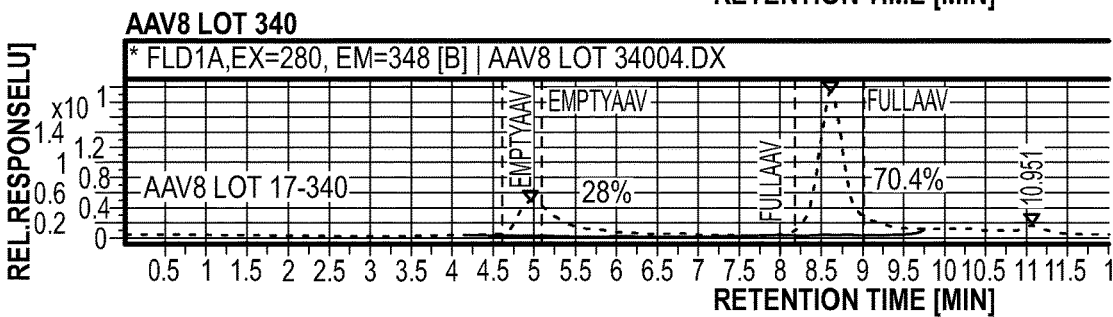
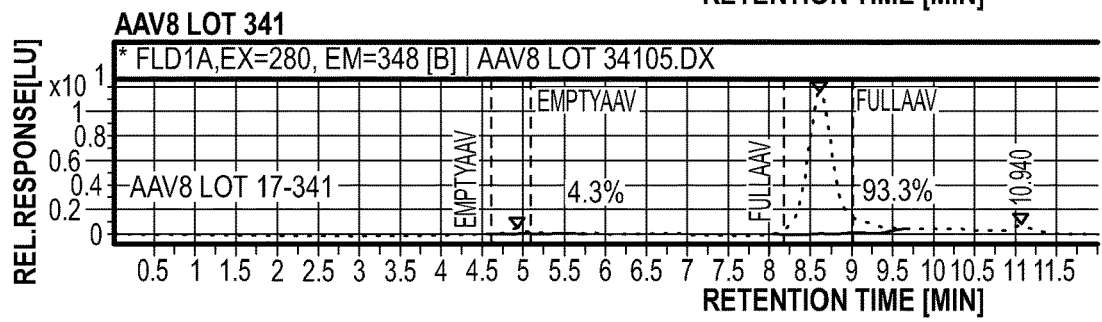
FIG. 42B

SEPARATION AND QUANTIFICATION OF EMPTY AND FULL VIRAL CAPSID PARTICLES

CROSS-REFERENCE TO RELATED APPLICATION

This application claims priority from U.S. Application 62/873,619, filed Jul. 12, 2019, the disclosure of which is incorporated herein by reference in its entirety.

BACKGROUND OF THE INVENTION

Adeno-associated virus (AAV) vectors have emerged as one of the most popular viral vector delivery systems in gene therapy. AAV-based gene delivery vectors (recombinant AAV or rAAV) comprise an AAV capsid harboring a therapeutic transgene. A feature of AAV vector production in cell culture is the formation of an excess of "empty" capsids, which lack the vector genome and are therefore unable to provide a therapeutic benefit. The effect of the empty capsids on clinical outcome is unclear, but the potential for increasing innate or adaptive immune responses to the vector is a major concern.

The development of analytical methods to quantify empty vector particles as an impurity has received special attention for characterization of viral preparations, pharmaceutical compositions and drug products. Currently available methods to determine the percent fraction of empty viral particles (or the empty to full ratio) are laborious, cumbersome, low throughput, and/or low resolution. There have been attempts to separate empty AAV and rAAV ("full") particles and to purify the rAAV particles by chromatographic methods during the manufacturing process; however, successful baseline peak resolution between peaks corresponding to empty particles and those corresponding to AAV vectors containing target genomes has yet to be achieved.

Thus, there remains a need for new AAV-specific assays for screening during the manufacturing process, vector product release, and/or drug product analysis that are well suited for the rigorous demands of high-quality standards such as current good manufacturing practices and USP standards.

SUMMARY OF THE INVENTION

The present disclosure provides a method of separating empty and full capsids (e.g., empty and full AAV capsids) in a viral preparation (e.g., an AAV preparation). The method comprises running the viral preparation and a mobile phase through an ion (e.g., anion or cation) exchange column, wherein the mobile phase is run under conditions comprising a discontinuous elution gradient and at least one (e.g., 1, 2, 3, 4, or 5) isocratic hold.

In another aspect, the present disclosure provides a method of quantitating empty and full capsids (e.g., empty and full AAV capsids) in a viral preparation (e.g., an AAV preparation). The method comprises running the viral preparation and a mobile phase through an anion or cation exchange column, wherein the mobile phase is run under conditions comprising a discontinuous elution gradient and at least one (e.g., 1, 2, 3, 4, or 5) isocratic hold.

In some embodiments of the present methods, the viral preparation and mobile phase are run on a high-performance liquid chromatography (HPLC) system.

In some embodiments, the empty and full capsids are separated by baseline resolution, such as a baseline resolution greater than 2.0.

In some embodiments, the anion exchange column used in the methods is a strong anion exchange (SAX) column, such as a quaternary amine (Q-amine) column. In some embodiments, the anion exchange column is a monolith column.

In some embodiments, the cation exchange column used in the methods is a strong cation exchange (SCX) column, such as a benzene sulfonic acid column. In some embodiments, the cation exchange column is a monolith column.

In some embodiments, the mobile phase used in the present methods comprises a salt. In further embodiments, the salt is tetramethylammonium chloride (TMAC) or sodium acetate. In certain embodiments, the final gradient of the mobile phase comprises 0.1 to 10 M (e.g., 0.5 to 5 M such as 1, 1.5, or 2 M) salt. In certain embodiments, the salt is 0.5 to 5 M (e.g., 1 M) TMAC or sodium acetate.

In some embodiments, the at least one isocratic hold is introduced before the mobile phase reaches 50% of the final gradient, e.g., before the mobile phase reaches 20%, 25%, 30%, 35%, 40%, or 45% of the final gradient.

In some embodiments, the pH of the mobile phase is about 8 to about 10, for example, about 9.

In some embodiments, the column has a temperature between 0° C. and 50° C., for example, between 20° C. and 25° C.

Also provided are highly purified recombinant viral compositions (e.g., AAV compositions) prepared by the present methods. In some embodiments, the viral compositions comprise 100% empty capsids or less than 100% (e.g., less than 95%, less than 90%, less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, less than 4%, less than less than 3%, less than 2%, or less than 1%) empty capsids. In particular embodiments, the present disclose provides a viral preparation that is enriched for empty viral capsids, the preparation being obtained by a method described herein, optionally wherein no more than 20% (e.g., no more than 15%, no more than 10%, no more than 5%, or no more than 1%) of the viral capsids in the preparation are full viral capsids. In particular embodiments, the present disclose provides a viral preparation that is enriched for full viral capsids, the preparation being obtained by a method described herein, optionally wherein no more than 20% (e.g., no more than 15%, no more than 10%, no more than 5%, or no more than 1%) of the viral capsids in the preparation are empty viral capsids.

In some embodiments, the AAV herein may be derived from one or more serotypes, such as AAV1, AAV2, AAV3, AAV6, AAV8, and AAV9.

In some embodiments, the recombinant AAV (rAAV) herein has a recombinant genome having a size of about 20 to 9,000 bases.

Other features, objectives, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

particles. FFB: final formulation buffer. rAAV6-GLA3: recombinant AAV6 carrying an alpha-galactosidase A (GLA) transgene. rAAV6-GLA2: a different production batch of the recombinant AAV6-GLA virus. AAV6 Empty: empty AAV6 capsid sample.

Figure 2:
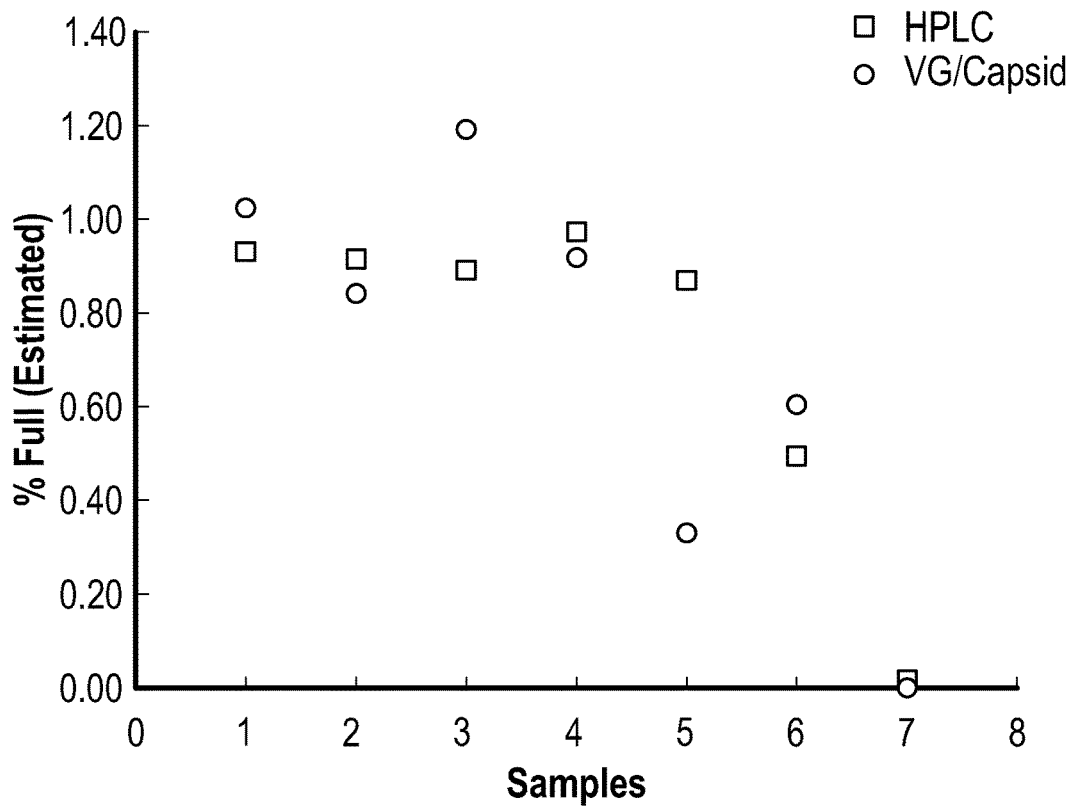

FIG. 2 is a graph showing the comparison and correlation of the percent of full capsids calculated by HPLC vs. vector genome to capsid particle (VG/Capsid) ratio.

Figure 3:
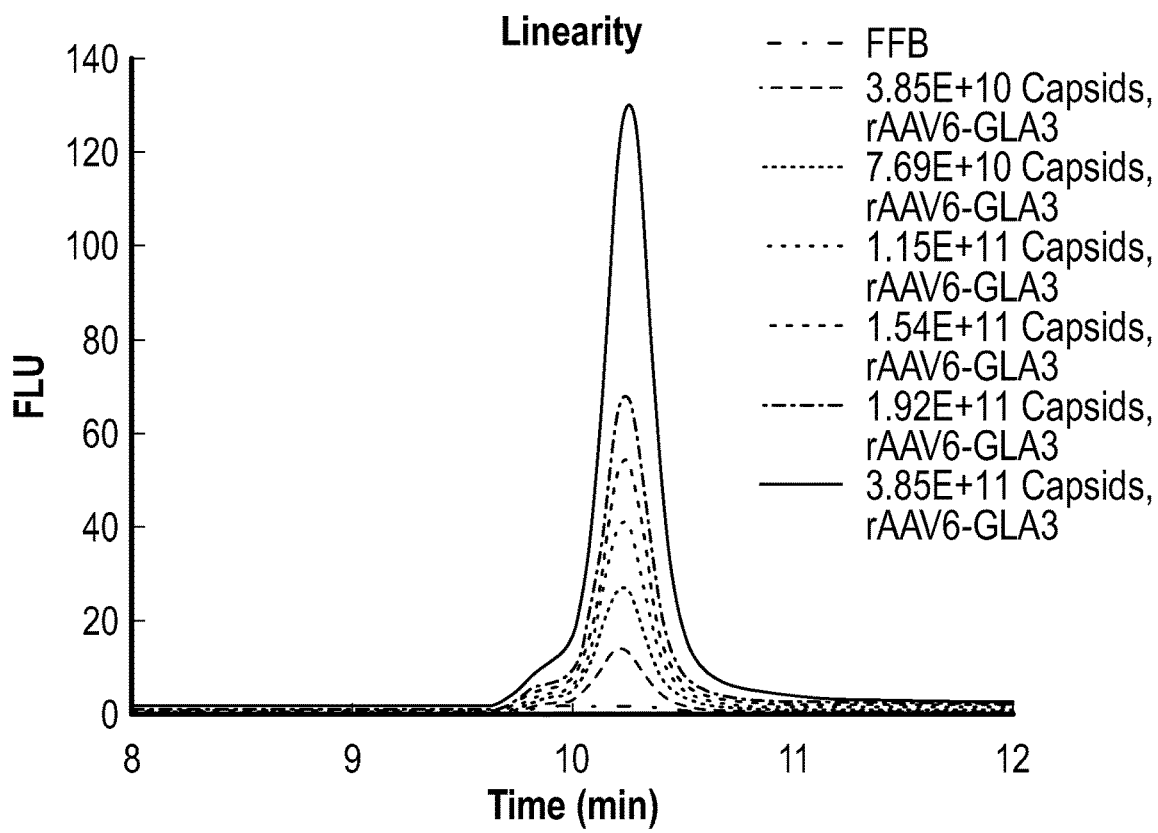

FIG. 3 is a stacked HPLC chromatogram showing the linearity of peak areas of full capsids and varied injection volume for the same sample.

Figure 4:
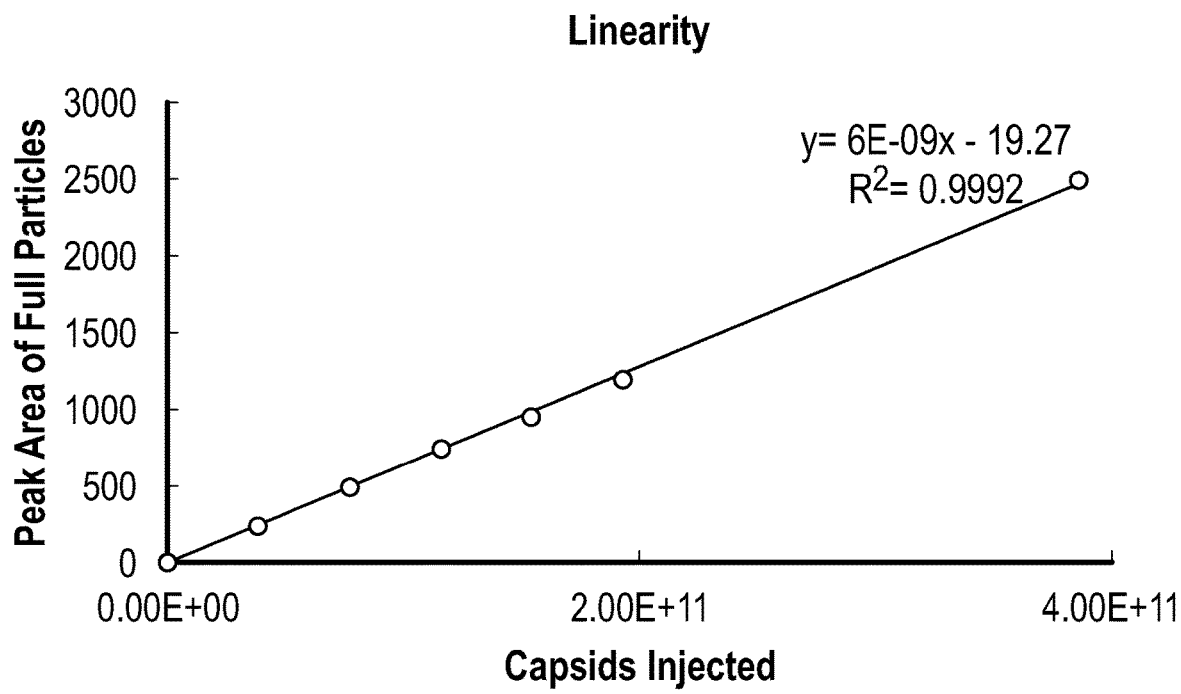

FIG. 4 is a graph showing the linearity of peak areas of full capsids and varied injection volume for the same sample analyzed by HPLC.

Figure 5:
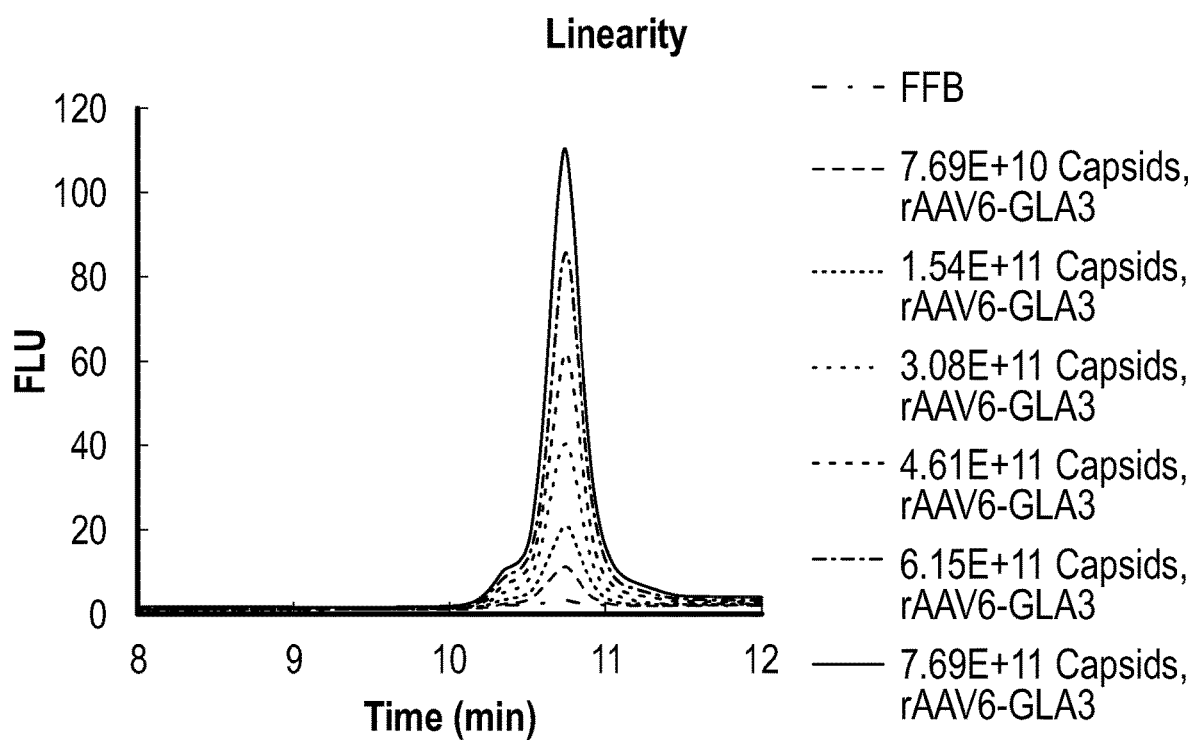

FIG. 5 is a stacked HPLC chromatogram showing the linearity of peak areas of full capsids and varied capsid concentration for the same sample at a constant injection volume.

Figure 6:
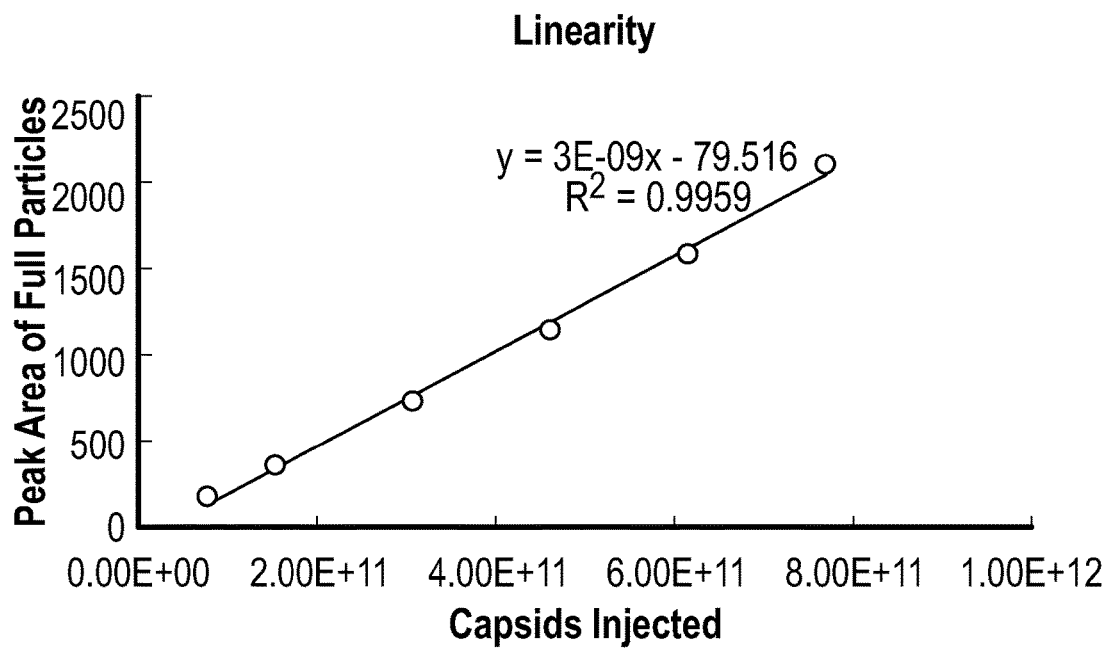

FIG. 6 is a graph showing the linearity of peak area of full capsids and variable capsid concentrations for the same sample measured by HPLC analysis at a constant injection volume.

Figure 7:
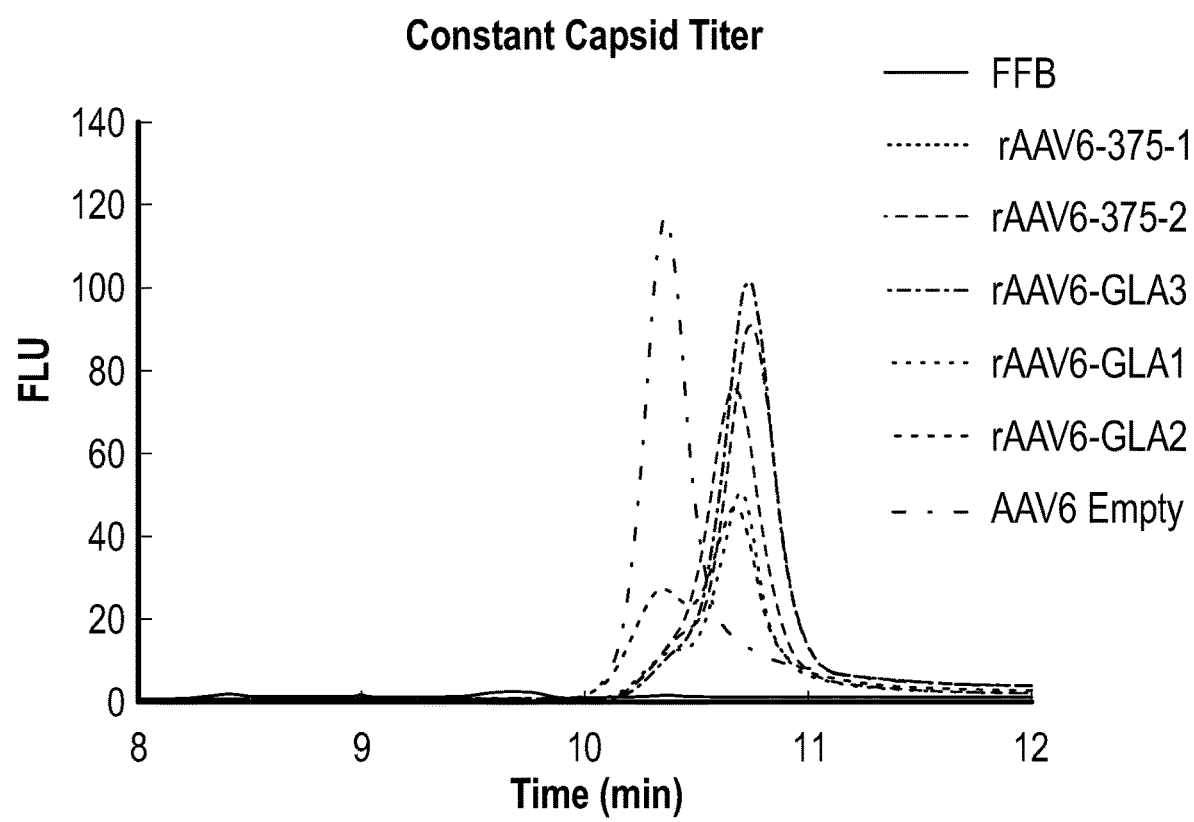

FIG. 7 is an HPLC chromatogram showing peak separation of different rAAV samples with normalized capsid concentrations and an AAV empty sample. rAAV6-375-1: recombinant AAV6 carrying an alpha-L-iduronidase (IDUA) transgene. rAAV6-375-2: a different production batch of the recombinant AAV6 carrying an IDUA transgene. rAAV6-GLA1: recombinant AAV6 carrying a GLA expression cassette different from that in rAAV6-GLA2 or 3.

Figure 8:
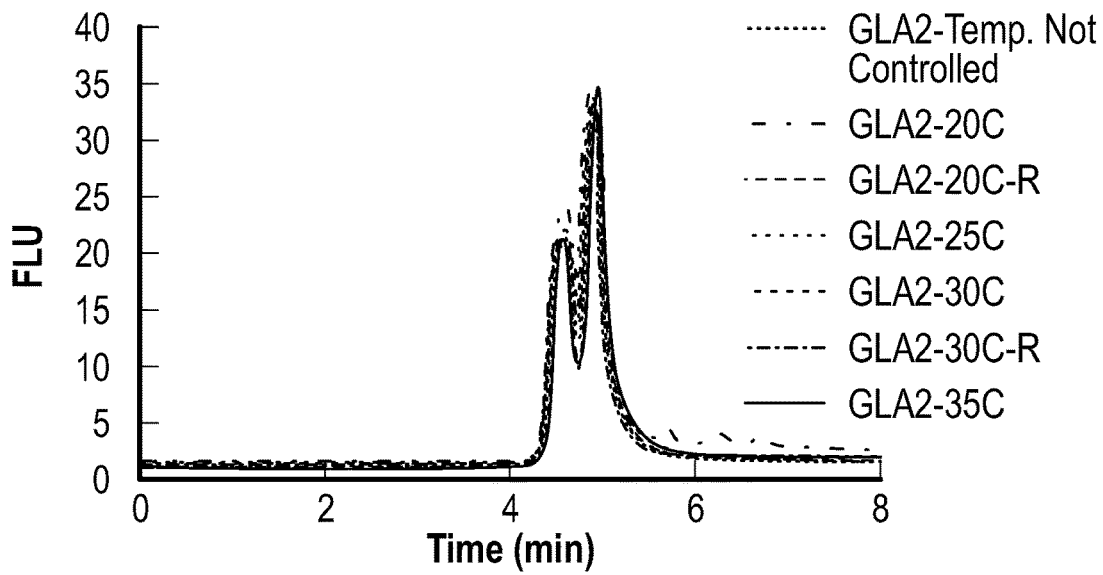

FIG. 8 is an HPLC chromatogram showing the effect of column temperature on peak separation and retention time for Full rAAV6-GLA2 ("GLA2") capsid samples.

Figure 9A:
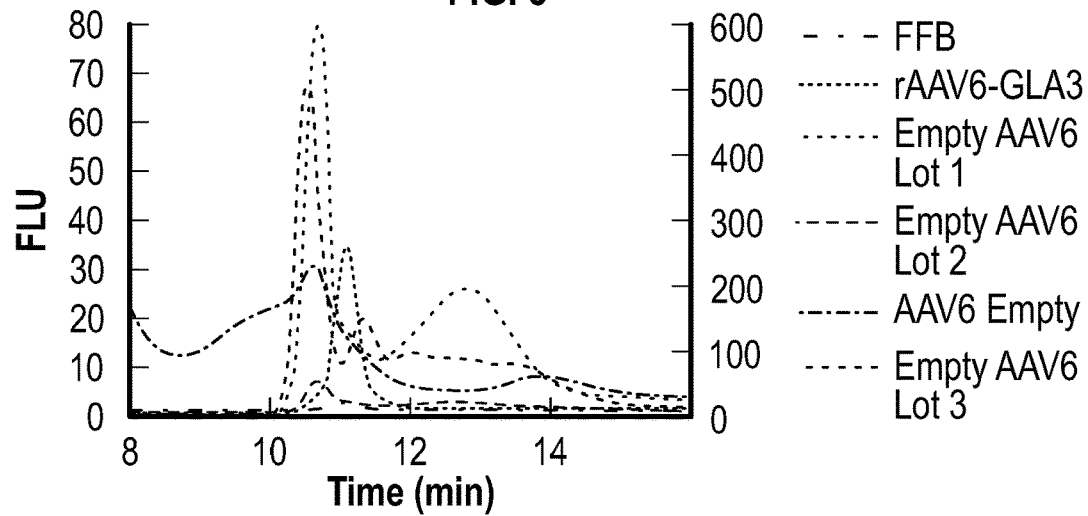
Figure 9B:
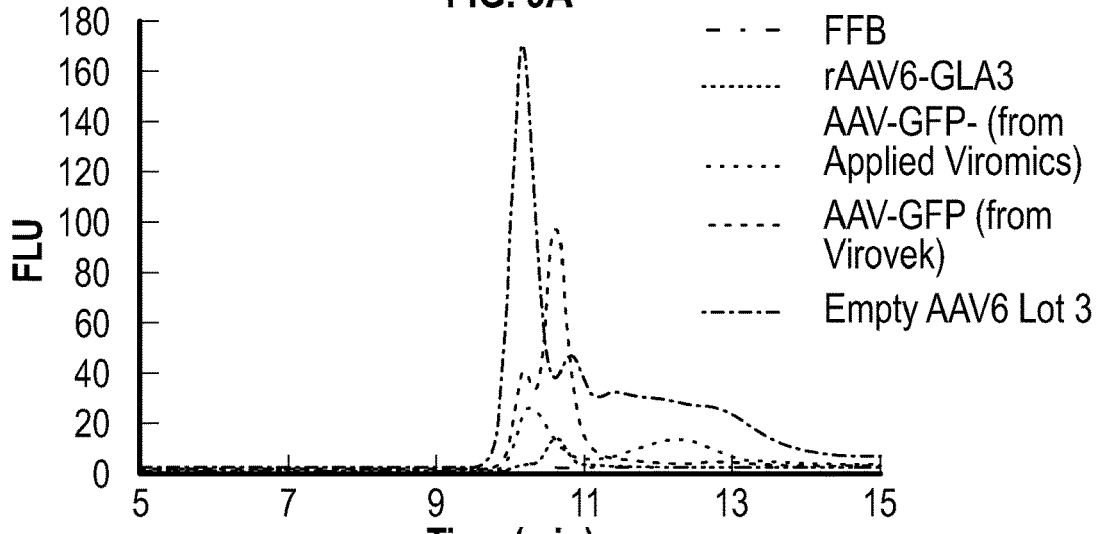

FIGS. 9A and 9B are HPLC chromatograms comparing empty and full peak separation and retention time of AAV and rAAV samples from different commercial vendors. Samples include Empty AAV6 Lot1, Empty AAV6 Lot2, and Empty AAV6 Lot3.

Figure 10:
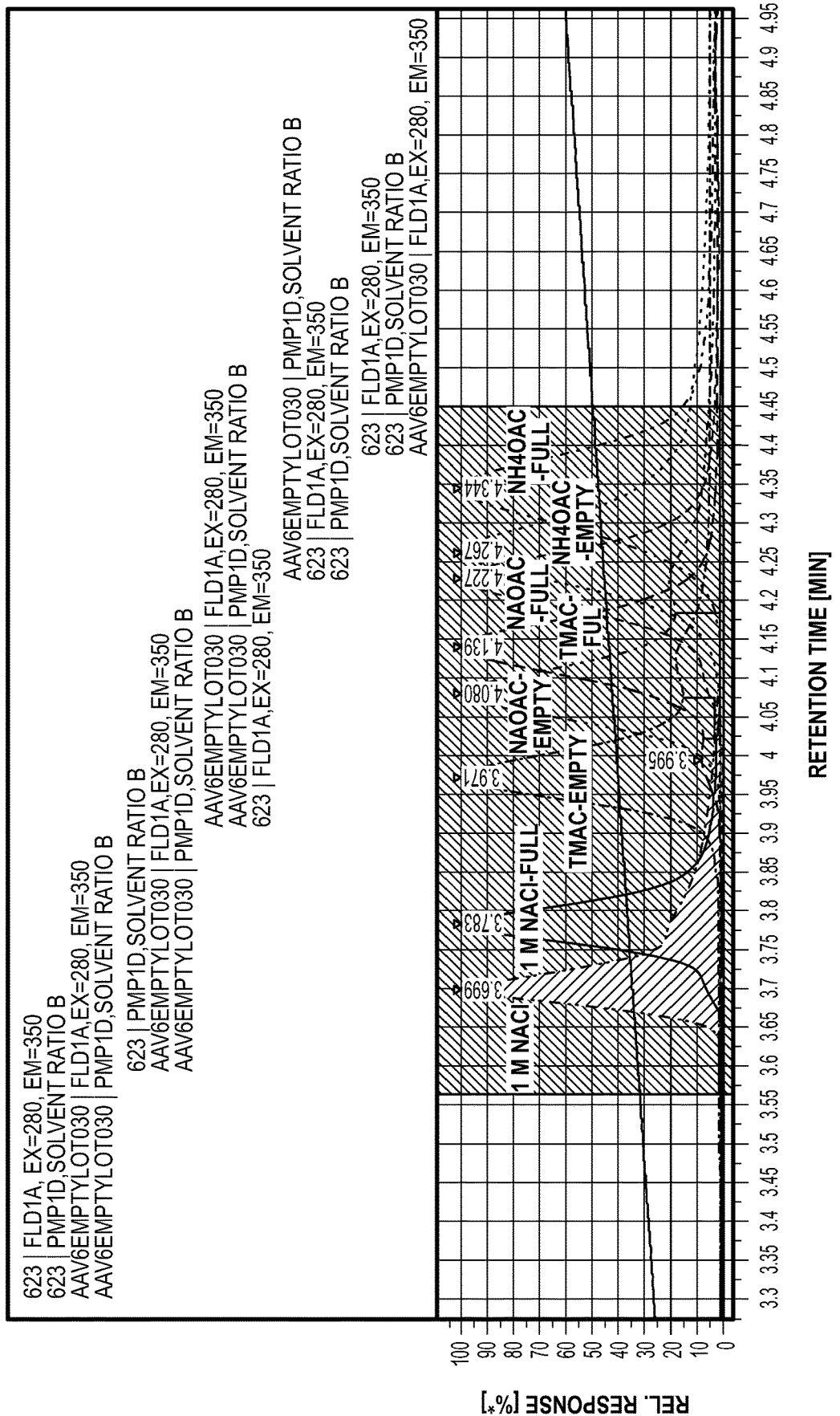

FIG. 10 is an HPLC chromatogram comparing the retention times of samples rAAV6-GLA3 and AAV6-030 [empty AAV6 Lot 030] using four different elution buffers.

Figure 11A:
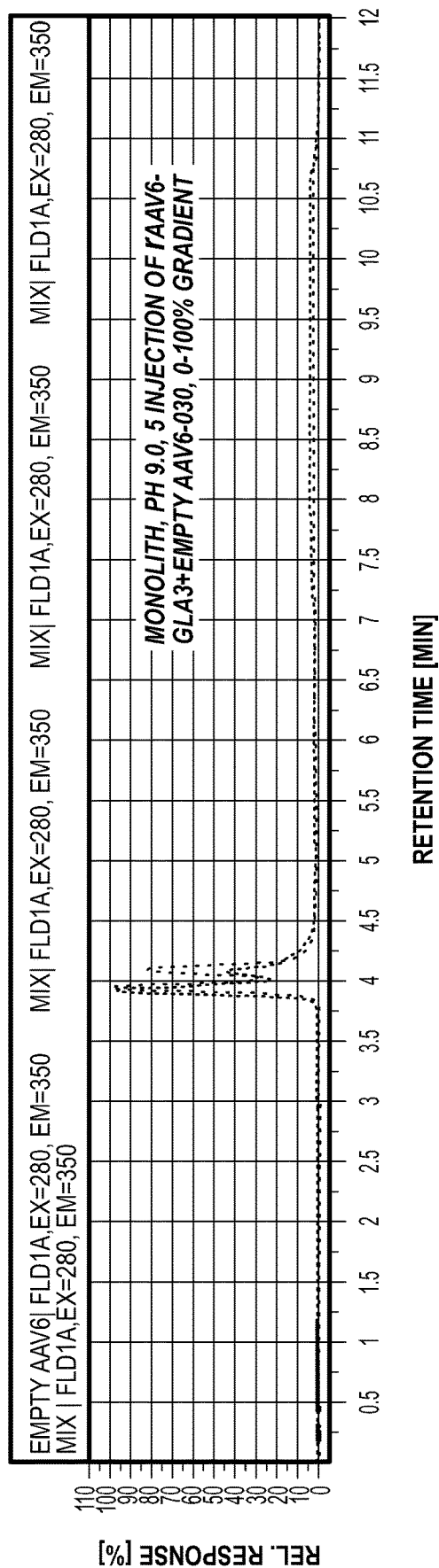

FIG. 11A is an HPLC chromatogram showing HPLC results for consecutive injections of a mixed Full rAAV6-GLA3 and Empty AAV6-030 sample with an elution buffer comprising TMAC run at a gradient of about 0-100%.

Figure 11B:
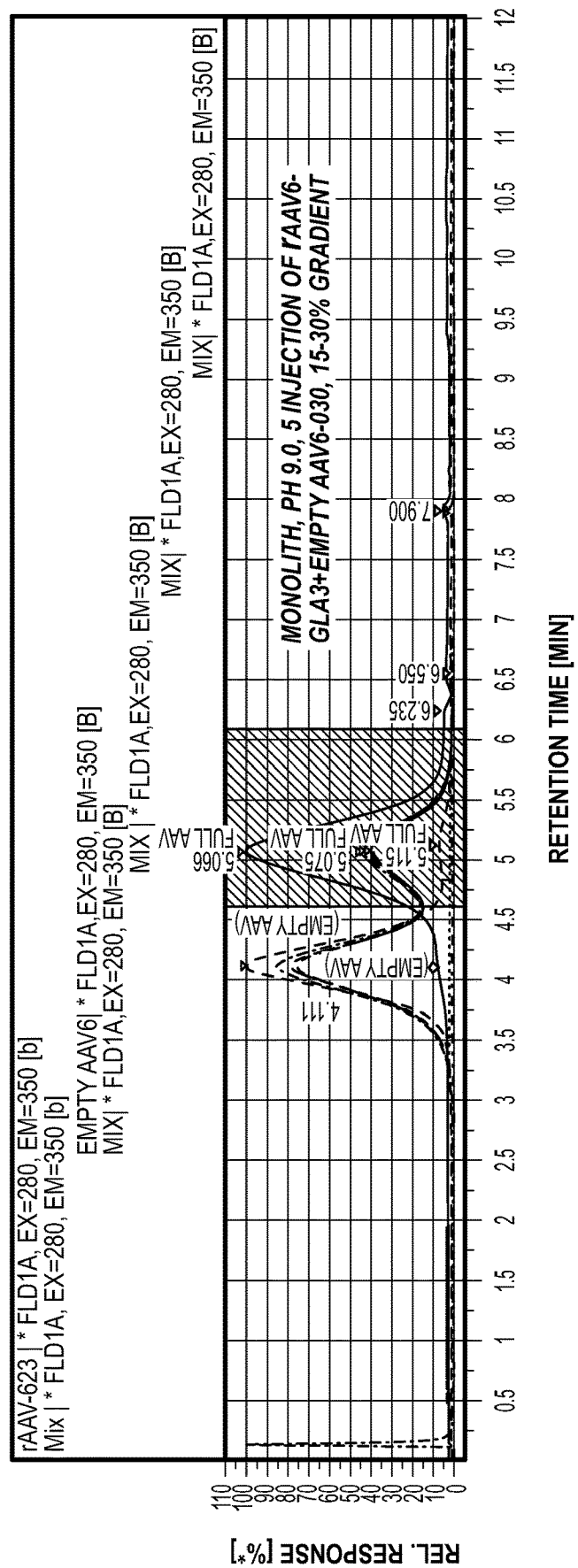

FIG. 11B is an HPLC chromatogram showing HPLC results for consecutive injections of a mixed Full rAAV6-GLA3 and Empty AAV6-030 sample with an elution buffer comprising TMAC run at a gradient of about 15-30%.

Figure 11C:
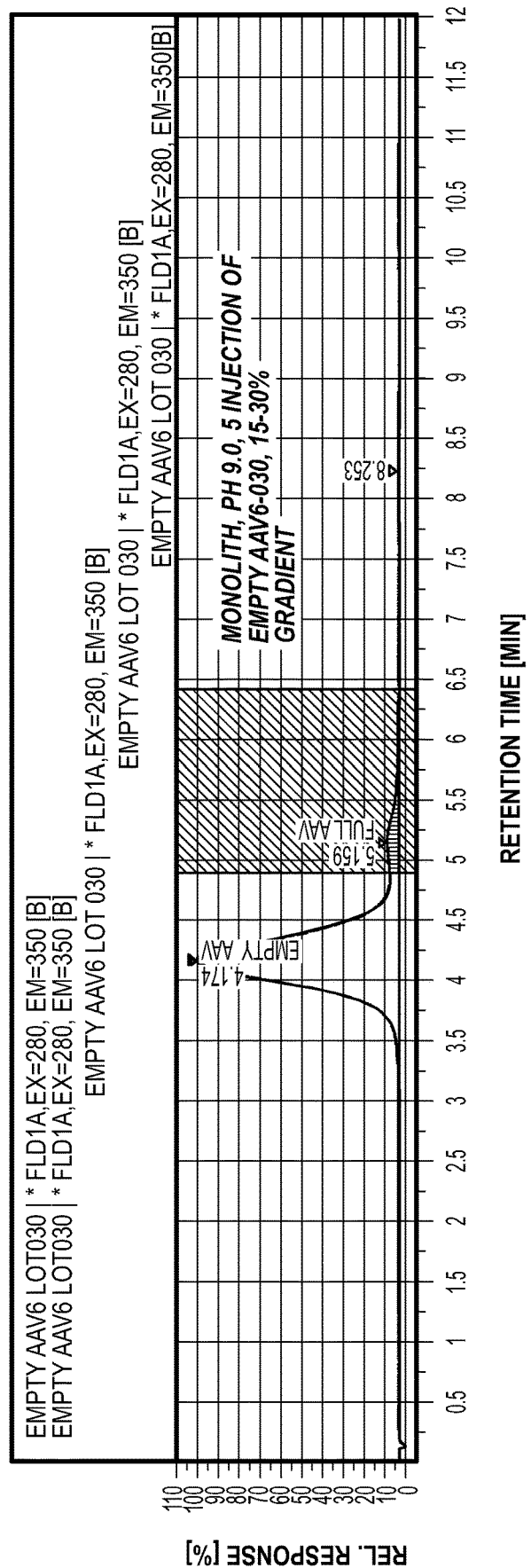

FIG. 11C is an HPLC chromatogram showing results for consecutive injections of an Empty AAV6-030 sample with an elution buffer comprising TMAC run at a gradient of about 15-30%.

Figure 12A:
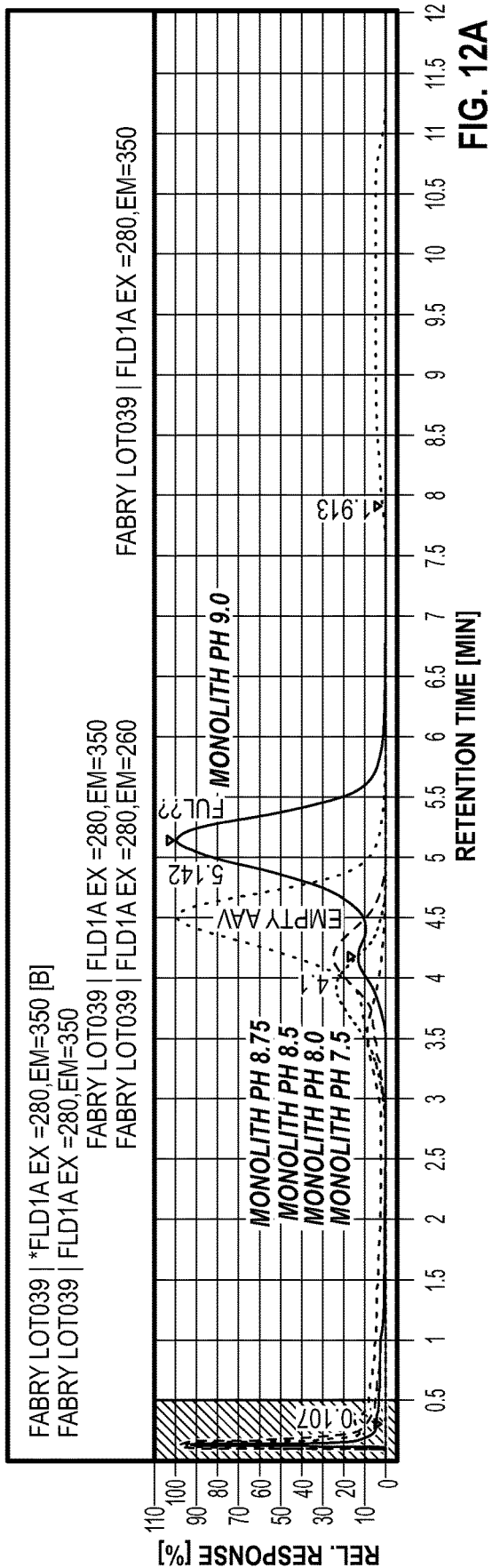

FIG. 12A is an HPLC chromatogram showing peak separation and retention time results for Full rAAV6-GLA3 and Empty AAV6-030 samples run on a monolith HPLC column using an elution buffer comprising TMAC at various pH levels.

Figure 12B:
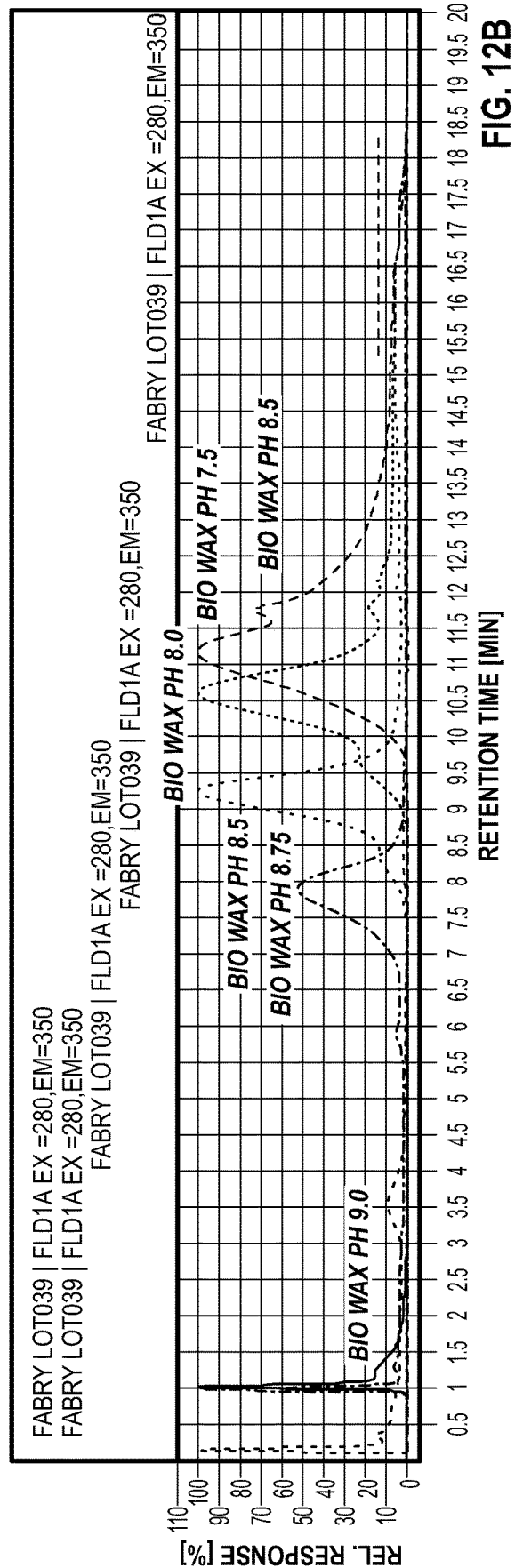

FIG. 12B is an HPLC chromatogram showing peak separation and retention time results for Full rAAV6-GLA3 and Empty AAV6-030 samples run on a weak anionic exchange (WAX) HPLC column using an elution buffer comprising TMAC at various pH levels.

Figure 13:
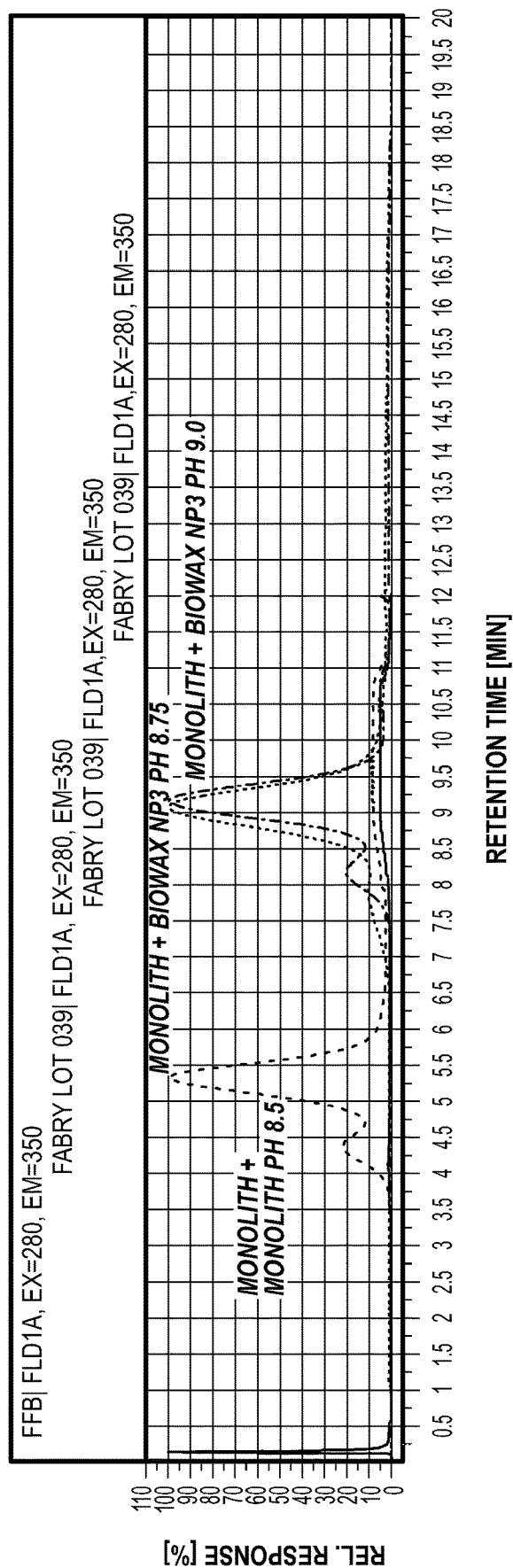

FIG. 13 is an HPLC chromatogram showing peak separation and retention time results for Full rAAV6-GLA3 and Empty AAV6-030 samples run on AAV monolith and weak anionic exchange (WAX) HPLC columns in a tandem configuration using an elution buffer comprising TMAC at various pH levels.

Figure 14:
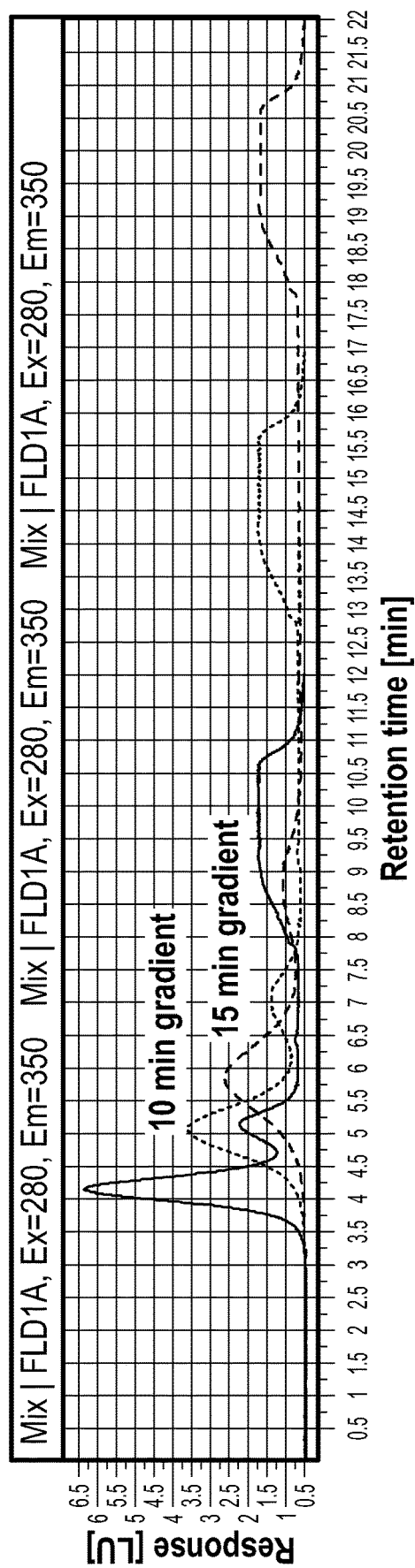

FIG. 14 is an HPLC chromatogram showing peak separation and retention time results for a mixed Full rAAV6-GLA3 and Empty AAV6-030 sample using shallow gradients (longer HPLC run times) of about 10 minutes and 15 minutes.

Figure 15:
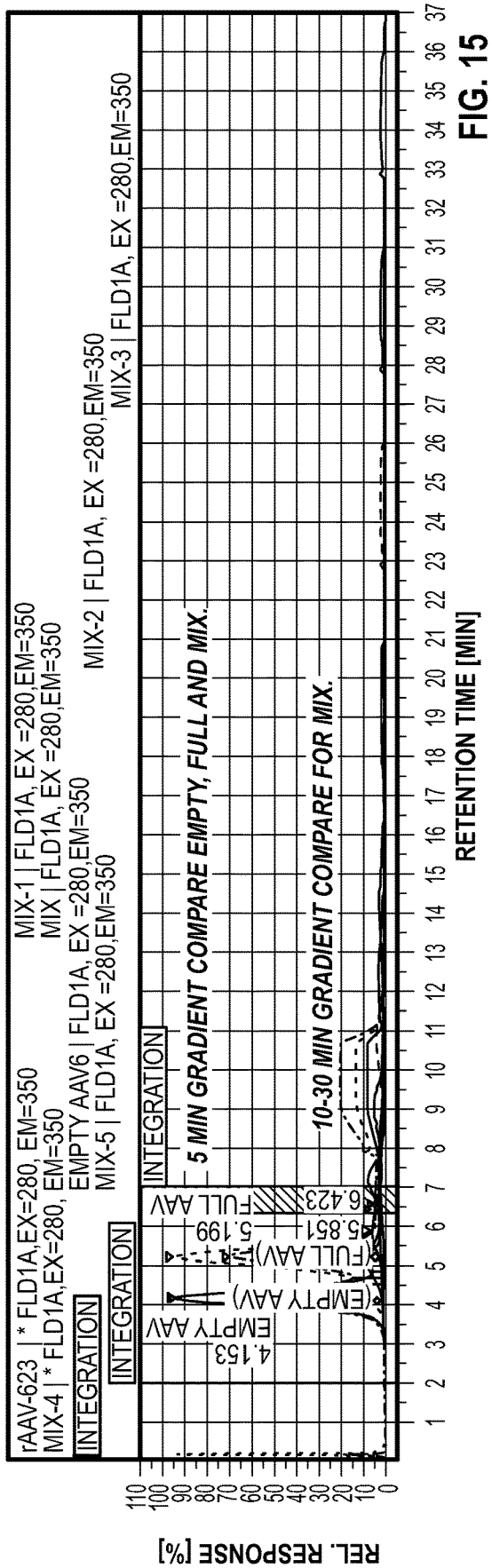

FIG. 15 is an HPLC chromatogram showing peak separation and retention time results for a mixed Full rAAV6-GLA3 and Empty AAV6-030 sample using shallow gradients of elution buffer of about 10, 15, 20, 25, and 30 minutes, compared to results for Full rAAV6-GLA3 and Empty AAV6-030 samples using an elution buffer run time gradient of about 5 minutes.

Figure 16:
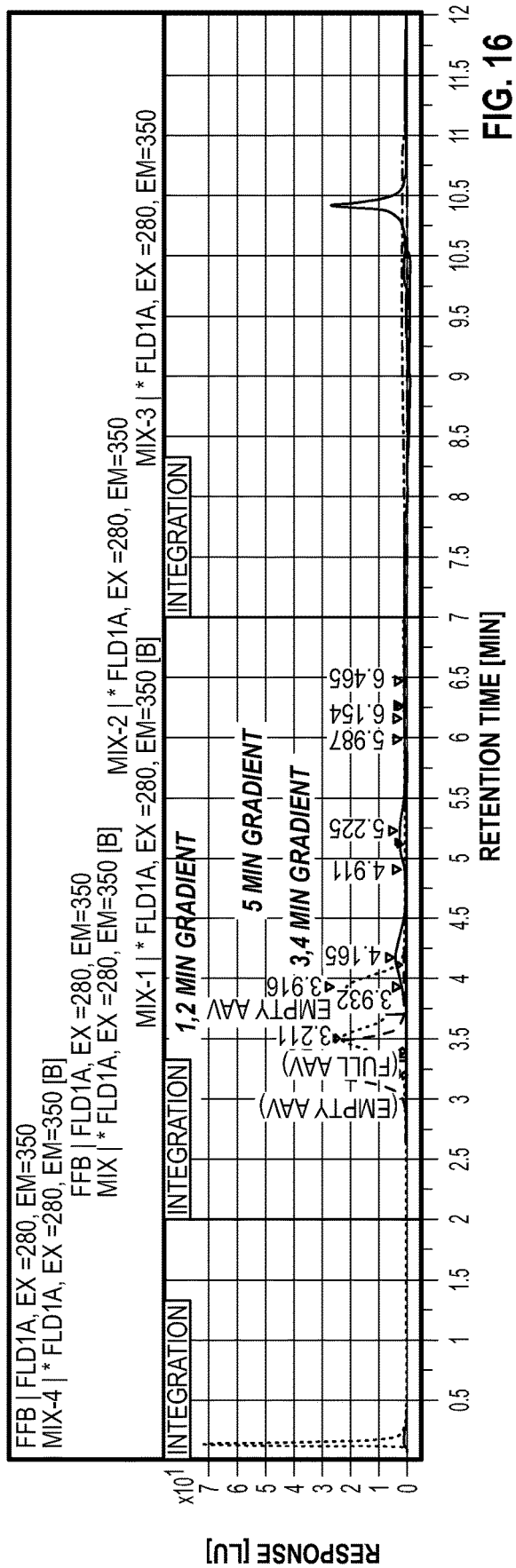

FIG. 16 is an HPLC chromatogram showing peak separation and retention time results for a mixed Full rAAV6-GLA3 and Empty AAV6-030 sample using run time gradients of elution buffer of about 1, 2, 3, 4, and 5 minutes.

FIG. 17 is an HPLC chromatogram showing peak separation and retention time results for a sample comprising, Full rAAV6-GLA3, using an elution buffer comprising TMAC run at gradients of about 15%-30% or 15%-35% with an isocratic hold at about 17% or 18%.

FIG. 18 is an HPLC chromatogram showing peak separation and retention time results for a mixed Full rAAV6-GLA3 and Empty AAV6-030 sample, using an elution buffer comprising TMAC run at gradients of about 15%-30% or 15%-35% with an isocratic hold at about 18% or 19%.

Figure 19:
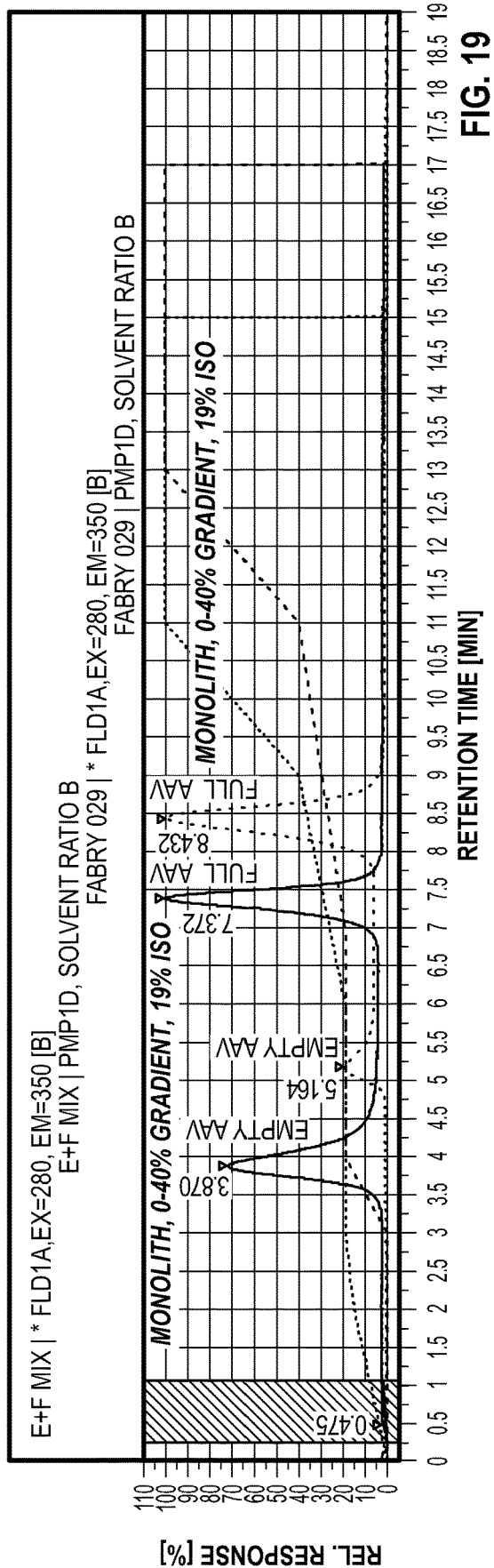

FIG. 19 is an HPLC chromatogram showing peak separation and retention time results for a mixed Full rAAV6-GLA3 and Empty AAV6-030 sample, using an elution buffer comprising TMAC run at a gradient of about 0%-40% with an isocratic hold at about 19%.

Figure 20:
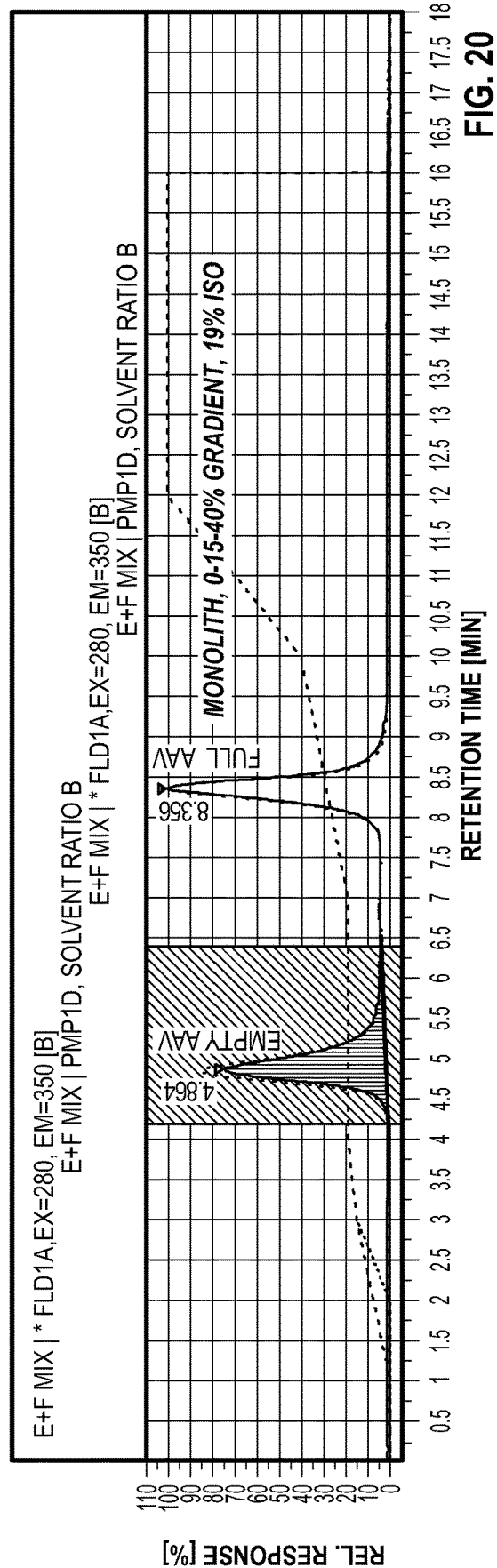

FIG. 20 is an HPLC chromatogram showing peak separation and retention time results for a mixed Full rAAV6-GLA3 and Empty AAV6-030 sample, using an elution buffer comprising TMAC run at a gradient of about 0%-40% with an isocratic hold at about 19%.

Figure 21:
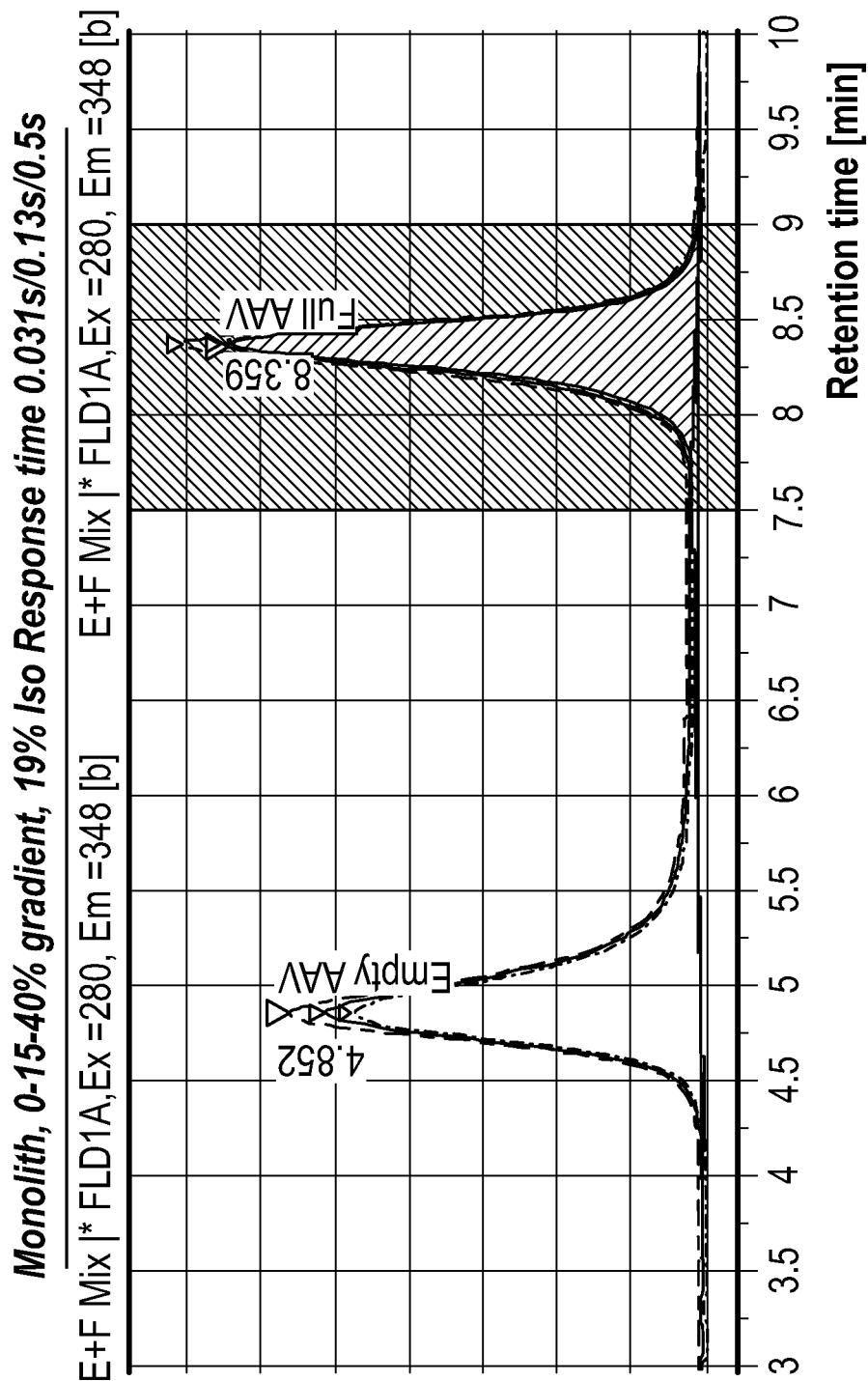

FIG. 21 is an HPLC chromatogram showing peak separation and retention time results for a mixed Full rAAV6-GLA3 and Empty AAV6-030 sample, using an elution buffer comprising TMAC run at a gradient of about 0%-40% with an isocratic hold at about 19% and response time of about 0.031 s/0.13 s/0.5 s.

Figure 22:
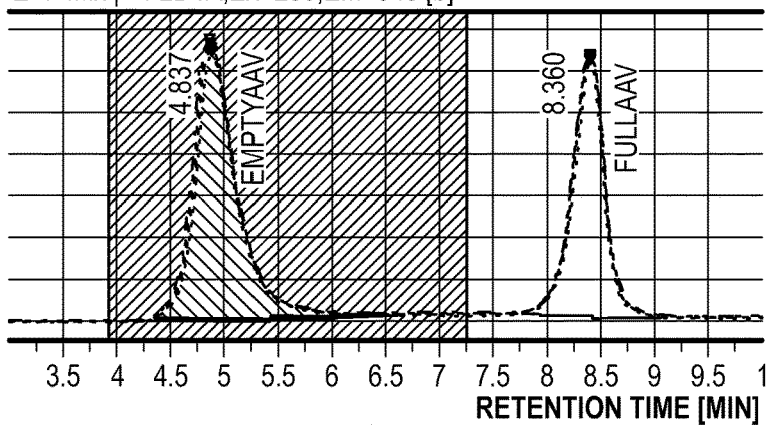

FIG. 22 is an HPLC chromatogram showing peak separation and retention time results for a mixed Full rAAV6-GLA3 and Empty AAV6-030 sample, using an elution buffer comprising TMAC run at gradients of about 0%-40%, 5%-40%, or 10%-40% with an isocratic hold at about 19%.

Figure 23:
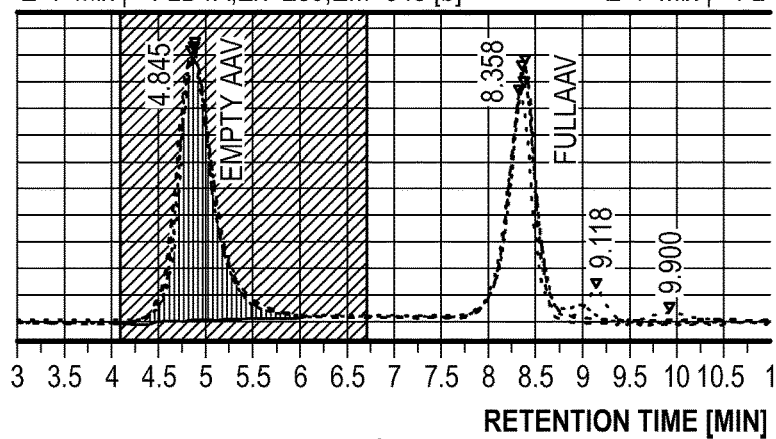

FIG. 23 is an HPLC chromatogram showing peak separation and retention time results for a mixed Full rAAV6-GLA3 and Empty AAV6-030 sample, using an elution buffer comprising TMAC run at gradients of about 5%-40% with an isocratic hold at about 19% and with column temperatures of about 20° C., 25° C., 30° C., or 35° C.

Figure 24:
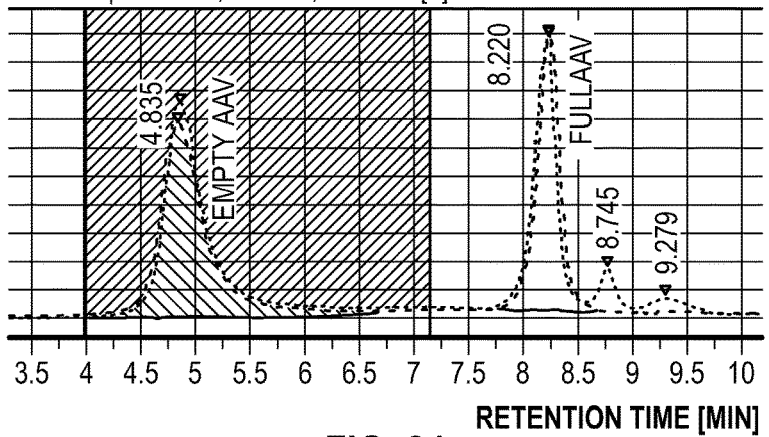

FIG. 24 is an HPLC chromatogram showing peak separation and retention time results for a mixed Full rAAV6-GLA3 and Empty AAV6-030 sample, using an elution buffer comprising TMAC run at gradients of about 5%-50% with an isocratic hold at about 19% and with column temperatures of about 25° C. or 35° C.

Figure 25:
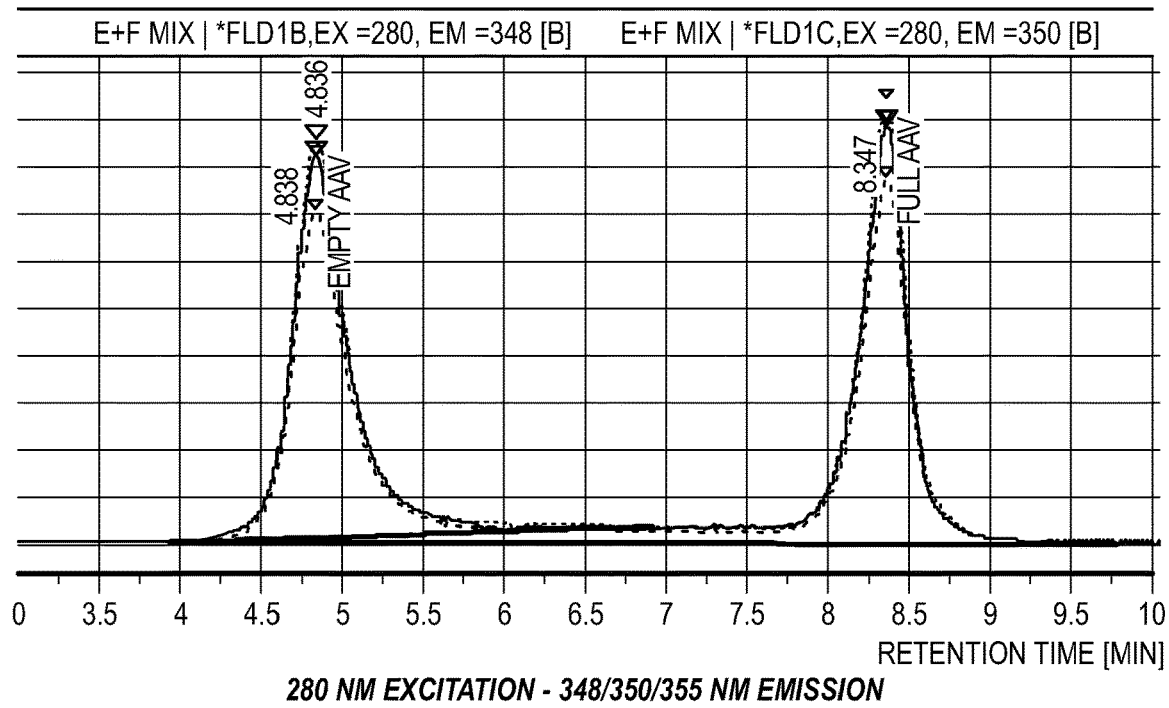

FIG. 25 is an HPLC chromatogram showing peak separation and retention time results for a mixed Full rAAV6-GLA3 and Empty AAV6-030 sample, using an elution buffer comprising TMAC run at gradients of about 0%-40% with an isocratic hold at about 19% and with the detection wavelengths set at 280 nm excitation and 348/350/355 nm emission.

Figure 26:
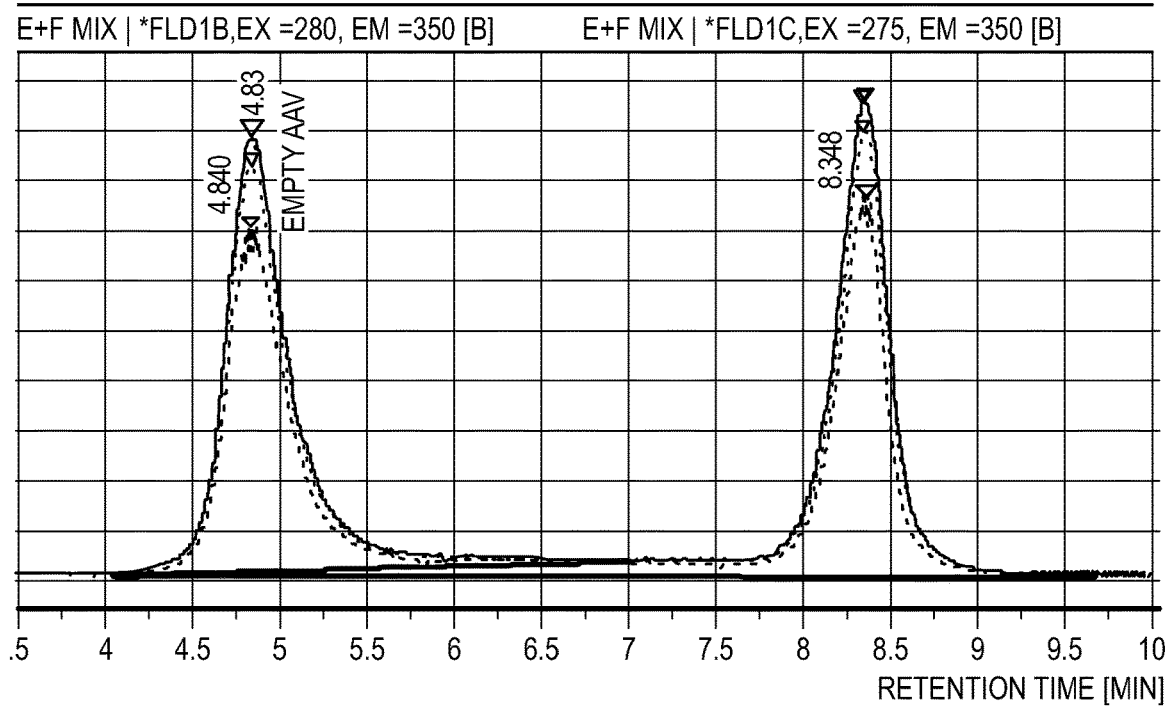

FIG. 26 is an HPLC chromatogram showing peak separation and retention time results for a mixed Full rAAV6-GLA3 and Empty AAV6-030 sample, using an elution buffer comprising TMAC run at a gradient of about 0%-40% with an isocratic hold at about 19% and with the detection wavelengths set at 348 nm excitation and 280/350/355 nm emission.

Figure 27:
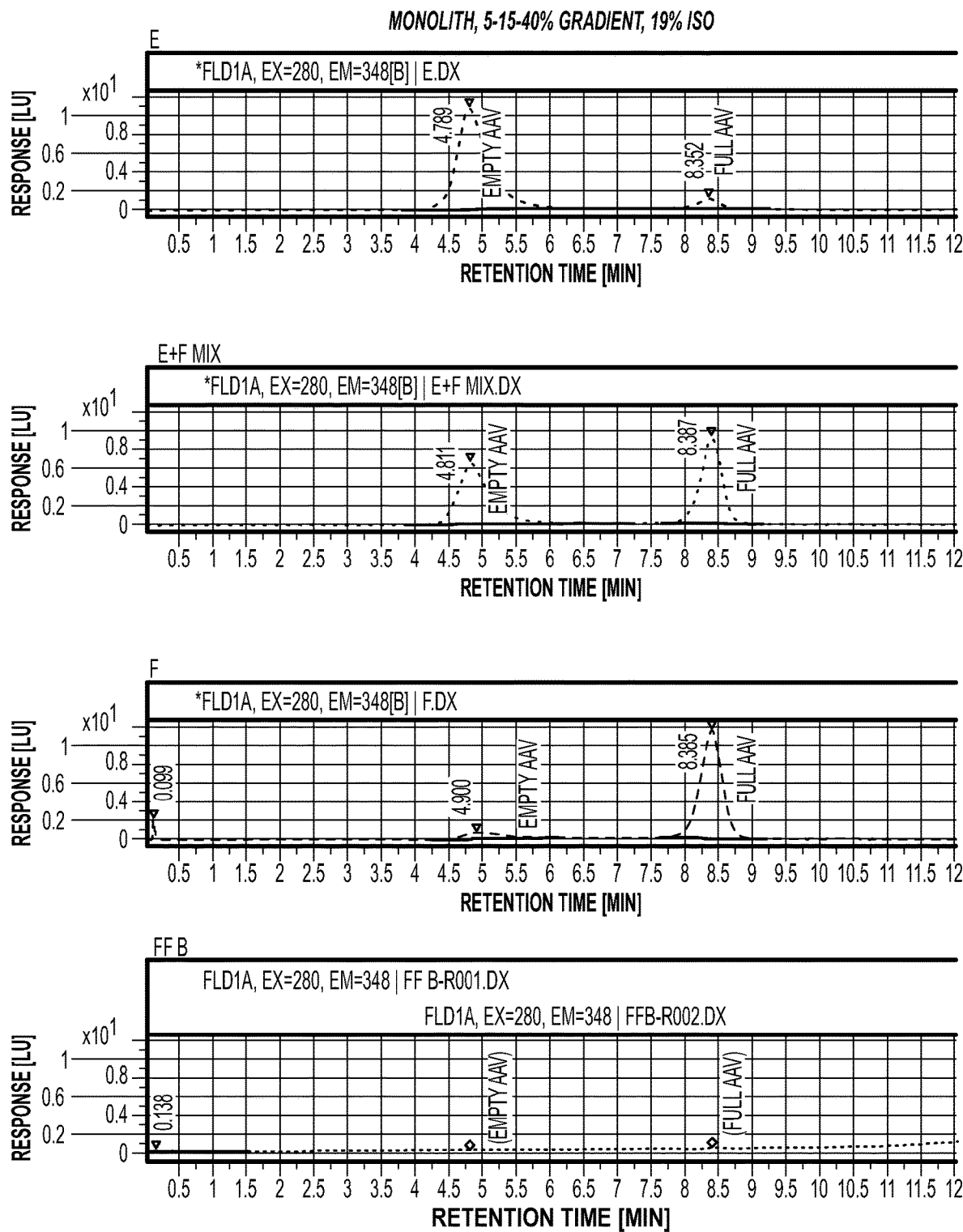
Figure 27:
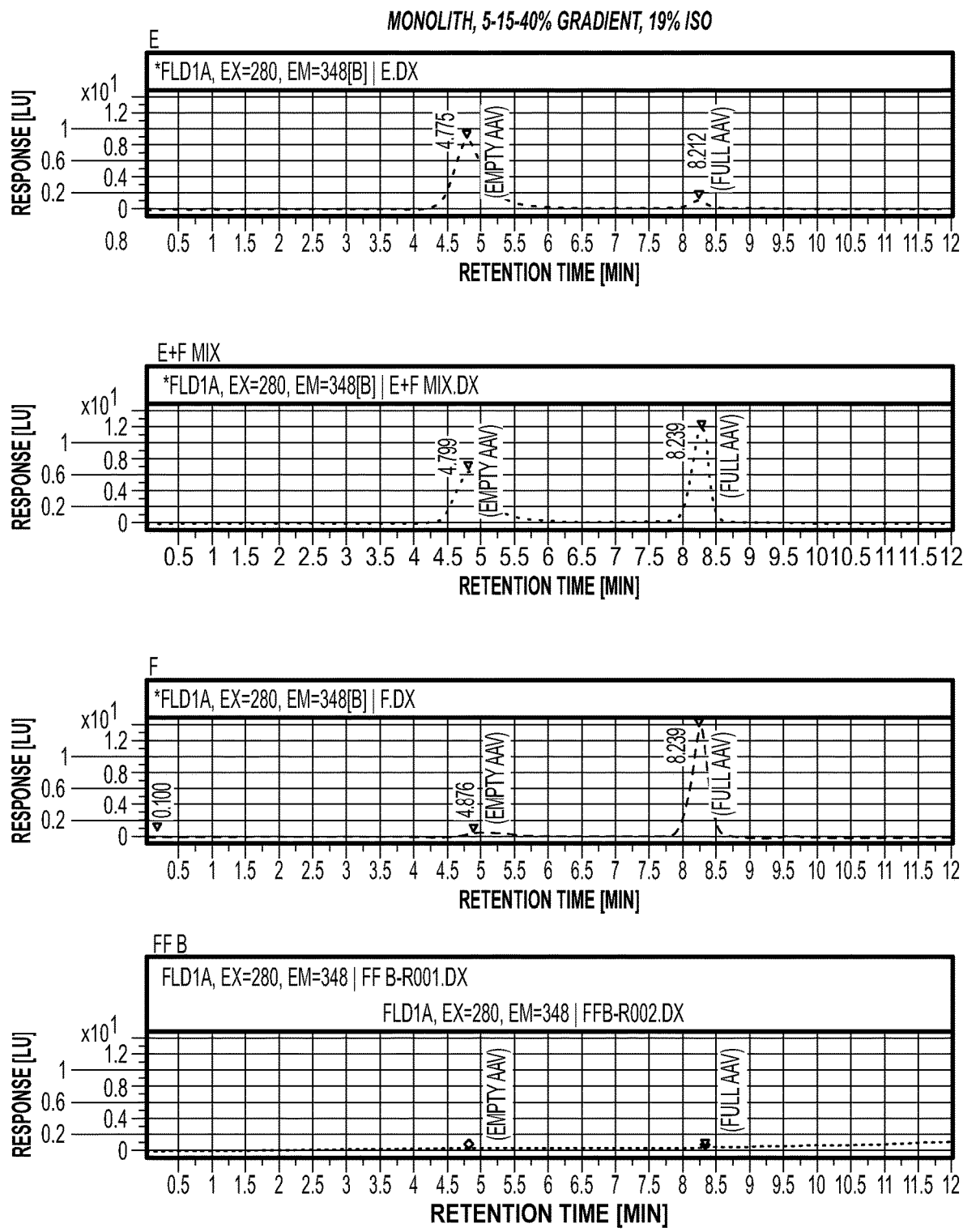

FIG. 27 is a panel of HPLC chromatograms showing comparisons of peak separation and retention time results for formulation buffer (FB), Empty (E), Full (F), and Empty+Full capsid mixed composition samples using an elution buffer comprising TMAC run at gradients of about 5%-40% or about 5%-50% with an isocratic hold at about 19%.

Figure 28A:
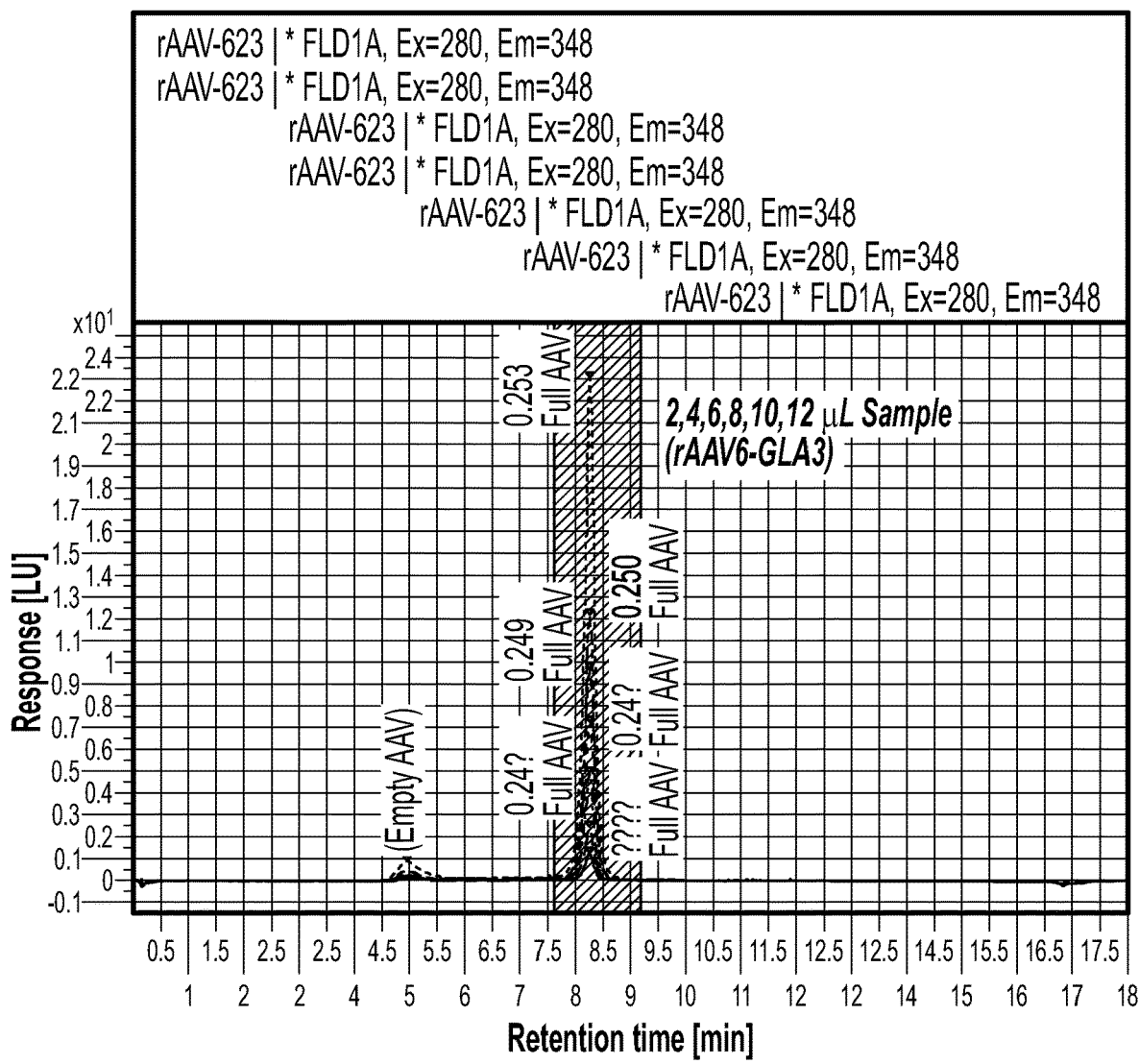
Figure 28B:
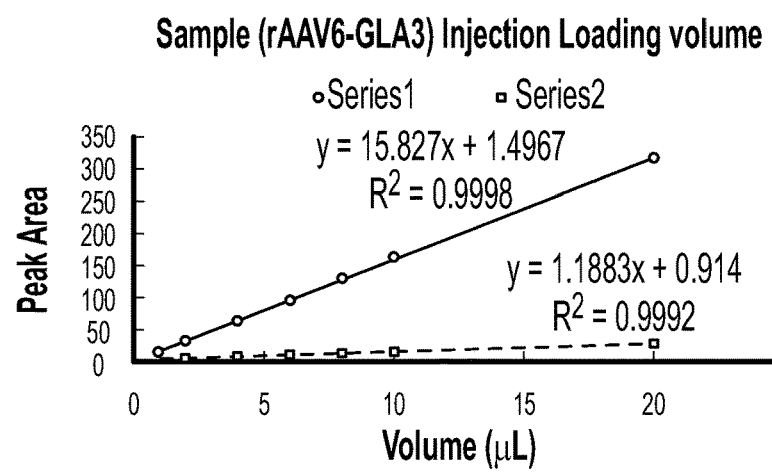

FIGS. 28A and 28B are an HPLC chromatogram and a graph showing the load linearity of peak area for a Full rAAV6-GLA3 sample at about 2, 4, 6, 8, 10, and 20

Figure 29A:
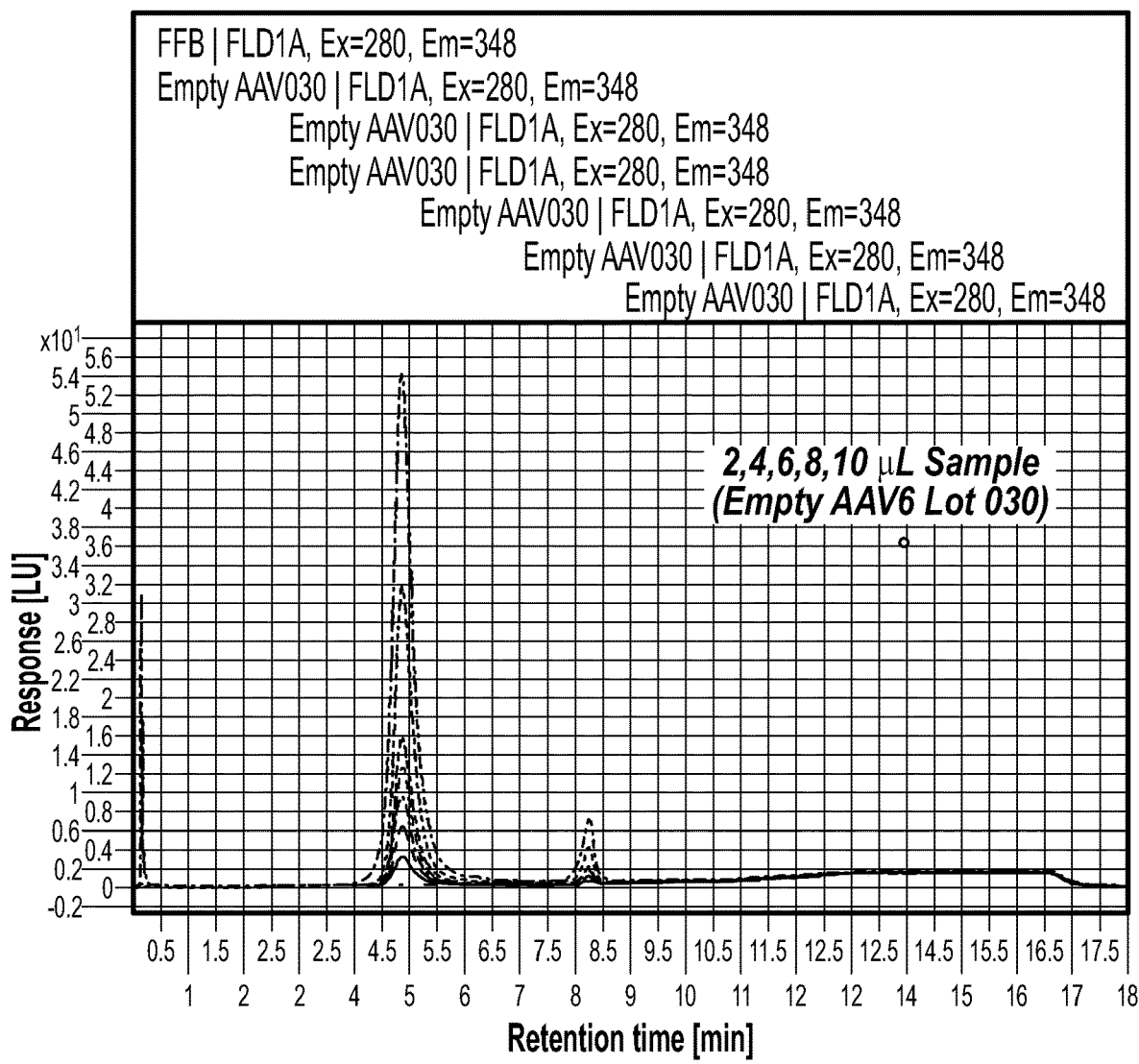
Figure 29B:
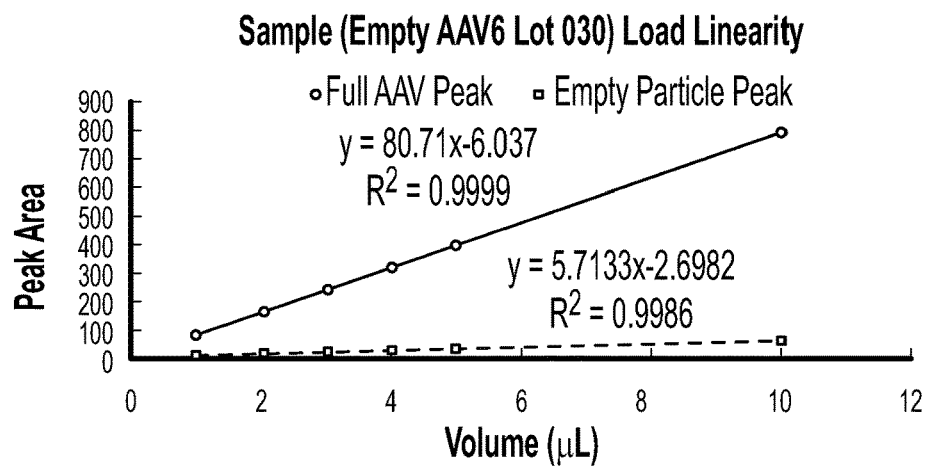

FIGS. 29A and 29B are an HPLC chromatogram and a graph showing the load linearity of peak area for an Empty AAV6-030 sample at about 2, 4, 6, 8, and 10 µl injection volumes.

Figure 30A:
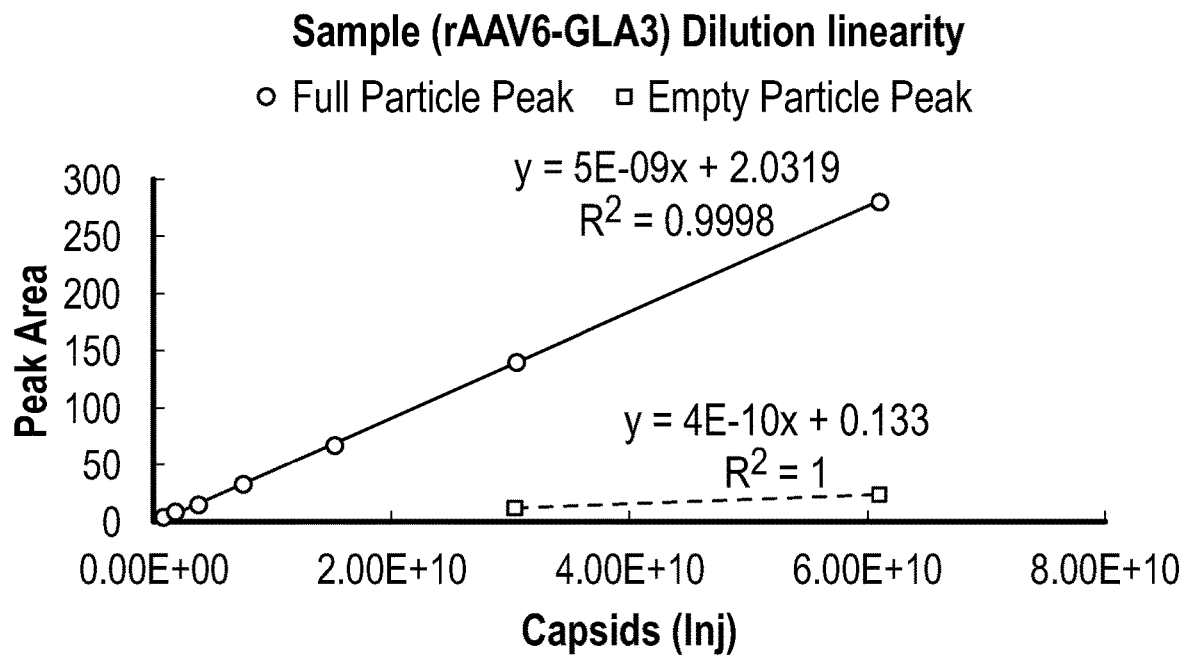
Figure 30B:
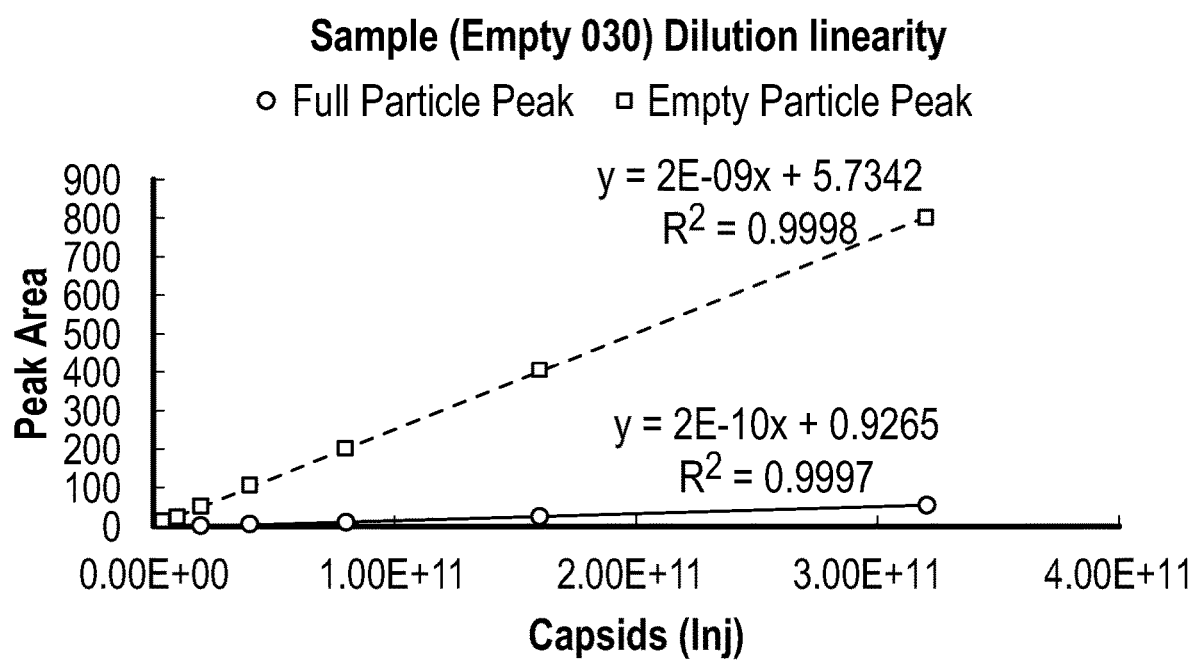

FIGS. 30A and 30B are graphs showing the dilution linearity of peak area for both Full rAAV6-GLA3 and Empty AAV6-030 samples.

Figure 31:
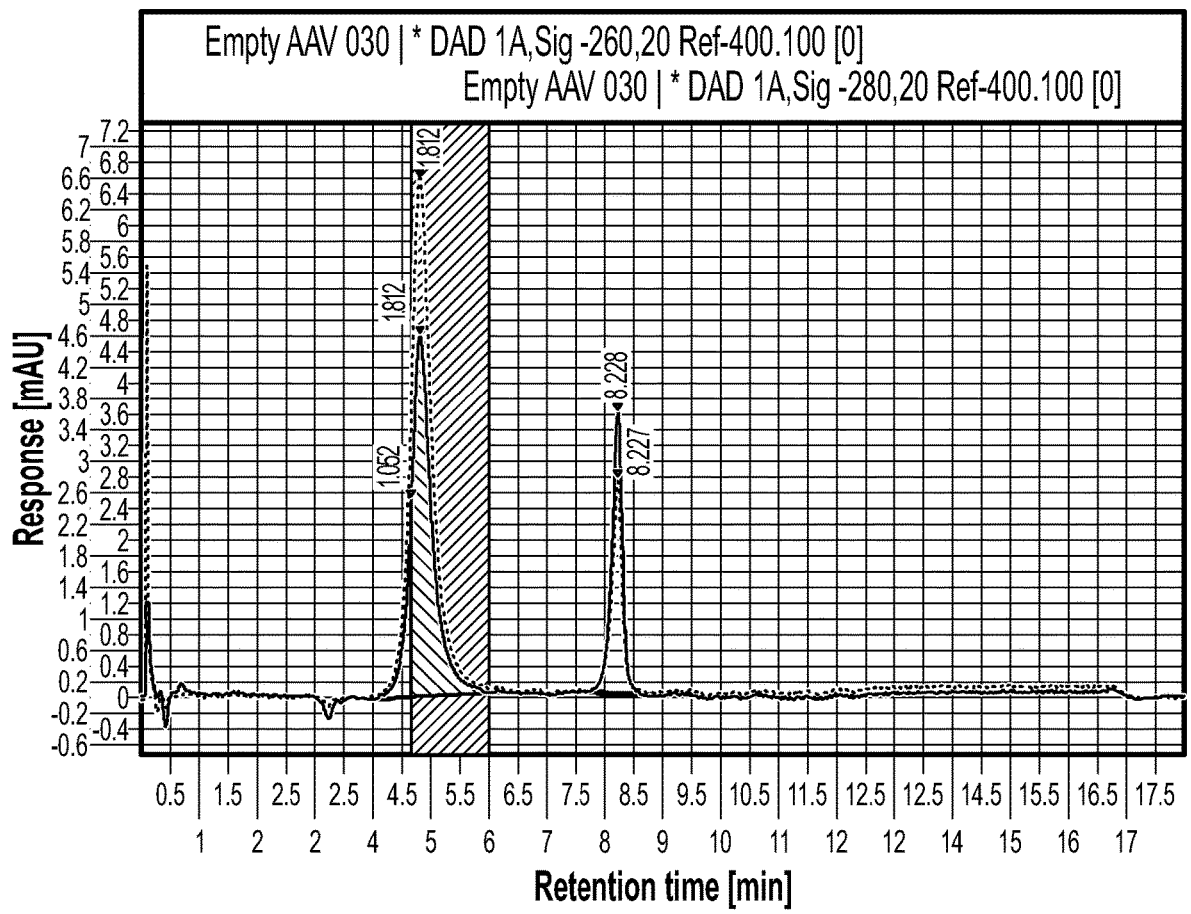

FIG. 31 is an HPLC chromatogram showing UV 260 and 280 nm traces of a mixed sample exhibiting classical 260/280 switch in peak height of empty and full AAV peaks.

Figure 32:
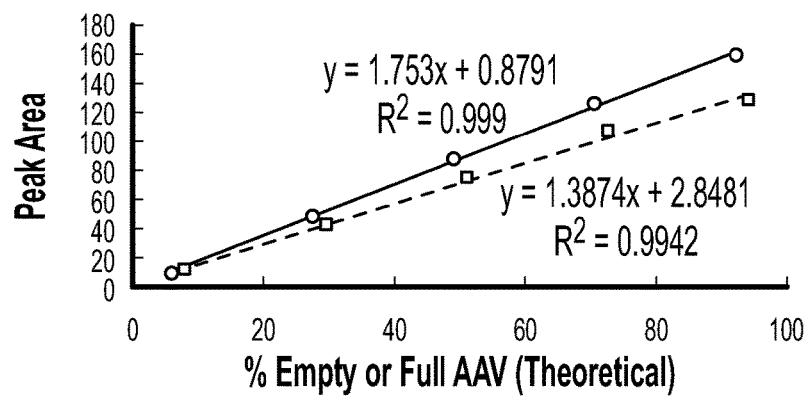

FIG. 32 is a graph showing calibration plots of different mixtures of Full rAAV6-GLA3 and Empty AAV6-030 samples indicating the linear relationship between peak area and capsid concentration.

Figure 33:
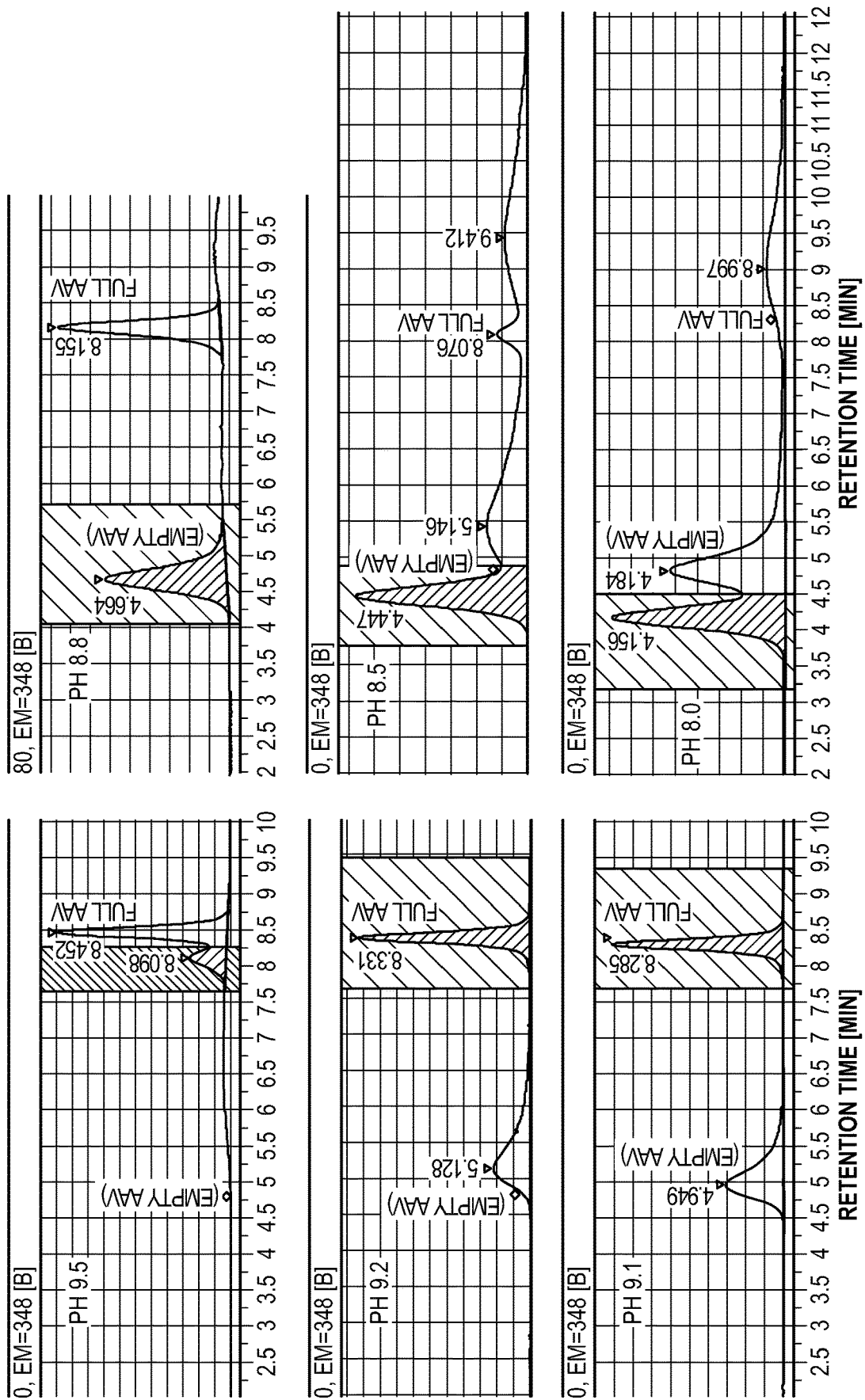

FIG. 33 is a panel of HPLC chromatograms showing peak separation and retention time results for a mixed Full rAAV6-GLA3 and Empty AAV6-030 sample, using an elution buffer comprising TMAC run at various pH values.

Figure 34:
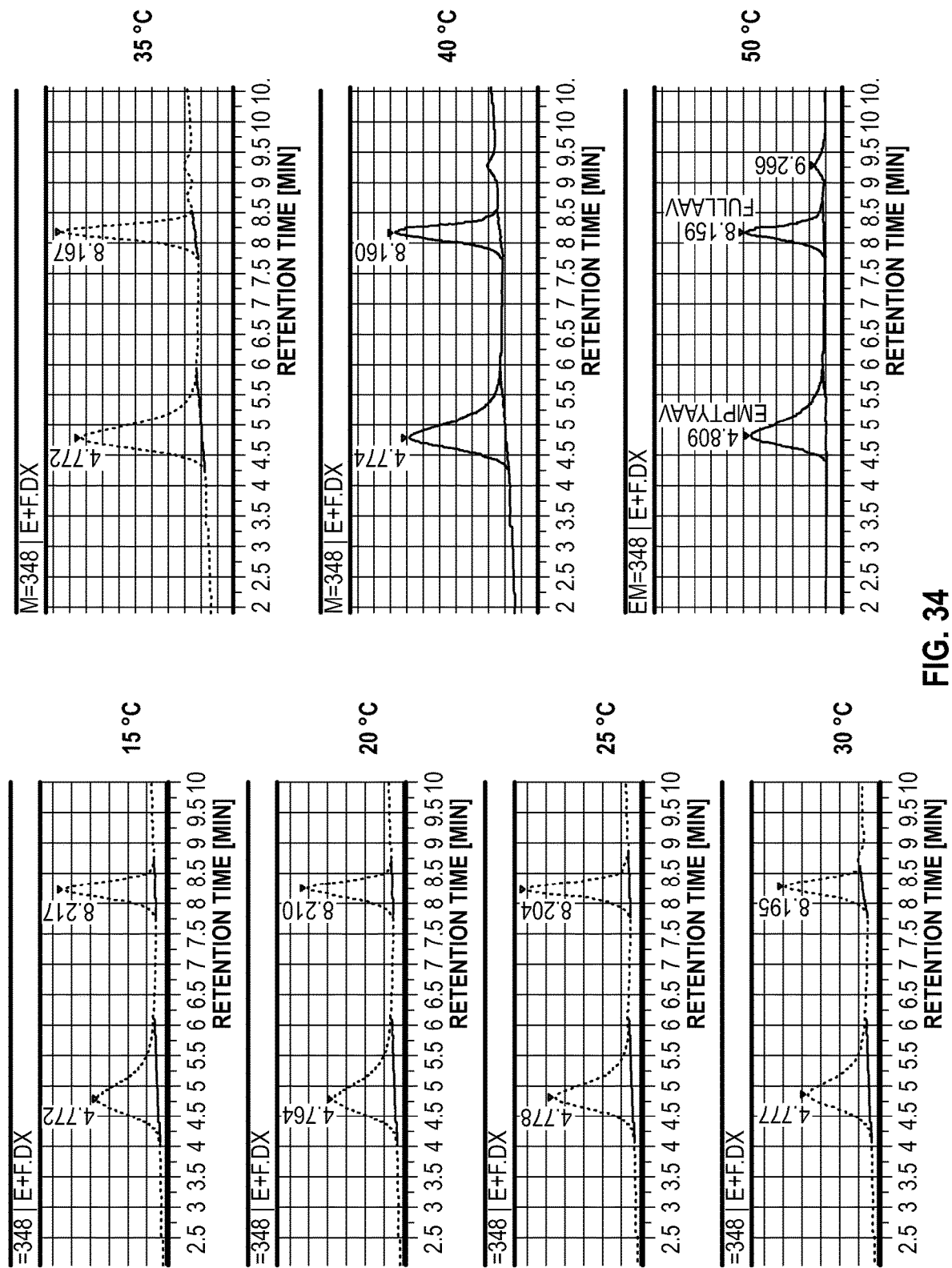

FIG. 34 is a panel of HPLC chromatograms showing peak separation and retention time results for a mixed Full rAAV6-GLA3 and Empty AAV6-030 sample, using an elution buffer comprising TMAC run at various column temperatures.

Figure 35A:
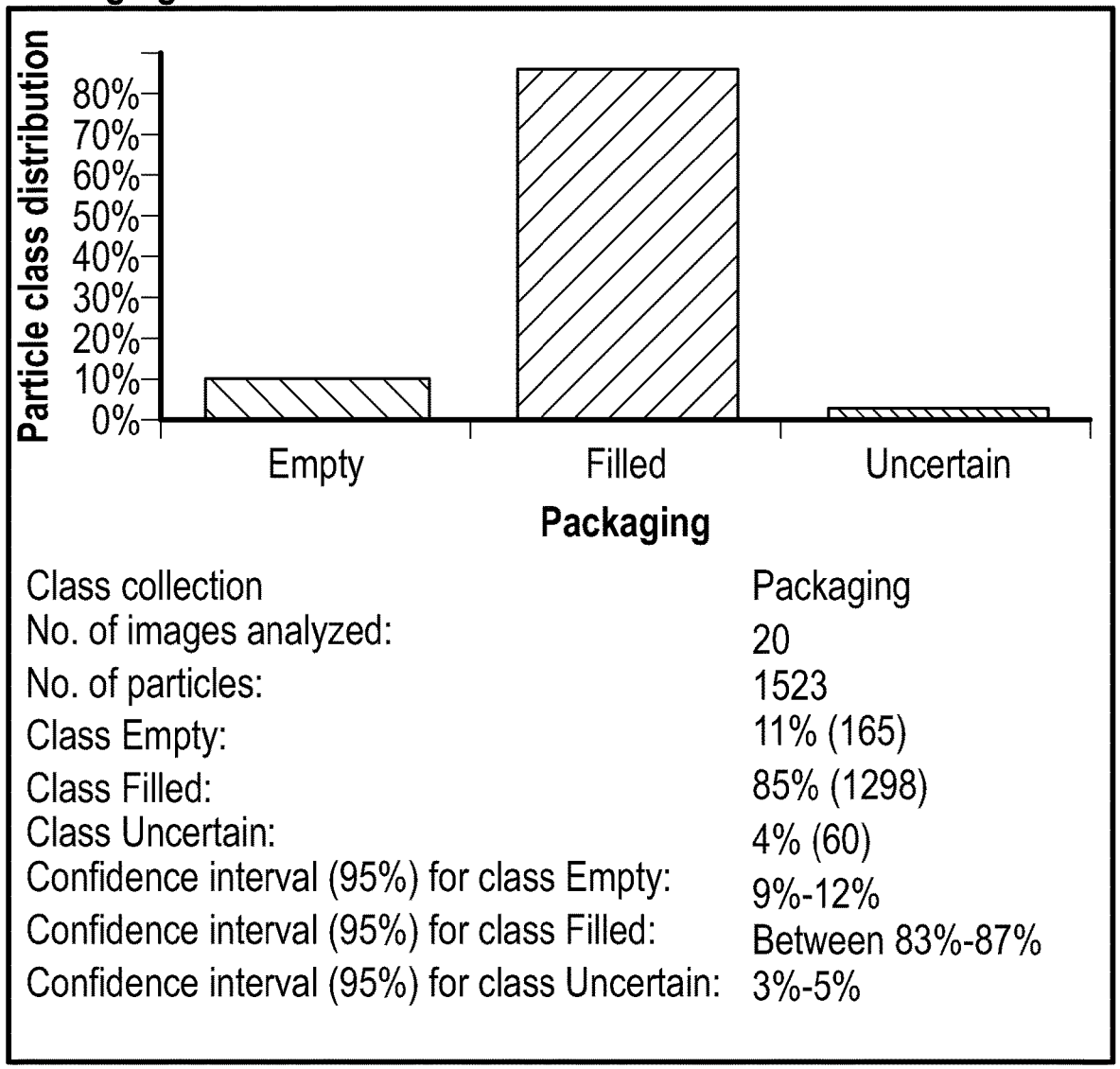
Figure 35B:
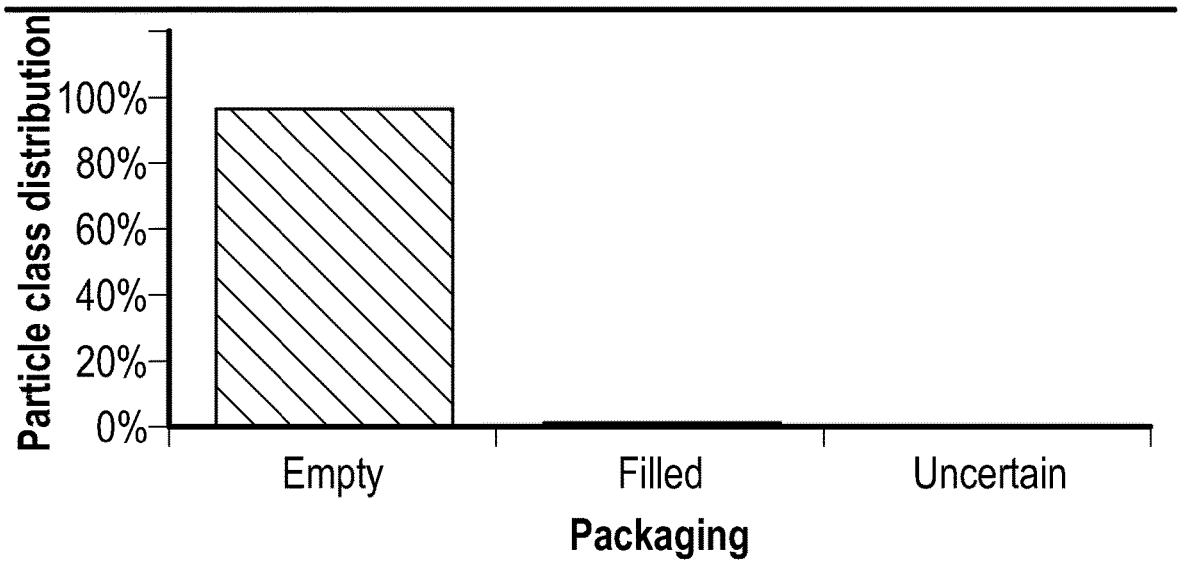

FIGS. 35A and 35B are representative graphs of CryoTEM analysis for Full rAAV6-GLA3 and Empty AAV6-030 samples.

Figure 36A:
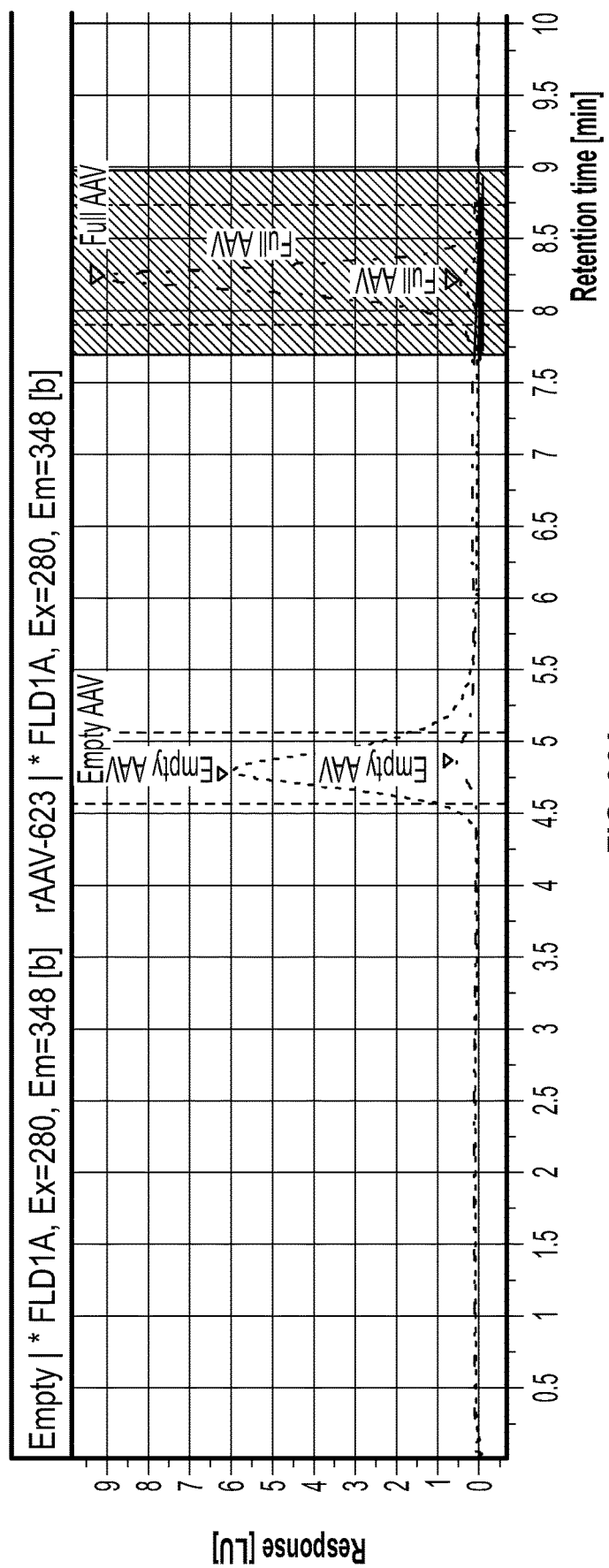
Figure 36B:
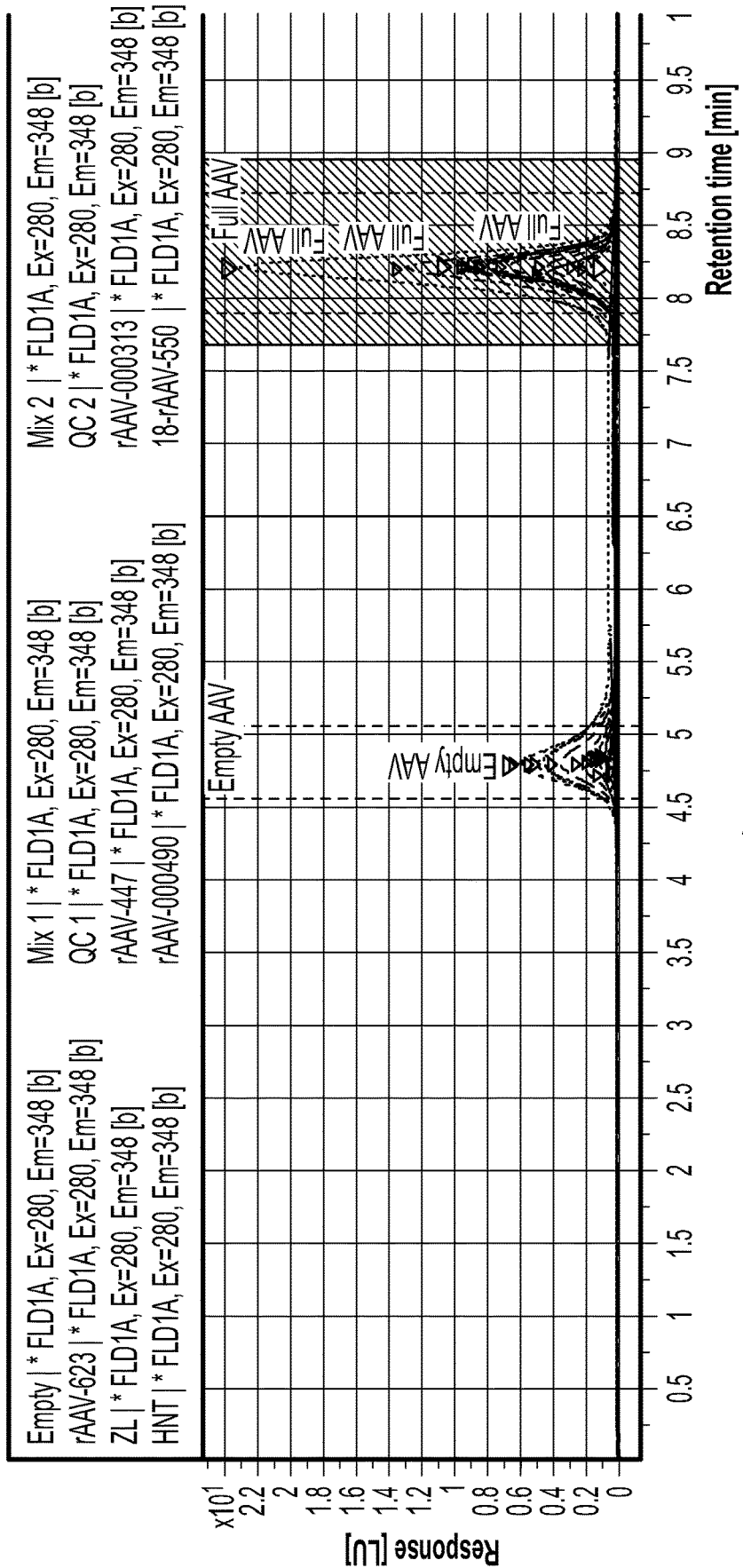

FIGS. 36A and 36B are representative HPLC chromatogram showing peak separation and retention time results for full rAAV6-GLA3, Empty AAV6-030 and other samples used for comparison with the CryoTEM.

Figure 37A:
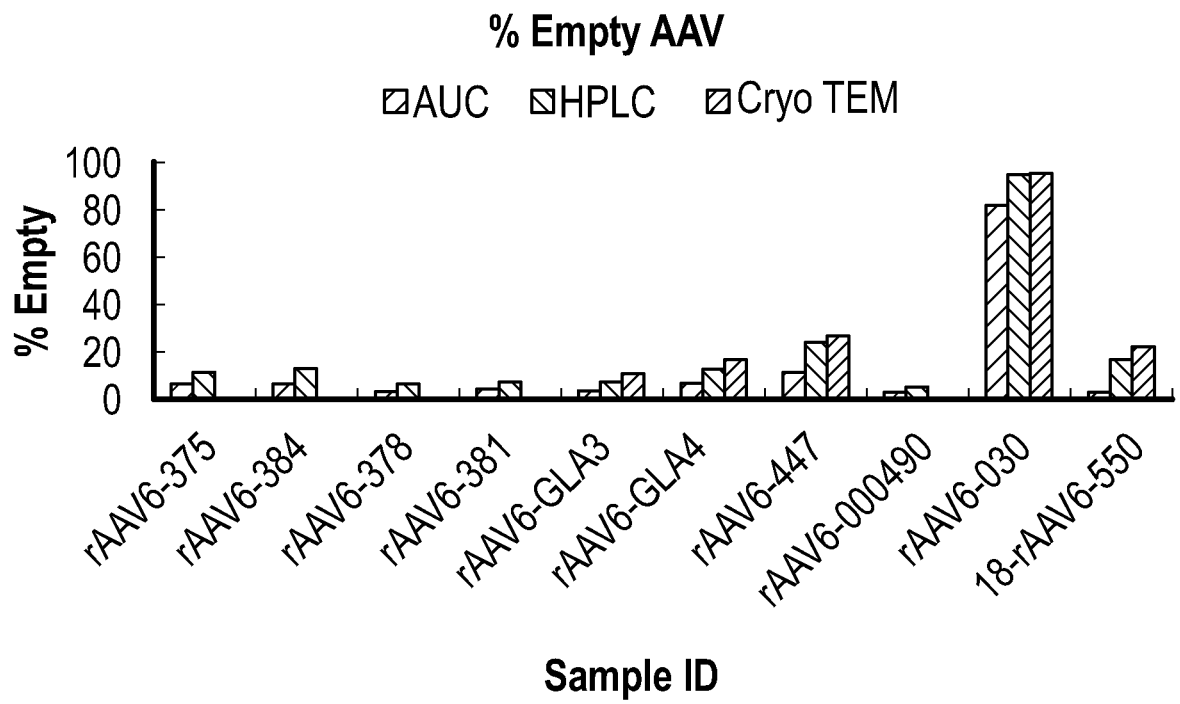
Figure 37B:
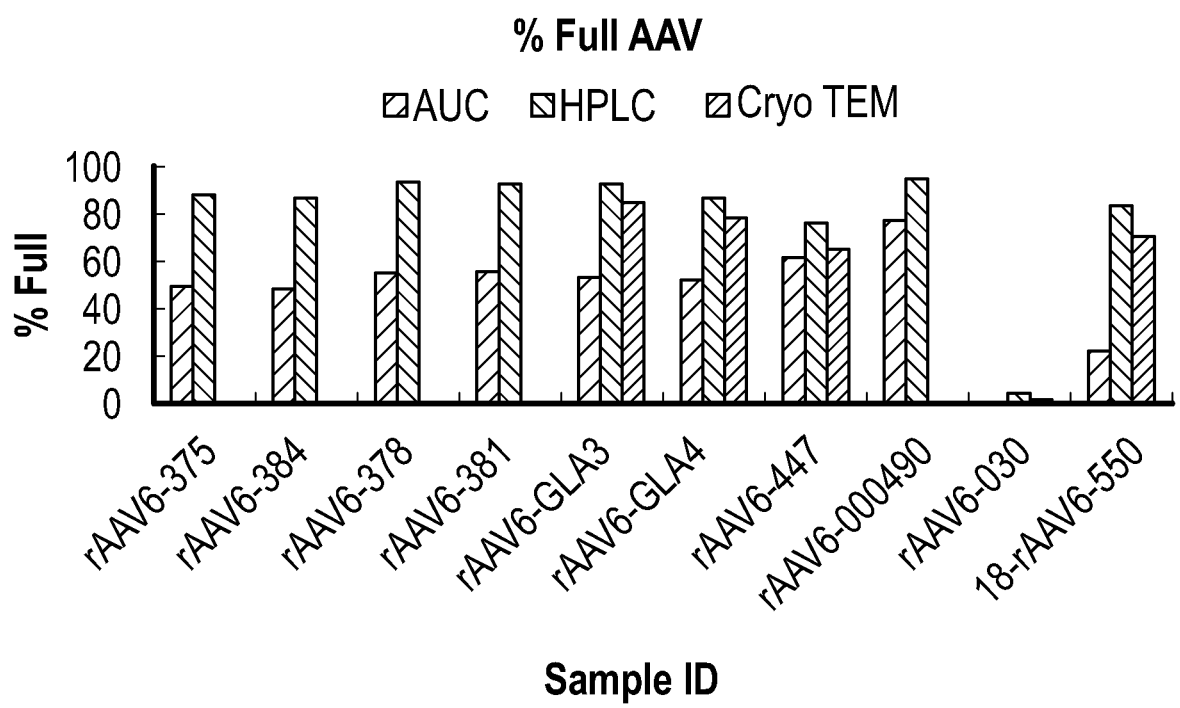

FIGS. 37A and 37B are graphs showing the comparison of the percent quantification of empty (A) and full AAV capsids (B) from different rAAV6 samples as tested by AUC, HPLC, and CryoTEM methods.

Figure 38A:
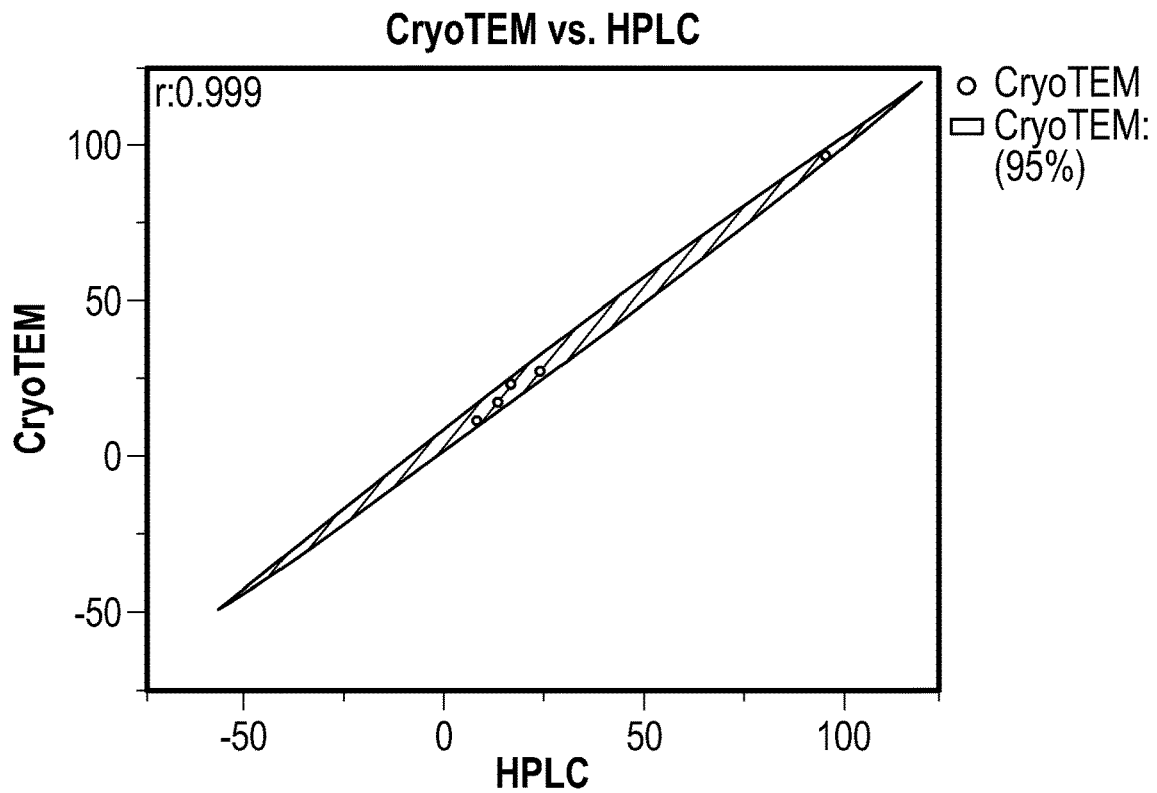
Figure 38B:
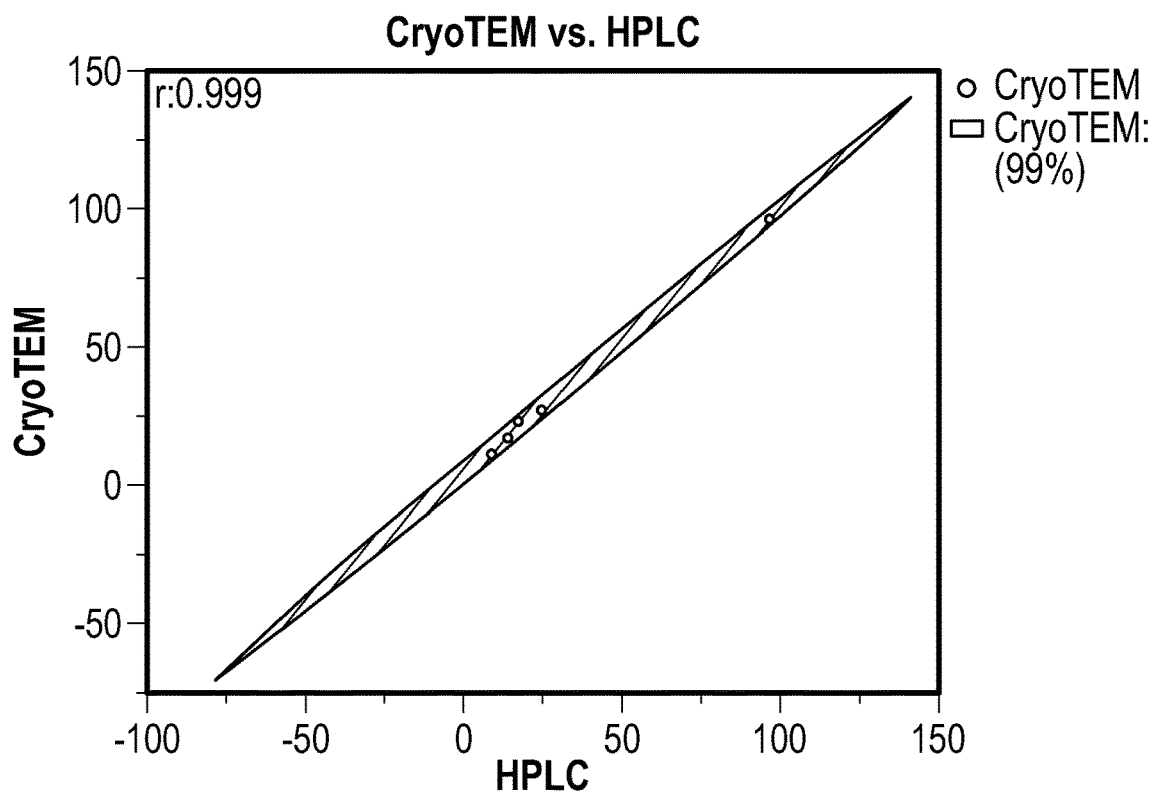

FIGS. 38A and 38B are graphs showing the correlation of the percentage of empty (A) and full (B) AAV particles in different viral samples calculated using HPLC and CryoTEM using the JMP software.

Figure 39:
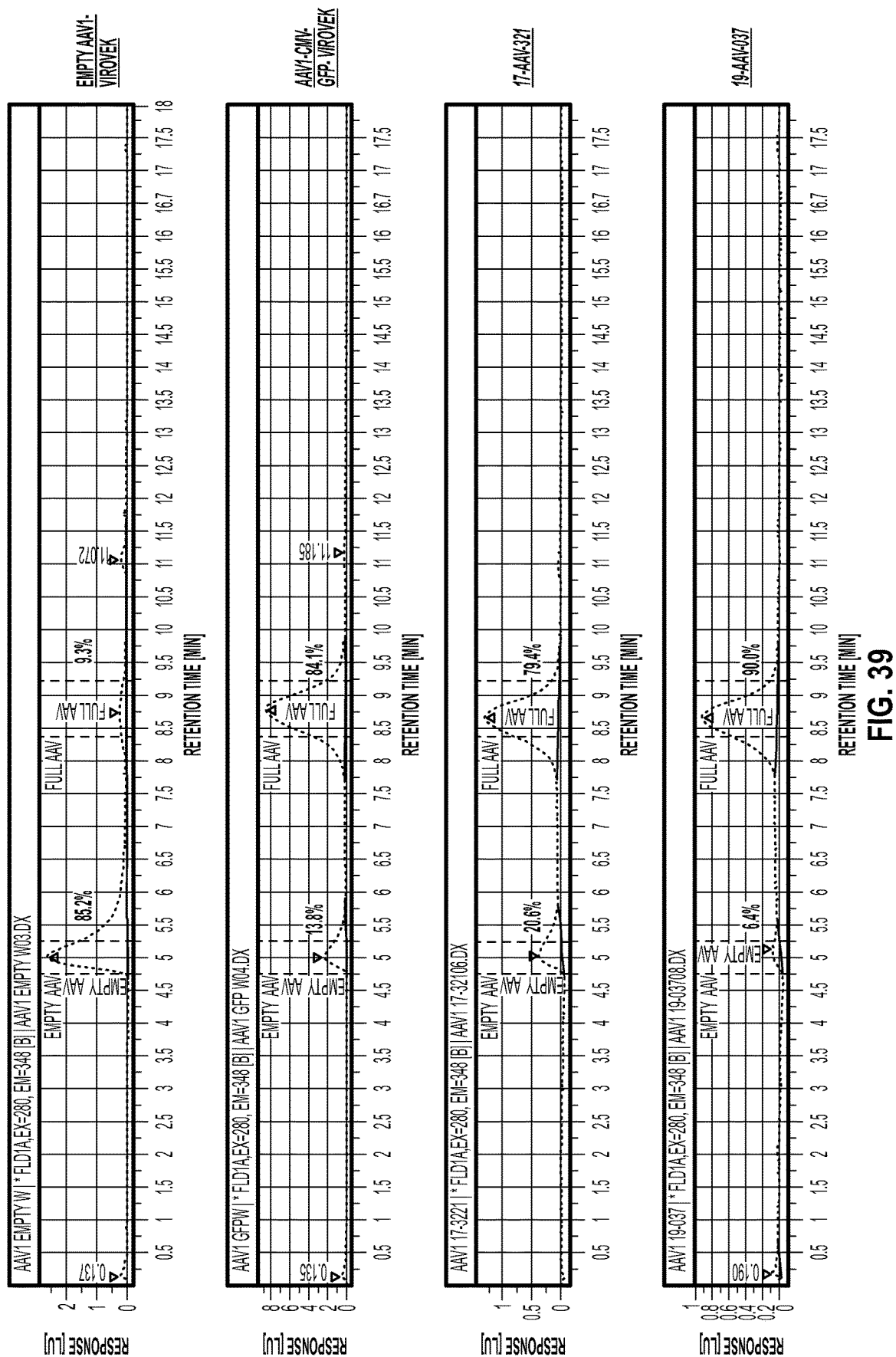

FIG. 39 is a set of HPLC chromatograms showing peak separation, retention time, and percent quantification results of empty and full AAV capsids for AAV1 Empty Lot and recombinant AAV1 samples (AAV1-CMV-GFP, 17-AAV-321, and 17-AAV-037) using an elution buffer comprising TMAC run at a gradient of about 0%-30% with an isocratic hold at about 20%.

Figure 40:
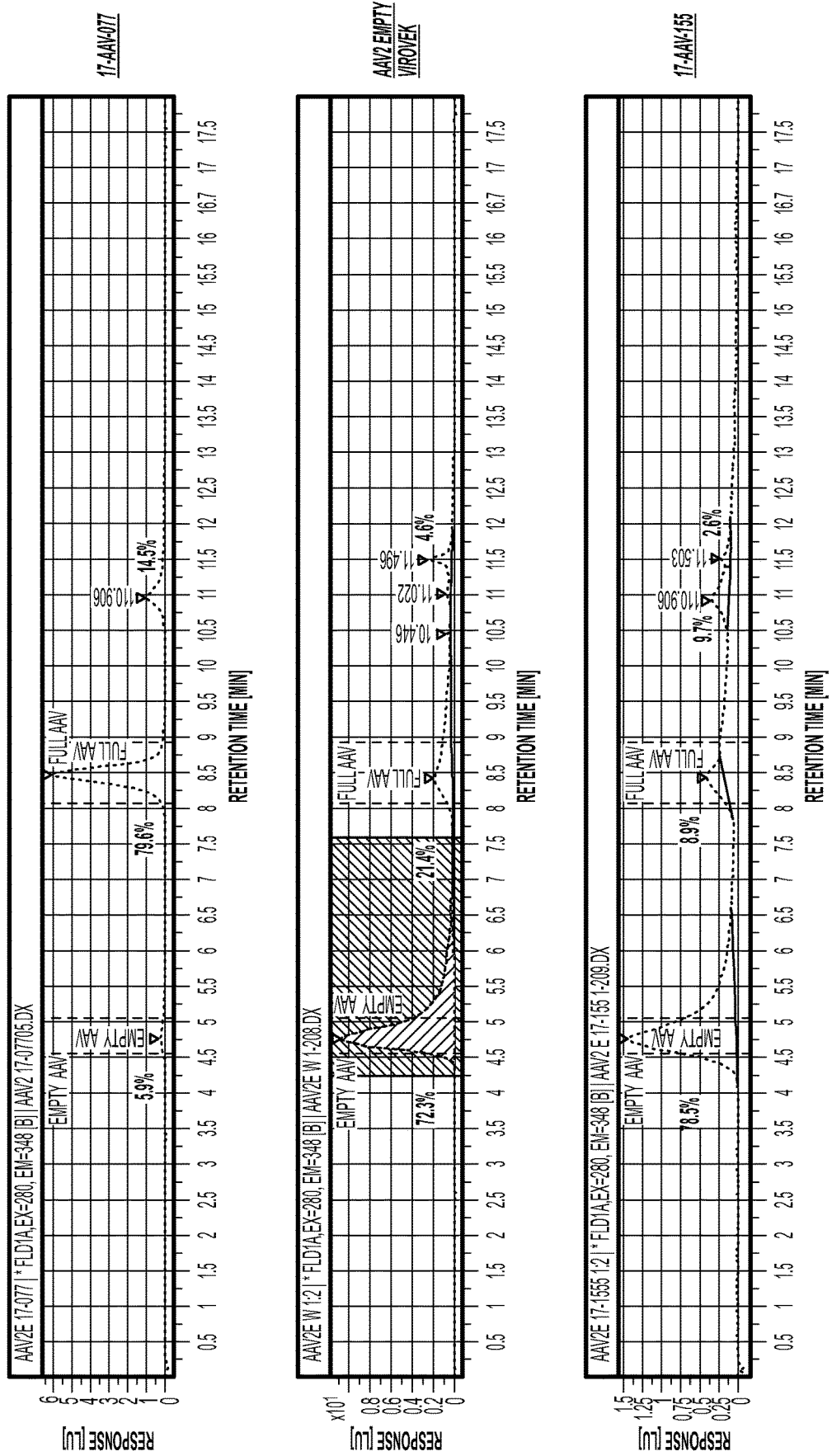

FIG. 40 is a set of HPLC chromatograms showing peak separation, retention time, and percent quantification results of empty and full AAV capsids for AAV2 Empty Lot and recombinant AAV2 samples (17-AAV-077 and 17-AAV-155) using an elution buffer comprising TMAC run at a gradient of about 0%-30% with an isocratic hold at about 12%.

Figure 41:
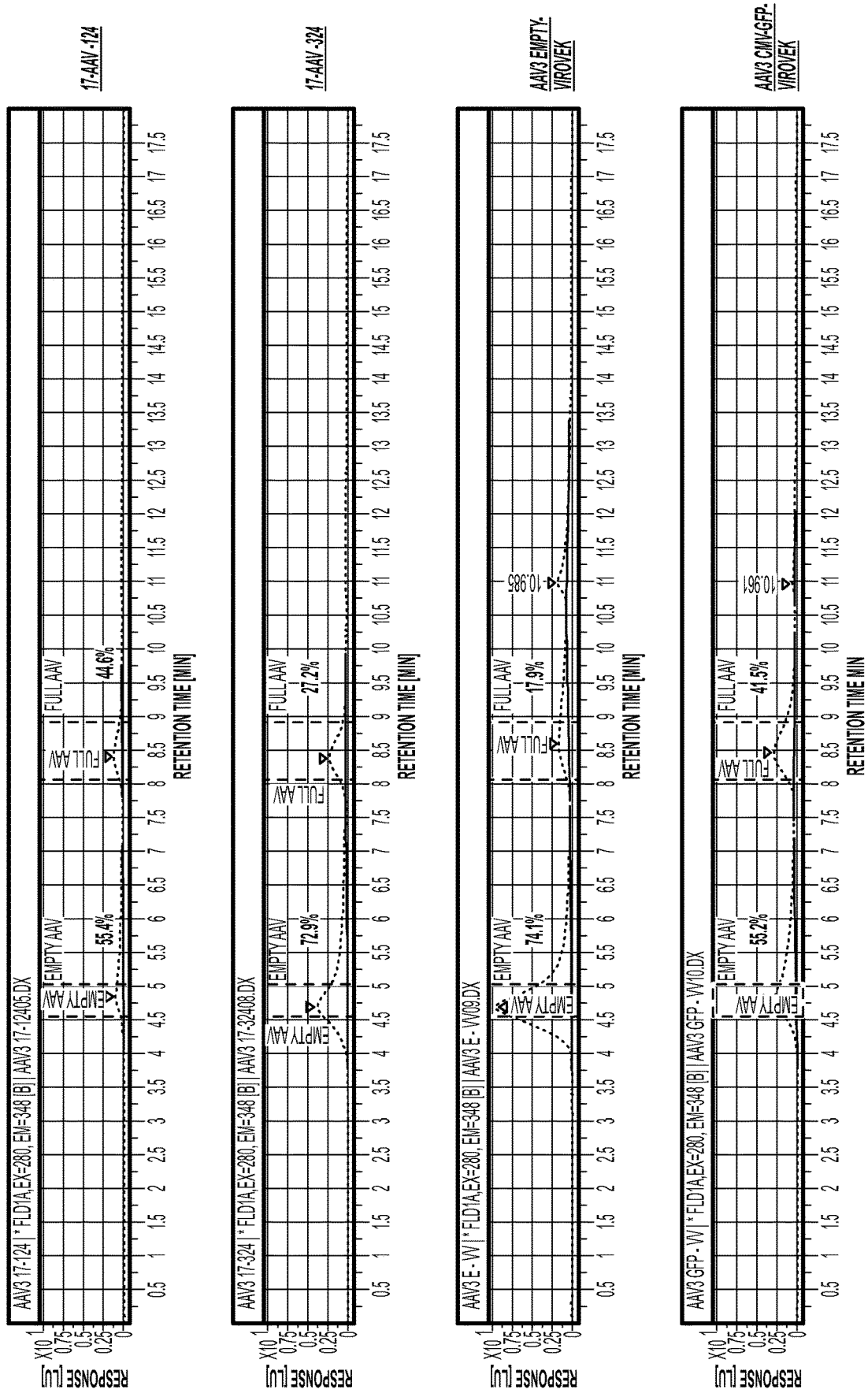

FIG. 41 is a set of HPLC chromatograms showing peak separation, retention time, and percent quantification results of empty and full AAV capsids for AAV3 Empty Lot and recombinant AAV3 samples (AAV3-CMV-GFP, 17-AAV-124, and 17-AAV-324) using an elution buffer comprising TMAC run at a gradient of about 0%-30% with an isocratic hold at about 15%.

FIGS. 42A and 42B are sets of HPLC chromatograms showing peak separation, retention time, and percent quantification results of empty and full AAV capsids for AAV8 Empty Lot (17-AAV-082) and recombinant AAV8 samples (18-AAV-070, 17-AAV-339, 17-AAV-340, 17-AAV-341, and AAV8 RSM) using an elution buffer comprising TMAC run at a gradient of about 0%-30% with an isocratic hold at about 14%.

Figure 43:
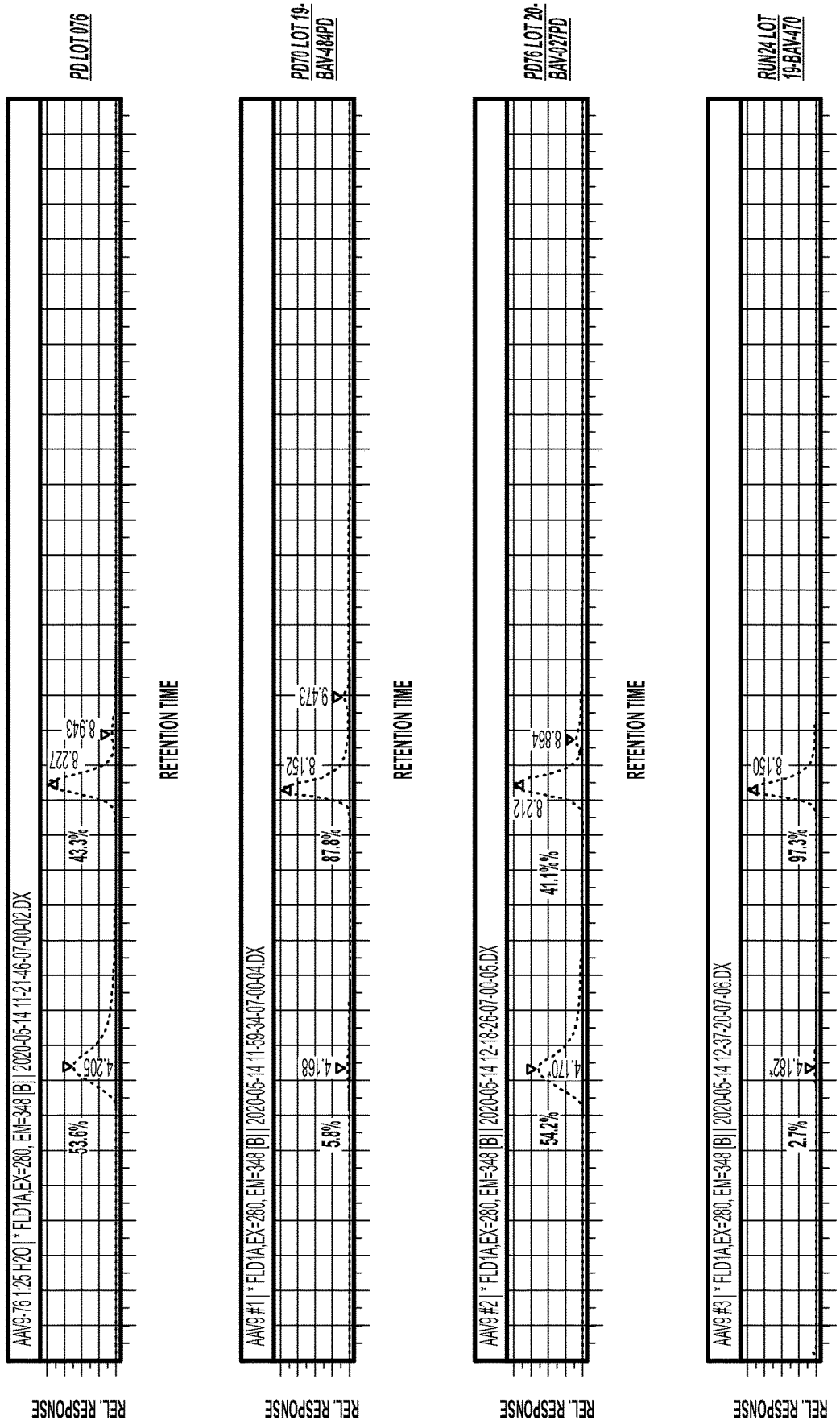

FIG. 43 is a set of HPLC chromatograms showing peak separation, retention time, and percent quantification results of empty and full AAV9 capsids for samples PD Lot 076, PD70 Lot 19-BAV-484PD, PD76 Lot 20-BAV-027PD, and Run24 Lot 19-BAV-470 using an elution buffer comprising TMAC run at a gradient of about 0%-40% with an isocratic hold at about 5%.

DETAILED DESCRIPTION OF THE INVENTION

Methods described herein may be used for separating and quantifying empty adeno-associated virus (AAV) capsids and full AAV (e.g., recombinant AAV or rAAV) capsids in AAV preparations such as AAV pharmaceutical compositions and drug products using column chromatography. For example, high-performance liquid chromatography (HPLC), also known as high pressure liquid chromatography, can be used to baseline separate empty AAV capsids and full AAV (rAAV) capsids in viral preparations, pharmaceutical compositions and drug products to a degree at which the area or height of each peak may be accurately measured.

AAV is a non-enveloped single-stranded DNA virus that can be engineered to deliver DNA (e.g., therapeutic or reporter genes) to target cells. During AAV vector manufacturing, DNA is packaged into a self-assembled viral particle through the action of the AAV replicase (Rep) protein. However, this DNA packaging process is often inefficient, leading to a quantity of empty particles that lack the vector genome. Depending on the manufacturing process used, empty particle contamination can be as high as 20- to 30-fold excess over full particles for transfection-based procedures (Lock et al., *Hum. Gene Ther.* (2010b) 21:1273-1285). The presence of empty particles effectively increases the dose of the AAV capsid proteins given during therapy and therefore increases the potential for unwanted immune consequences against the vector capsid. Accordingly, the methods described herein may also be used to purify large scale production batches of viral preparations, pharmaceutical compositions, and drug products.

The terms "empty capsid," "empty vial particle," and "empty AAV" refer to an AAV virion that includes an AAV protein capsid shell essentially similar to that of the desired product but lacks a nucleic acid molecule packaged within.

The terms "full capsid," "full viral particle," "rAAV," and "full rAAV" refer to an AAV virion that includes an AAV protein capsid shell encapsidating a nucleotide sequence of interest.

The inventors have made the unexpected discovery that improved HPLC parameters can be used to achieve baseline resolution between chromatogram peaks corresponding to empty and full AAV capsids within a sample. Peak resolution is the distance between two peaks on a chromatogram. By "baseline separation" or "baseline resolution" is meant a resolution factor of at least 1.5. When the resolution is >1.5, then there will be about <1% mutual interference between the two peaks. In some embodiments, chromatographic peaks corresponding to empty and full vial particles (capsids) are separated by a baseline resolution of >2.0. In some embodiments, peak resolution is greater than 2.0.

HPLC systems described herein comprise stationary and mobile phases. For example, monolith strong anion-exchange (SAX) columns comprising a poly(glycidyl methacrylate-co-ethylene dimethacrylate) support matrix may be used as a stationary phase to separate empty and full AAV capsids based on the slightly less anionic character of empty particles compared to vectors. In some circumstances, it may be beneficial to utilize a weak anion-exchange (WAX) column, where sample binding conditions permit, in order to achieve chromatogram peak baseline separation. In some circumstances, it may be beneficial to utilize a strong cation-exchange (SCX) column or a weak cation-exchange (WCX) column, where sample binding conditions permit, in order to achieve chromatogram peak baseline separation. It is preferable for retention times (RT) to be high enough to allow for better separation of peaks and to increase the capacity factor. Therefore, mobile phase pH may be adjusted to achieve baseline separation. In some embodiments, SAX, WAX, SCX, or WCX columns or multiple strong AEX, CEX, SAX, WAX, SCX, or WCX columns may be used in a tandem arrangement, connected such that the column length is increased.

In some embodiments, the mobile phase comprises buffer compositions such as bis-Tris propane (BTP), for example. Mobile phase buffer concentrations may be varied. For example, concentrations of about 1 mM to about 100 mM (e.g., 1 to 50 mM) may be used. In some embodiments, an elution buffer in the mobile phase may comprise one or more salts, including but not limited to, sodium chloride (NaCl), potassium chloride (KCl), tetramethylammonium chloride (TMAC), sodium acetate (NaOAc), and/or ammonium acetate ($NH_4OAc$). In some embodiments, the salt may be at a concentration of about 0.1 M to about 10 M, or about 0.2 M, 0.3 M, 0.4 M, 0.5 M, 0.6 M, 0.7 M, 0.8 M, 0.9 M, 1.0 M, 1.5 M, 2.0 M, 3.0 M, 3.5 M, 4 M, 4.5 M, 5.0 M, 5.5 M, 6.0 M, 6.5 M, 7 M, 7.5 M, 8.0 M, 8.5 M, 9.0 M, or 9.5 M. In some embodiments, the pH of the buffer composition is about 9.0. In some embodiments, mobile phase buffer pH is in the range of about 8.0 to about 9.5

The mobile phase can be run as a gradient (i.e., gradient-elution chromatography). Steady changes in mobile phase composition during the chromatographic run are referred to as gradient elution. For example, the elution solvent can begin at a particular percentage and can be steadily increased over time. Gradients can begin at 0% increasing to about 100%. In some embodiments, the gradient begins at about 2%-15% and is increased to about 30%-100%, wherein the mobile phase comprises a 1 M salt elution solvent. In other embodiments, the gradient begins at about 10% and is increased to about 30%. In yet other embodiments, the gradient begins at about 15% and is increased to about 30%. In yet other embodiments, the gradient begins at about 15% and is increased to about 35%. In other embodiments, the gradient begins at about 15% and is increased to about 40%. In other embodiments, the gradient begins at about 15% and is increased to about 45% or about 50%.

The mobile phase may be run as a shallow gradient (longer run time or slower increase in eluant solvent strength) or a steep gradient (shorter run time or faster increase in eluant solvent strength) or combinations of the two. In addition, an isocratic hold may be incorporated in the gradient mobile phase. In an isocratic hold or flow, the mobile phase composition is kept constant. The inventors have made an important discovery that incorporating an isocratic hold into the gradient elution significantly improves resolution of chromatographic peaks corresponding to empty and full viral particles and produces baseline separation of the peaks. This in turn increases the accuracy with which the quantity of empty and full viral particles within a sample may be measured.

In certain embodiments, an isocratic hold at about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30% may be incorporated into the gradient elution of chromatographic runs. In some embodiments, peak symmetry is also improved by the addition of an isocratic hold flanked by two gradients within the method. In other embodiments, peak asymmetry and tailing is less than 2.0.

In some embodiments, the run time for the mobile phase, whether run as a gradient or not, is between about 1 minute and 60 minutes. In other embodiments, the run time for the mobile phase is about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, or about 45 minutes.

The HPLC methods described herein may be used with UV or fluorescence detection. In some embodiments, wavelengths for excitation and emission are set at 280 nm±20 nm and 348 nm±20 nm, respectively.

In some embodiments, the response time for detectors is set at 0.5 seconds. In some embodiments, the response time is set to generate at least 20 datapoints across a chromatographic peak. In some embodiments, the response time is set at between about 0.1-1.0 seconds.

The viral preparations may be obtained by any known production systems, such as mammalian cell AAV production systems (e.g., those based on 293T or HEK293 cells) and insect cell AAV production systems (e.g., those based on sf9 insect cells and/or those using baculoviral helper vectors). The viral preparations may be purified from the cell cultures by using well known techniques such as discontinuous cesium chloride density gradients (see, e.g., Grieger, *Mol Ther Methods Clin Dev.* (2016) 3:16002).

The present methods can be used to purify and analyze viral preparations of a variety of AAV serotypes, such as AAV1, AAV2, AAV3, AAV3b, AAV4, AAV5, AAV6, AAV7, AAV8, AAV8.2, AAV9, AAVrh10, AAV10, and AAV11, as well as variants, hybrids, chimera or pseudo-types thereof. By "pseudo-typed" or "cross-packaged" rAAV is meant a recombinant AAV whose capsid is replaced with the capsid of another AAV serotype, to, for example, alter transduction efficacy or tropism profiles of the virus (e.g., Balaji et al., *J Surg Res.* 184(1):691-8 (2013)). By "chimeric" or "hybrid" rAAV is meant a recombinant AAV whose capsid is assembled from capsid proteins derived from different serotypes and/or whose capsid proteins are chimeric proteins with sequences derived from different serotypes (e.g., serotypes 1 and 2; see, e.g., Hauck et al., *Mol Ther.* 7(3):419-25 (2003)). For example, the present methods may be used to purify and analyze recombinant AAV whose genome such as the ITRs is derived from one serotype such as AAV2 while the capsids are derived from another serotype; e.g., AAV2/8, AAV2/5, AAV2/6, AAV2/9, or AAV2/6/9. See, e.g., U.S. Pat. Nos. 7,198,951 and 9,585,971

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cardiology, medicine, medicinal and pharmaceutical chemistry, and cell biology described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context. As used herein, a value "between" two numbers may be one of the two numbers.

In order that this invention may be better understood, the following examples are set forth. These examples are for purposes of illustration only and are not to be construed as limiting the scope of the invention in any manner.

EXAMPLES

Example 1: Anion-Exchange HPLC for Separating Empty and Full Viral Particles Anion Exchange HPLC was assessed for its ability to separate empty AAV particles and recombinant AAV (rAAV) (full) particles within a viral preparation. Four different AAV samples were run to assess chromatographic peak separation and peak positioning for empty AAV capsids and full AAV capsids (rAAV samples). Samples included: Final Formulation Buffer (FFB); a reference sample predominately comprised of full AAV capsids (Full rAAV6-GLA3), manufactured by a vendor; a Sangamo prepared sample predominately comprised of full AAV capsids (rAAV6-GLA3); and a Sangamo prepared sample predominately comprised of empty AAV capsids (Empty AAV6-030).

An Agilent 1100 HPLC system was used. Liquid Chromatography—Mass Spectrometry (LC-MS) grade or HPLC-grade reagents can be used to reduce background. In this example, LC-MS grade reagents were used to prepare the mobile phase comprised of bis-Tris propane and sodium chloride. The HPLC buffers were prepared by dissolving HPLC-grade or highly pure compounds in LC-MS grade water. The buffer solutions were adjusted to appropriate pH and filtered through 0.2 μm filters. The solutions were then transferred into HPLC-bottles. Line A in this example HPLC system was selected for buffer containing lower amounts of salt while line B was selected for buffer with higher salt concentrations. Line C was selected for HPLC-grade water while line D was used for isopropyl alcohol (IPA). Lines C and D were used only when needed to change the solvent or flush the system. For separation, a monolith AAV analytical column was used. Before the start of the experiments, the solvent lines were put in appropriate bottles and flushed for at least 5 min (per line) at 3 mL/min.

A CIMac™πAAV full/empty-0.1 Analytical Column (1.3 μm) anion exchange column (BIA Separations, Slovenia) was cleaned with high salt buffer for 10-15 min at 1 mL/min while monitoring the pressure (usually less than column specification). The column was then equilibrated with initial conditions of the method. If a buffer needed to be switched, the solvent lines were flushed with water first followed by the next buffer. For long term storage, the solvent lines and system are flushed with IPA before shutting down the system. As a buffering agent, bis-Tris propane (BTP) was used as it has two pKa values and covers a range of pH values (about 6.5-9.5). The buffer concentration was selected as about 20 mM to allow for sufficient buffering capacity without increasing the ionic strength significantly. However, other suitable concentrations may be used.

Figure 1A:
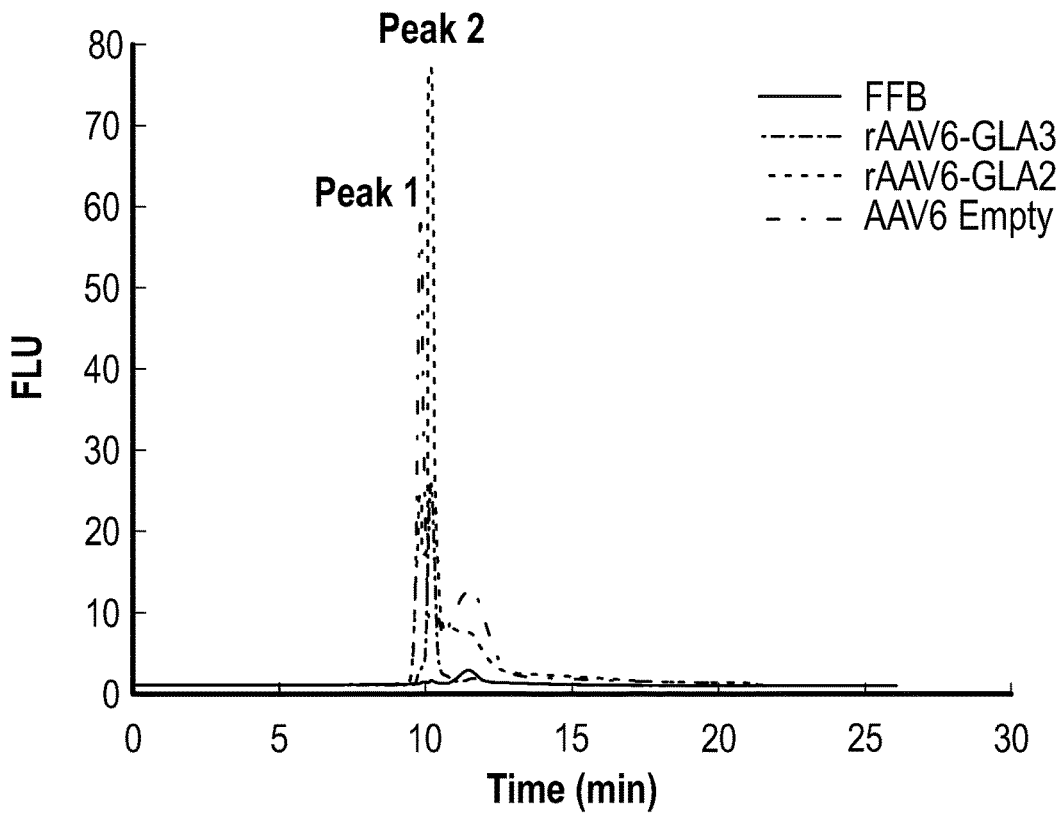
FIG. 1A and FIG. 1B are representative HPLC chromatograms of three different samples (stacked) showing the peak positioning for empty AAV (Peak 1) and full AAV (Peak 2)
Figure 1B:
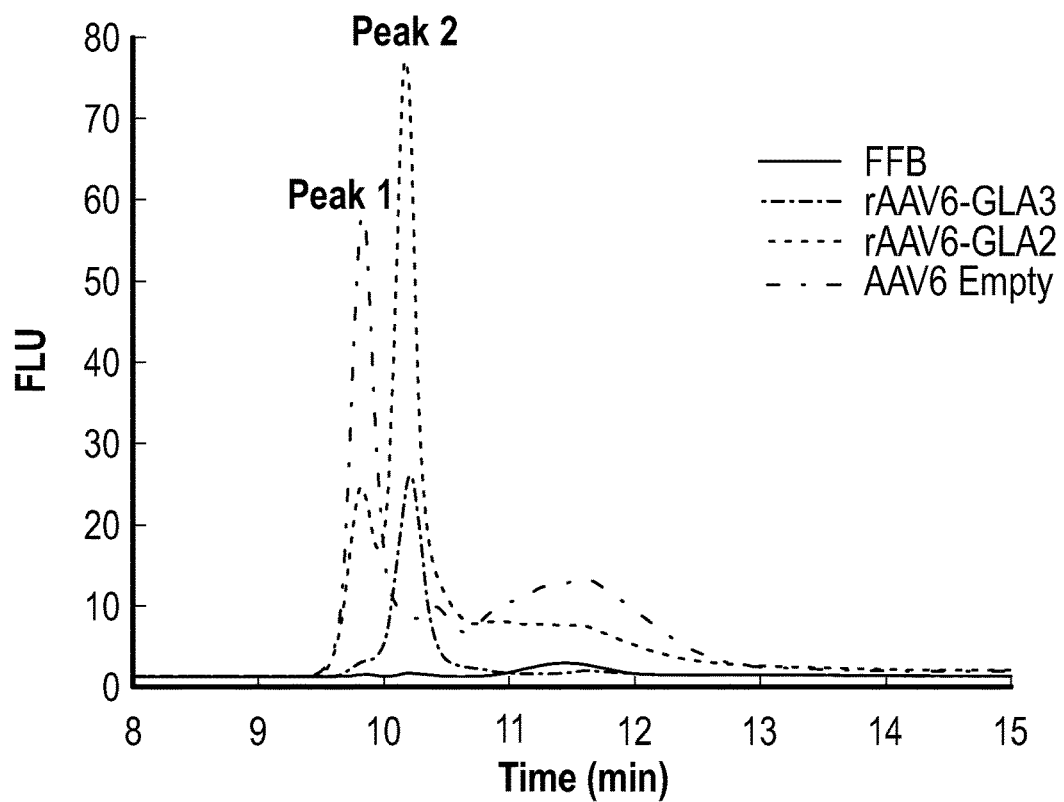

FIG. 1A and FIG. 1B are representative chromatograms of three different samples (stacked) showing the peak positioning for empty AAV (Peak 1) and full AAV (Peak 2) particles. As shown in FIG. 1A (30 min) and FIG. 1B (15 min), all samples demonstrated a distinct pattern of peak separation. Samples mainly comprising full capsids displayed a smaller peak, corresponding to empty capsids, followed by a larger peak, corresponding to full capsids, with no baseline separation between them. The empty AAV sample displayed a larger peak corresponding to an empty capsid which indicates the peak positioning of empty vs. full AAV particles.

Although data from the fluorescent (Trp) mode is shown because the sensitivity is higher, a similar pattern of peaks is observed using UV.

All three samples show consistent peak positions (retention times) for Empty AAV and Full AAV particles. Even though there was no baseline resolution, the peak integration was used to calculate peak areas. The ratio of peak areas can be used to calculate empty to full AAV ratio. Although baseline resolution between peaks is necessary in order to achieve a validatable assay according to USP regulations, this method can be used to estimate the approximate percentages of empty particles in AAV drug products.

Example 2: Anion Exchange HPLC for Calculation of the Percentage of Empty and Full Viral Particles in Viral Samples The peak areas from multiple samples were used to calculate the percentage of Full AAV particles in each sample. In addition, VG titer was measured using primer/probe sequences targeting BGH Poly A region in the AAV cassette and capsid titers were measured using an AAV6 ELISA kit. Based on both VG and Capsid data, the ratio was calculated to obtain the percentage of Full AAV particles. Table 1 shows peak areas determined by the HPLC method described in Example 1 (two runs), VG, and capsid titer.

Full rAAV6-381 contains a genome including an expression cassette for a zinc finger nuclease (ZFN) transgene and having a size of 2,629 bases. Full rAAV6-375 contains a genome including an expression cassette for an IDUA transgene and having a size of 3,077 bases. Full rAAV6-384 contains a genome including an expression cassette for an IDS transgene and having a size of 2,780 bases. Full rAAV6-GLA3 contains a genome including an expression a cassette for a GLA transgene and having a size of 2,772 bases. Full rAAV6-GLA1 and Full rAAV6-GLA2 each contain a genome including an expression cassette for a GLA gene and having a size of 2,729 bases and 3,321 bases, respectively. All of the samples used herein were research-only samples.

TABLE 1

% Full AAV calculated by HPLC method vs. VG/Cap method

| Samples | HPLC 1 | | | | HPLC 2 | | | | Vg Titer | Capsid Titer | Vg/Cap Ratio |
|---|---|---|---|---|---|---|---|---|---|---|---|
| | Empty | Full | Other | % F | Empty | Full | Other | % F | | | |
| Full rAAV6-381 | 21.4 | 452 | 11.3 | 93 | 3.1 | 379.3 | 11.3 | 96 | 9.44E+12 | 9.22E+12 | 1.02 |
| Full rAAV6-375 | 46.7 | 604.9 | 10 | 91 | 8.5 | 459.9 | 10.3 | 96 | 1.11E+13 | 1.32E+13 | 0.84 |
| Full rAAV6-384 | 35 | 372.6 | 10.5 | 89 | 9.3 | 277.6 | 11.1 | 93 | 9.03E+12 | 7.58E+12 | 1.19 |
| Full rAAV6-GLA3 | 0 | 432.3 | 11.1 | 97 | 0 | 423.4 | 10.6 | 98 | 7.07E+12 | 7.69E+12 | 0.92 |
| Full AAV6-GLA1 | 32.9 | 321.2 | 15.5 | 87 | 8.8 | 211.5 | 14.4 | 90 | 3.26E+12 | 9.83E+12 | 0.33 |
| Full AAV6-GLA2 | 313.3 | 1072.3 | 782.9 | 49 | 142 | 697.9 | 20.4 | 81 | 2.75E+13 | 4.55E+13 | 0.60 |
| AAV6 Empty Capsid | 1591.1 | 35.8 | 743.6 | 2 | 723.4 | 24.5 | 548.4 | 2 | 8.23E+08 | 2.89E+13 | 0.00 |

The percentage of full viral particles measured by HPLC and VG/Capsid were plotted and compared for all samples. The ratios for all of the samples, except the GLA1 and GLA2 samples, were similar, indicating that there is a correlation between results from HPLC and other accepted methods. The comparison of the methods is shown in FIG. 2.

Example 3: Precision of Anion Exchange HPLC for Calculation of the Percentage (%) of Empty and/or Full Viral Particles in Viral Samples To test the precision of the HPLC method described in Example 1, the same samples of Full rAAV6-375 and Full rAAV6-381 were run 5 times and the peak area was calculated for the full AAV particles. Samples Full rAAV6-375 and Full rAAV6-381 differ in that the viral particles within the sample contain different transgenes. Based upon USP guidelines, the precision should be <2%. As shown in Table 2 and Table 3, measured peak areas demonstrated injection precision of <2%. The percent recovery was close to 100% (as calculated based on the first sample injection) as well. The peak areas for UV260 and 280 were also obtained and used to calculate 260/280 ratio. However, the fluorescence signal demonstrated a higher signal to noise ratio.

TABLE 2

Precision of 5 independent injections of sample 1 (Full rAAV6-375) and % recovery of peak area

| Full rAAV-375 | Injection 1 | | Injection 2 | | Injection 3 | | Injection 4 | | Injection 5 | |
|---|---|---|---|---|---|---|---|---|---|---|
| | Area | % Recovery | Area | % Recovery | Area | % Recovery | Area | % Recovery | Area | % Recovery |
| A260 | 307.8 | 100% | 307.3 | 100% | 308 | 100% | 307.9 | 100% | 306.6 | 100% |
| A280 | 230.4 | 100% | 230.4 | 100% | 230.8 | 100% | 230.4 | 100% | 230 | 100% |
| FL | 1673.6 | 100% | 1446.6 | 86% | 1675.5 | 100% | 1442.9 | 86% | 1673.4 | 100% |
| A260/A280 | 1.34 | — | 1.33 | — | 1.33 | — | 1.34 | — | 1.33 | — |

TABLE 3

Precision of 5 independent injections of sample 2 (Full rAAV6-381) and % recovery of peak area

| Full<br>rAAV-381 | Injection 1 | | Injection 2 | | Injection 3 | | Injection 4 | | Injection 5 | |
|---|---|---|---|---|---|---|---|---|---|---|
| | Area | % Recovery | Area | % Recovery | Area | % Recovery | Area | % Recovery | Area | % Recovery |
| A260 | 231.1 | 100% | 229.7 | 99% | 227.9 | 99% | 227.8 | 99% | 225.6 | 98% |
| A280 | 173.5 | 100% | 172.3 | 99% | 171 | 99% | 169.9 | 98% | 168.3 | 97% |
| FL | 1174.7 | 100% | 1167.9 | 99% | 1179.9 | 100% | 1172.7 | 100% | 1167.7 | 99% |
| A260/A280 | 1.33 | — | 1.33 | — | 1.33 | — | 1.34 | — | 1.34 | — |

Example 4: Linearity of Anion Exchange HPLC for Varying Injection Volume, Capsid Concentration, and Capsid Content The linearity of injection volumes as well as capsid concentrations were analyzed. HPLC procedures were performed according to the methods described supra. As shown in FIG. 3 and FIG. 4, the peak area results for full AAV particles were found to be linear when the volumes of the same sample were varied.

Samples were also diluted with FFB to different capsid titers and the same volume was then injected into the HPLC system for each diluted sample. Similarly, when the concentration of capsids was varied in a constant sample volume, the peak area results for full AAV particles were found to be linear. FIG. 5 and FIG. 6 show the linearity between different injected capsid concentrations at a constant volume.

Different viral composition samples with similar capsid titers were analyzed according to the methods described. The samples were diluted with FFB to the same capsid titer and the same volume was injected for each diluted sample. These results indicate that the quantity of capsids injected, regardless of sample type, will be approximately the same. Consistent peak areas for normalized samples were also demonstrated, as shown in FIG. 7.

A sample of AAV6 capsids containing GLA was used to determine peak separation under different temperatures. FIG. 8 shows that there was consistent peak separation for temperatures ranging from between about 20° C. to about 35° C.

AAV samples from different commercial vendors containing either GFP transgenes or empty preparations showed that all of the samples comprised heterogeneous mixtures of full and empty AAV particles. As shown in FIG. 9A, sample Full rAAV6-GLA3 had the highest percentage of full AAV particles.

Example 5: Eluant Variation on the Agilent 1260 HPLC System

The samples from the previous examples were analyzed on the Agilent 1260 HPLC system and demonstrated similar results and peak separation patterns (data not shown).

Four eluant salts (1 M solutions of NaCl, TMAC, sodium acetate and ammonium acetate) were analyzed for baseline separation between chromatogram peaks corresponding to empty and full capsids. The elution profiles of a full capsid sample (Full rAAV6-GLA3) and an empty capsid sample (AAV6-030) were obtained. The methods described previously were used except where indicated. The eluant buffer gradient was kept at 0-100% to obtain complete elution profiles since the ionic and elution strengths of the eluents are different. The retention time (RT) of major peaks in Full rAAV6-GLA3 and Empty AAV6-030 were compared and used to calculate the net RT. The highest net difference should produce the clearest baseline separation.

The elution profiles for the four eluant salts are shown in FIG. 10 and the net RT differences for the four eluant salts are presented in Table 4. Sodium chloride (NaCl) demonstrated the highest elution strength (and hence the lowest RT) while ammonium acetate (NH$_4$OAc) demonstrated the lowest elution strength (and thus a higher RT). The highest net RT difference was demonstrated using tetramethylammonium chloride (TMAC), followed by sodium acetate (NaOAc), while NaCl and NH$_4$OAc yielded lower net RT differences between the two samples.

TABLE 4

Net RT difference of elution of Full rAAV6-GLA3 and Empty AAV6-030

| Elution Salt (1M) | Empty Peak RT (min) | Full Peak RT (min) | Net RT (min) |
|---|---|---|---|
| NaCl | 3.699 | 3.783 | 0.084 |
| TMAC | 3.971 | 4.139 | 0.168 |
| NaOAc | 4.080 | 4.227 | 0.147 |
| NH$_4$OAc | 4.267 | 4.344 | 0.077 |

Example 6: Mobile Phase Comprising TMAC at Various Gradients

Various gradients of TMAC were analyzed to improve baseline separations between the peaks corresponding to full and empty virus particles. The method was performed as described previously except where indicated. Buffer A comprised 20 mM BTP at pH 9.0 while buffer B comprised 20 mM BTP with 1 M TMAC at pH 9.0. Previously, the gradient was run at 0-100%. However, to improve peak separation, shallower and narrower gradients were assessed. Each gradient was run with the Full rAAV6-GLA3 sample, the Empty AAV6-030 sample, and with a mix of both samples. Five injections were used to assess repeatability.

The chromatograms showing gradient separation using elution buffer comprising TMAC for full rAAV6-GLA3, Empty AAV6-030 and mixed samples are presented in FIG. 11A through FIG. 11C. Consecutive injections of the full and empty capsid mixed sample gave consistent peak RT and peak areas, demonstrating high precision of the method. In addition, the empty peak from the mixed sample matched the major peak in Empty AAV6-030 sample (FIG. 11A-FIG. 11C). To further improve the empty and full capsid peak separation, the gradient was narrowed from 0-100% to about 15-30% and multiple assays were run to determine repeatability. Although the peak separation was better with the narrower gradient, the peaks also became broader. Both peaks from the empty and full capsid mixed sample corresponded to similar peaks from full rAAV6-GLA3 sample and Empty AAV6-030 sample indicating that mixing two samples doesn't cause any unwanted shift in peak RT. These results indicate that viral samples produced by different methods comprising different payloads may still include a reasonable amount of both empty and full particles which can be identified and distinguished.

Example 7: Gradient Method with Weak Anion Exchange Column and Tandem Chromatography In Examples 1-6, AAV strong anion-exchange (AEX) monolith columns were used. In this study, weak anion exchange (WAX) columns (e.g., the BioWAX NP3 (nonporous, 4.5×50 mm, 3 μm HPLC column), were analyzed to determine their effect on empty and full viral particle peak separation. Tandem columns were also analyzed to determine whether increasing column length or combining two matrices (of weak and strong AEX) has an effect on empty and full viral particle peak separation. The monolith and WAX columns were attached back-to-back for tandem chromatography using a connector. Samples including the rAAV6-GLA039 (recombinant AAV6 carrying a GLA transgene Lot 039; Sangamo, Richmond, Calif.) and Empty AAV6-030 were used. The method described in the previous examples was used except where indicated. For both the WAX column and the monolith column, different mobile phase pH levels were analyzed for their effect on empty and full viral particle chromatogram peak baseline separation as well.

The monolith column demonstrated strong binding with mobile phases at pH 9.0. At lower pH levels, the RT shifted to the left indicating a loss in binding or reduced binding and faster elution. It is preferable for RT to be high enough to allow for better separation of peaks and to increase the capacity factor. However, peak separation was not demonstrated with mobile phases comprising certain pH levels. The WAX column showed tighter binding of samples (high RT) at the same pH levels as compared to the monolith column. There was less peak separation seen with the WAX column compared to the monolith column. In addition, the peak asymmetry became larger (wider peaks). At lower mobile phase pH levels, both columns showed lower binding of AAV and some or most of the viral composition eluted in void volume (between 0-1.5 mL) (FIG. 12A and FIG. 12B).

When the columns were used in tandem, the peak separation was similar to that of the monolith alone. In addition, when the pH was lowered, binding was reduced (lower RT) and there was less separation between the full capsid and the empty capsid peaks. Similarly, when two monolith columns were attached for tandem chromatography, peak separation remained the same, as shown in FIG. 13.

In conjunction with the described methods and samples, the monolith column (with Q-amine) produced better peak separation than the WAX (with diethylaminoethyl (DEAE)) column.

Example 8: Shallow Gradient with Monolith Column

A shallower gradient (longer run time) was analyzed to determine improved peak resolution between full and empty virus particle chromatography peaks. A monolith AAV column was used and the gradient was set to 15-30% of buffer B. Run time was varied. In the original method, the gradient was run over 5 min. Five more gradients were analyzed (10, 15, 20, 25, and 30 min). Consequently, the run time for each experiment became longer. A mix of Full rAAV6-GLA3 and Empty AAV6-030 was used as a viral composition test sample. Faster gradients (1, 2, 3, and 4 min) were also analyzed.

Turning to FIG. 14, the shallower gradient did not improve the peak resolution, as peaks were broader and resolved. However, when comparing the individual samples and mixed sample at a 5 min gradient time, sharper peaks were seen with asymmetry even though peak baseline resolution was not demonstrated. On the other hand, if faster gradients (1-4 min) were used, the separation did not improve and the peaks became sharper. (FIG. 15 and FIG. 16). Although it is desirable to have a fast method, the run time should be long enough to allow for efficient HPLC peak separation.

Example 9: Isocratic Hold within the Gradient Mobile Phase Produces Baseline Separation between Peaks Corresponding to Empty and Full Viral Particles An isocratic hold was incorporated into the gradient method to determine its effect on baseline separation between chromatogram peaks corresponding to empty and full viral particles within viral compositions. rAAV6-GLA039 was used as a full sample. Isocratic holds at about 17%, 18%, 19%, or 20% were tested with a gradient time of 10 min (same run time, different gradients). Once preferred conditions were determined, mixed samples comprising Full rAAV6-GLA3 and Empty AAV6-030 were analyzed.

Samples were freshly thawed on ice before the start of experiment. Each sample was analyzed directly or if needed diluted in FFB. The samples were transferred to HPLC vials and capped with appropriate caps with slits. The vials were then transferred to HPLC multi-sampler at desired positions and the locations were identified within the sequence.

As shown in FIG. 17 through FIG. 19, including an isocratic hold as part of the gradient mobile phase produced baseline separation between peaks corresponding to empty and full capsids in the same sample. Isocratic holds comprising about 17% or 18% produced clear separation for the Fabry sample (FIG. 17). When the mixed sample was analyzed, a similar pattern was shown (FIG. 18), with a clear peak baseline separation. Although, peak separation was demonstrated at higher percentage isocratic holds (about 19% or 20%), the sample didn't bind completely, and part of the sample was eluted in void volume.

To obtain complete binding, a gradient of about 0-40% was used in conjunction with an isocratic hold. This gradient allows for the samples to bind at the lowest ionic strength and maintain peak separation using an isocratic hold. These conditions produced binding of all or most of the sample composition with clear baseline resolution between empty and full peaks (FIG. 19).

The addition of an isocratic hold to the gradient mobile phase resulted in baseline resolution between peaks corresponding to empty and full viral particles. For quantitation of components within the sample using the methods described herein, conditions that allow for the binding of the entire sample are preferable to ensure that the sample will undergo gradient separation over the column and that little or none of the sample product will elute in void volume.

Example 10: Conditions for Enhanced Sample Binding, Peak Symmetry and Baseline Separation between Peaks Corresponding to Empty and Full Viral Particles Method conditions, such as initial gradient percentages and isocratic hold percentages, were analyzed to enhance sample binding and peak symmetry and to decrease peak tailing. In addition, the upper limit wavelengths for fluorescence detection were obtained. The methods described in Example 5 were used except where indicated. A mixture of samples, Full rAAV6-GLA3 and Empty AAV6-030, were used to further improve the gradient method. An isocratic hold of 19% was selected and gradient start and end percentages were varied. In addition, the excitation and emission wavelengths were varied to obtain preferred wavelengths.

An isocratic hold of 19% resulted in the baseline separation of both full viral particle and empty viral peaks, as shown in FIG. 20. Initial gradient was 0% which was linearly increased to about 15% followed by gradual increase to about 19%, where the isocratic hold demonstrated separation of empty AAV6 particles. Further gradient increase to about 40% or 50% resulted in elution of the peak corresponding to full viral particles. A further gradient increase to about 100% was used to clean the column during the method. It can be preferable to use a lower % of buffer B at the beginning of the gradient to narrow the peak shape and width corresponding to empty AAV6 particles. Hence, a start gradient of 5% was chosen as an initial gradient. The results demonstrated that a 5% initial gradient improved the peak asymmetry of empty AAV6. In addition, a final gradient of about 50% resulted in improved symmetry of the full AAV6 peak. Use of the about 5-15-50% gradient resulted in a resolution of >2.0 and asymmetry and tailing of <2.0 which fit within the requirements for USP methods for HPLC analysis.

In order to ascertain preferred excitation/emission wavelengths, experiments were performed by fixing one parameter and varying the other. Wavelengths for excitation and emission of 280 nm and 348 nm, respectively, demonstrated preferred peak characteristics, detection, and signal to noise ratio.

The response time for sample collection was also varied. It was found that a response time of about 0.5 s was enough to generate at least 20 datapoints across the peak, which is another requirement under the USP. Lower response time can also increase the number of data points, however, files can be large enough to slow down the analysis.

The effect of temperature was also investigated. It was demonstrated that higher temperature resulted in the addition of smaller peaks at high RT. These results indicate that the method can further differentiate other variants of particles. The AAV6 column demonstrated preferred temperatures of 40° C. or cooler, e.g., about 15-25° C. with acceptable performance up to 50° C.

Example 11: Linearity of Injection Volume, Injected Capsid Concentration, and Precision of Multiple Injections Full rAAV6-GLA3 and Empty AAV6-030 samples were used to determine the linearity of injection volume, injected capsid concentration, and precision of multiple injections. In addition, the linearity of different mixed samples prepared at different proportions was investigated.

Injection volumes of between about 1-100 µL were analyzed to determine load linearity. Samples of Full rAAV6-GLA3 and Empty AAV6-030 were used both mixed and independently. Peak area for peaks corresponding to full and empty viral particles were compared. At a volume of up to about 10 µL, both samples showed high linearity despite having vastly different capsid titers. At higher volumes, non-binding of a portion of the sample yielded non-linear increases in peak area.

The linearity of injectable viral particle concentration (e.g., capsids) was determined. Both samples, Full rAAV6-GLA3 and Empty AAV6-030, were diluted in final formulation buffer 2× and 10 µL of each solution was injected. The capsid titer of Full rAAV6-GLA3 was 6.11E+12 Capsids/mL and the capsid titer of Empty AAV6-030 was 3.2E+13 Capsids/mL. The area response was measured for both samples at both peaks and were found to be linear. The major peak for each sample resulted in a high linearity range (6.11E+10–9.55E+8 capsids/injection for Full rAAV6-GLA3 and 3.2E+11–5E9 for Empty AAV6-030) with the lowest point showing >100 sample to noise ratio. Accordingly, the limit of detection (LOD) and limit of quantitation (LOQ) may be much lower. These results indicate that the method is very sensitive, and capsids less than these amounts can also be analyzed for major peaks.

Empty AAV capsids should have a higher detection UV280 vs 260 nm while full AAV should have higher detection UV260 over 280 nm (because of DNA inside the capsids). The same was consistently observed indicating that the assumed peak positions of empty and full AAV are correct.

The % empty and full analysis for each chromatogram was obtained by calculating % of the relevant peak of the total peak areas of all peaks. In order to calculate % empty and full capsids in Full rAAV6-GLA3 and Empty AAV6-030, load linearity (see above) data was used. The data of multiple volumes injected showed that the percent of empty and full in Full rAAV6-GLA3 were 8% and 92%, respectively; while the percent of empty and full AAV particles in Empty AAV6-030 were 6% and 94%, respectively, with reasonable variation (<10%). These values can be used to build a custom standard curve by mixing them in different proportions and calculating theoretical % empty and full in those mixtures. The peak areas of resultant chromatograms can be used to build a simplistic curve (linear or quadratic). Back-calculation can be used to obtain the % recovery in each mixture.

In order to ascertain that a sample had both empty and full AAV peaks and that the peak area response will be linear, a standard curve consisting of mixtures of Full rAAV6-GLA3 and Empty AAV6-030 was prepared and is presented in FIG. 32. From mixtures, 10 µL was injected and peak areas for each peak were obtained. The peak areas were plotted against % Empty or Full injected capsid amount. The linear relationship was used to back-calculate % recovery and was demonstrated to be within ±20%. This experiment also indicated that the range and recovery of mixtures of samples containing both AAV peaks is highly linear ($r^2>0.99$). In order to further refine the curve fit, software was used to fit the linear or quadratic curve. It was found that quadratic curve can also be a good fit with lower residual standard deviation. However, both linear and quadratic curve fits may be used.

TABLE 5

Design of mixtures of two samples for standard curve and resultant peak areas along with % recovery based on linear curve

| Vol of rAAV6-GLA3 (µL) | Vol of Empty AAV6-030 (µL) | Total Volume (µL) | % Full Calc. | % Empty Calc. | Total (%) | Peak Area (Full Peak) | Peak Area (Empty Peak) | Calc. % Full | % Recovery | Calc. % Empty | % Recovery |
|---|---|---|---|---|---|---|---|---|---|---|---|
| 20 | 0 | 20 | 94 | 6 | 100 | 128.71 | 10.21 | 90.7 | 96.5 | 5.3 | 88.7 |
| 15 | 5 | 20 | 72.5 | 27.5 | 100 | 108.23 | 49.13 | 76.0 | 104.8 | 27.5 | 100.1 |
| 10 | 10 | 20 | 51 | 49 | 100 | 75.76 | 87.92 | 52.6 | 103 | 49.7 | 101.3 |

TABLE 5-continued

Design of mixtures of two samples for standard curve and resultant peak areas along with % recovery based on linear curve

| Vol of rAAV6-GLA3 (µL) | Vol of Empty AAV6-030 (µL) | Total Volume (µL) | % Full Calc. | % Empty Calc. | Total (%) | Peak Area (Full Peak) | Peak Area (Empty Peak) | Calc. % Full | % Recovery | Calc. % Empty | % Recovery |
|---|---|---|---|---|---|---|---|---|---|---|---|
| 5 | 15 | 20 | 29.5 | 70.5 | 100 | 43.29 | 126.8 | 29.1 | 98.8 | 71.8 | 101.9 |
| 0 | 20 | 20 | 8 | 92 | 100 | 12.04 | 159.8 | 6.6 | 82.8 | 90.7 | 98.5 |

It was also demonstrated that within a pH range of about 8.8-9.2 of both mobile phases, peak separation was still present with high resolution. However, some peak tailing was observed at pH 9.2, with peak RT shifting at extreme pH conditions (FIG. 33).

In addition to pH, the effects of column temperature were also analyzed. The column compartment temperature was varied from between about 15 to 50° C. and peak separation of empty and full AAV was analyzed. Peak separation was unaffected (with some tailing) at lower temperatures while at >30° C., extra peaks may appear in the chromatograms, as shown in FIG. 34.

The effect of sample temperature on chromatography was also investigated by heating samples to different temperatures. At higher temperatures (e.g., about 90° C.), the samples degraded and did not show any peaks during gradient elution (data not shown). Thus, the method could be used to analyze stability of a sample.

Example 12: Comparison of % Empty and Full Particles Quantified by HPLC Compared to AUC and CryoTEM A total of 10 samples (including Full rAAV6-GLA3, Full rAAV6-384, Full rAAV6-GLA4 (recombinant AAV6 carrying a GLA transgene), and Empty AAV6-030) were analyzed using the HPLC method described in Example 10 and the percent of empty and full capsids were calculated. Five of the samples were sent for CryoTEM analysis and the percent of full and empty capsids were obtained.

The comparative analysis between the HPLC method and the CryoTEM method demonstrated a strong correlation, as shown in Table 6 and Table 7. In the tables, rAAV6-378 has a genome containing an expression cassette for a left ZFN transgene; rAAV6-447 has a genome containing an expression cassette for an F8 (Factor VIII) transgene; and rAAV6-000490 and 18-rAAV6-550 each have a genome containing an expression cassette for a CD19 transgene but were produced in Sf9 and HEK293 cells, respectively.

The correlation between the methods is also shown in FIG. 43 (% empty capsids) and FIG. 44 (% full capsids). The Pearson correlation coefficient (r) for HPLC vs TEM correlation at 95% coverage was 0.999. These results demonstrate that the HPLC methods described herein are accurate when compared to the TEM method of empty and full capsid quantification within samples.

TABLE 6

Comparison of % empty capsids utilizing HPLC and TEM

| Sample | | | % Empty AAV Particles | |
|---|---|---|---|---|
| Sample # | Description | Sample ID | AEX HPLC | CryoTEM |
| 1 | Full | rAAV6-375 | 11.7 | ND |
| 2 | Full | rAAV6-384 | 13.4 | ND |
| 3 | Full | rAAV6-378 | 6.5 | ND |
| 4 | Full | rAAV6-381 | 7.3 | ND |
| 5 | Full | rAAV6-GLA3 | 8.1 | 11 |
| 6 | Full | rAAV6-GLA4 | 13.3 | 17 |
| 7 | Full | rAAV6-447 | 24 | 27 |
| 8 | Full | rAAV6-000490 | 5.4 | ND |
| 9 | Empty | AAV6-030 | 95.6 | 96 |
| 10 | Full | 18-rAAV6-550 | 16.6 | 23 |

TABLE 7

Comparison of % full capsids for HPLC and TEM

| Sample | | | % Full AAV Particles | |
|---|---|---|---|---|
| Sample # | Description | Lot # | AEX HPLC | CryoTEM |
| 1 | Full | rAAV6-375 | 88.3 | ND |
| 2 | Full | rAAV6-384 | 86.6 | ND |
| 3 | Full | rAAV6-378 | 93.4 | ND |
| 4 | Full | rAAV6-381 | 92.7 | ND |
| 5 | Full | rAAV6-GLA3 | 91.9 | 85 |
| 6 | Full | rAAV6-GLA4 | 86.7 | 79 |
| 7 | Full | rAAV6-447 | 76 | 65 |
| 8 | Full | rAAV6-000490 | 94.6 | ND |
| 9 | Empty | AAV6-030 | 4 | 2 |
| 10 | Full | 18-rAAV6-550 | 83.4 | 70 |

Notes:
ND—Not Determined

According to preferred embodiments, the following parameters may be utilized: Line A (Buffer A) about 20 mM bis-Tris propane (BTP) pH 9.0; Line B (Buffer B) about 20 mM bis-Tris propane (BTP), 1 M salt (TMAC) pH 9.0; Line C-LC-MS (or equivalent) grade water; Line D isopropyl alcohol; Seal Wash (SW) about 10% IPA in LC-MS (or equivalent) grade water; Needle Wash (NW) about 50% methanol; UV Detection set up −260±20 nm, 280±20 nm; Fluorescence Detection set up—Excitation/Emission=280 nm/348 nm; Sample Injection volume about 10 µL; Multi-sampler Parameters: Needle Wash—Standard; Draw Speed about 100 µL/min; Eject Speed about 400 µL/min; Wait time after draw about 1.2 s; Sample flush out factor—5; Column temperature about 20° C.; DAD Settings: Signal A—260±20 nm, Reference 400±100 nm, response time >0.25 s; Signal B—280±20 nm, Reference 400±100 nm, response time>0.25 s; Slit about 4 nm; FLD Settings: Excitation—280 nm, Emission—348 nm, response time about 0.25 s.

According certain embodiments, the mobile phase gradient program presented in Table 8 may be utilized.

TABLE 8

Gradient program (1M TMAC as buffer B)

| Time (min) | Buffer A (%) | Buffer B (%) | Buffer C (%) | Buffer D (%) | Flow Rate (mL/min) | Max. Pressure (bar) | Step ID |
|---|---|---|---|---|---|---|---|
| 0 | 95 | 5 | 0 | 0 | 1 | 150 | Initial |
| 1 | 95 | 5 | 0 | 0 | 1 | 150 | Equilibration |
| 3 | 85 | 15 | 0 | 0 | 1 | 150 | First gradient step |
| 4 | 81 | 19 | 0 | 0 | 1 | 150 | Isocratic hold |
| 7 | 81 | 19 | 0 | 0 | 1 | 150 | (19%) |
| 10 | 50 | 50 | 0 | 0 | 1 | 150 | Final gradient |
| 12 | 5 | 95 | 0 | 0 | 1 | 150 | Column |
| 16 | 5 | 95 | 0 | 0 | 1 | 150 | cleaning |
| 16.01 | 95 | 5 | 0 | 0 | 1 | 150 | Column |
| 18 | 95 | 5 | 0 | 0 | 1 | 150 | regeneration for next sample injection |
| 18.01 | 95 | 5 | 0 | 0 | 0 | 150 | End of Run |

Example 13: Broad Utility of the Isocratic Hold HPLC Method for the Separation and Quantitation of Empty and Full Particles Viral preparations of an additional 5 different AAV serotypes, including AAV1, AAV2, AAV3, AAV8, and AAV9, were analyzed using the HPLC method described in Example 10 and the percent of empty and full capsids were calculated. For each serotype, different samples were run to assess chromatographic peak separation and peak positioning for empty AAV capsids and full AAV capsids. In addition, for each serotype, the method was modified with respect to concentration of 1 M TMAC for efficient binding, isocratic hold and both linear gradients on each side of the isocratic hold.

For the AAV1 serotype, samples included AAV1 Empty Lot and AAV1 CMV-GFP, which were purchased from Virovek; and lots 17-AAV-321 and 17-AAV-037, which were manufactured by SGMO Vector Core using triple transfection process in HEK293 cells and purified by CsCl density gradient method. For the triple-transfection method, rAAV were produced by vector core group at Sangamo using platform method. Briefly, HEK293 cells were plated in ten-layer CellSTACK chambers (Corning, Acton, Mass.) and grown for three days to a density of 80%. Three plasmids, an AAV Helper plasmid containing the Rep and Cap genes, an Adenovirus Helper plasmids containing the adenovirus helper genes and a transgene plasmid containing the sequence to be packaged flanked by AAV2 inverted terminal repeats were transfected into the cells using calcium phosphate (Xiao et. al. 1998). After three days the cells were harvested. The cells were lysed by three rounds of freeze/thaw and cell debris was removed by centrifugation. The rAAV was precipitated using polyethylene glycol. After resuspension, the virus was purified by ultracentrifugation overnight on a cesium chloride (CsCl) gradient. The virus was formulated by dialysis and then filter sterilized. The Sangamo samples were isolated to isolate purified primarily full AAV1 particles. The data show that an isocratic hold of 20% resulted in the baseline separation of both full viral particle and empty viral peaks, as shown in FIG. 39. Initial gradient was 0% which was linearly increased to about 8% followed by gradual increase to about 20%, where the isocratic hold demonstrated separation of empty AAV particles. Further gradient increase to about 30% resulted in elution of the peak corresponding to full viral particles. A further gradient increase to about 95% was used to clean the column during the method. The data show that the percent of empty and full in Empty AAV1 was 85.2% and 9.3%, respectively; percent of empty and full in AAV1 CMV-GFP was 13.8% and 84.1%, respectively; percent of empty and full in 17-AAV-321 was 20.6% and 79.4%, respectively; and percent of empty and full in 19-AAV-037 was 6.4% and 90.0%, respectively.

For the AAV2 serotype, samples included AAV2 Empty Lot, which was purchased from Virovek; and lots 17-AAV-077 and 17-AAV-155, which were manufactured by SGMO Vector Core using triple transfection process in HEK293 cells and purified by CsCl density gradient method. The Sangamo samples were isolated to enrich primarily full AAV2 particles. The data show that an isocratic hold of 12% resulted in the baseline separation of both full viral particle and empty viral peaks, as shown in FIG. 40. Initial gradient was 0% which was linearly increased to about 8% followed by gradual increase to about 12%, where the isocratic hold demonstrated separation of empty AAV particles. Further gradient increase to about 30% resulted in elution of the peak corresponding to full viral particles. A further gradient increase to about 100% was used to clean the column during the method. The data show that the percent of empty and full in AAV2 Empty was 72.3% and 21.4%, respectively; percent of empty and full in 17-AAV-077 was 5.9% and 79.6%, respectively; and percent of empty and full in 17-AAV-155 was 78.5% and 8.9%, respectively.

For the AAV3 serotype, samples included AAV3 Empty Lot and AAV3 CMV-GFP, which were purchased from Virovek; and lots 17-AAV-124 and 17-AAV-324, which were manufactured by SGMO Vector Core using triple transfection process in HEK293 cells and purified by CsCl density gradient method. The Sangamo samples were isolated to isolate purified primarily full AAV3 particles. The data show that an isocratic hold of 15% resulted in the baseline separation of both full viral particle and empty viral peaks, as shown in FIG. 41. Initial gradient was 0% which was linearly increased to about 8% followed by gradual increase to about 15%, where the isocratic hold demonstrated separation of empty AAV particles. Further gradient increase to about 30% resulted in elution of the peak corresponding to full viral particles. A further gradient increase to about 100% was used to clean the column during the method. The data show that the percent of empty and full in AAV3 Empty was 74.1% and 17.9%, respectively; percent of empty and full in AAV3 CMV-GFP was 55.2% and 41.5%, respectively; percent of empty and full in 17-AAV-124 was 55.4% and 44.6%, respectively; and percent of empty and full in 17-AAV-324 was 72.9% and 27.2%, respectively.

For the AAV8 serotype, samples included AAV8 Empty (17-AAV-082) and lots 18-AAV-070, 17-AAV-339, 17-AAV-340, and 17-AAV-341, which were manufactured by SGMO Vector Core using triple transfection process in HEK293 cells and purified by CsCl density gradient method. AAV8 Empty lot was isolated to enrich empty AAV8 particles while all other lots were isolated to isolate purified full AAV8 particles. AAV8 RSM (predominately comprised of full AAV8 capsids), purchased from ATCC, manufactured by Atlantic Gene Therapies—UMR 1089 in Nantes (France) and the Center of Animal Biotechnology and Gene Therapy (CBATEG) at the Universitat Autonoma de Barcelona (Spain), was also tested. The data show that an isocratic hold of 14% resulted in the baseline separation of both full viral particle and empty viral peaks, as shown in FIGS. 42A and 42B. Initial gradient was 0% which was linearly increased to about 8% followed by gradual increase to about 14%, where the isocratic hold demonstrated separation of empty AAV particles. Further gradient increase to about 30% resulted in elution of the peak corresponding to full viral particles. A further gradient increase to about 95% was used to clean the column during the method. The data show that the percent of empty and full in AAV8 Empty was 76.6% and 22.2%, respectively; percent of empty and full in AAV8 Lot 18-070 was 15.2% and 81.5%, respectively; percent of empty and full in AAV8 Lot 17-339 was 1.8% and 95.5%, respectively; percent of empty and full in AAV8 Lot 17-340 was 28% and 70.4%, respectively; percent of empty and full in AAV8 Lot 17-341 was 4.3% and 93.3%, respectively; and percent of empty and full in AAV8 RSM was 0% (none detected) and 100%, respectively. The concentration of AAV8 RSM being low might cause the empty peak to be below detectable limit.

For the AAV9 serotype, samples included AAV9 Lots 070 and 076, which were manufactured using baculovirus-based infection in 519 cells process and purified by affinity chromatography; and Lot 24, which was manufactured by SGMO Vector Core using triple transfection process in HEK293 cells and purified by CsCl density gradient method. These lots were isolated to isolate purified primarily full AAV9 particles. The data show that the AAV9 serotype, an isocratic hold of 5% resulted in the baseline separation of both full viral particle and empty viral peaks, as shown in FIG. 43. Initial gradient was 0% which was linearly increased to about 3% followed by gradual increase to about 5%, where the isocratic hold demonstrated separation of empty AAV particles. Further gradient increase to about 40% resulted in elution of the peak corresponding to full viral particles. A further gradient increase to about 100% was used to clean the column during the method. The data show that the percent of empty and full in PD Lot 076 was 53.6% and 43.3%, respectively; percent of empty and full in PD70 Lot 19-BAV-484PD was 5.8% and 87.8%, respectively; percent of empty and full in PD76 Lot 20-BAV-027PD was 54.2% and 41.1%, respectively; and percent of empty and full in Run24 Lot 19-BAV-470 was 2.7% and 97.3%, respectively.

TABLE 9

HPLC Method Parameters for different AAV Serotypes

| AAV8 | | AAV2 | | AAV9 | | AAV1 | | AAV3 | | Serotype |
|---|---|---|---|---|---|---|---|---|---|---|
| Buffer A (%) | Buffer B (%) | Buffer A (%) | Buffer B (%) | Buffer A (%) | Buffer B (%) | Buffer A (%) | Buffer B (%) | Buffer A (%) | Buffer B (%) | Step Information |
| 100 | 0 | 100 | 0 | 100 | 0 | 100 | 0 | 100 | 0 | Initial equilibration |
| 92 | 8 | 92 | 8 | 97 | 3 | 92 | 8 | 92 | 8 | First gradient step |
| 86 | 14 | 88 | 12 | 95 | 5 | 80 | 20 | 85 | 15 | Isocratic hold |
| 70 | 30 | 70 | 30 | 60 | 40 | 70 | 30 | 70 | 30 | Final gradient |
| 5 | 95 | 0 | 100 | 0 | 100 | 5 | 95 | 0 | 100 | Column cleaning |

Buffer A: 20 mM BTP, pH 9.0;
Buffer B: 20 mM BTP, 1M TMAC, pH 9.0

What is claimed is:

1. A method of separating empty and full capsids in a viral preparation, the method comprising running the viral preparation and a mobile phase through an anion exchange column, wherein the mobile phase is run under conditions comprising a discontinuous elution gradient and at least one isocratic hold incorporated into the gradient.

2. A method of quantitating empty and full capsids in a viral preparation, the method comprising running the viral preparation and a mobile phase through an anion exchange column, wherein the mobile phase is run under conditions comprising a discontinuous elution gradient and at least one isocratic hold incorporated into the gradient.

3. The method of claim 1, wherein the viral preparation and mobile phase are run on a high-performance liquid chromatography (HPLC) system.

4. The method of claim 1, wherein the empty and full capsids are separated by baseline resolution.

5. The method of claim 4, wherein the baseline resolution is greater than 2.0.

6. The method of claim 1, wherein the capsids comprise adeno-associated virus (AAV) capsids.

7. The method of claim 1, wherein the anion column is a strong anion exchange (SAX) column.

8. The method of claim 7, wherein the SAX column is a quaternary amine (Q-amine) column.

9. The method of claim 1, wherein the anion exchange column is a monolith column.

10. The method of claim 1, wherein the mobile phase comprises a salt.

11. The method of claim 10, wherein the salt is tetramethylammonium chloride (TMAC) or sodium acetate.

12. The method of claim 10, wherein the final gradient of the mobile phase comprises 0.5 to 5 M salt.

13. The method of claim 1, wherein the at least one isocratic hold is introduced before the mobile phase reaches 50% of the final gradient.

14. The method of claim 1, wherein the pH of the mobile phase is about 8 to about 10.

15. The method of claim 14, wherein the pH of the mobile phase is about 9.

16. The method of claim 1, wherein the column has a temperature between 0° C. and 50° C.

17. The method of claim 6, wherein the AAV is derived from one or more serotypes, selected from AAV1, AAV2, AAV3, AAV6, AAV8, and AAV9.

18. The method of claim 6, wherein the full capsid in the viral preparation comprises a nucleic acid transgene construct between about 20 base pairs and about 9,000 base pairs.

19. A viral preparation that is enriched for empty viral capsids, the preparation being obtained by a method of claim 1.

20. A viral preparation that is enriched for full viral capsids, the preparation being obtained by a method of claim 1.

21. The method of claim 12, wherein the final gradient of the mobile phase comprises 1 M salt.

22. The method of claim 16, wherein the column has a temperature between 20° C. and 25° C.

23. The viral preparation of claim 19, wherein no more than 20% of the viral capsids in the preparation are full viral capsids.

24. The viral preparation of claim 20, wherein no more than 20% of the viral capsids in the preparation are empty viral capsids.

* * * * *